United States Patent [19]

Greenlee et al.

[11] Patent Number: 5,264,439

[45] Date of Patent: Nov. 23, 1993

[54] QUINAZOLINONE, TRIAZOLINONE AND PYRIMIDINONE ANGIOTENSIN II ANTAGONISTS INCORPORATING A SUBSTITUTED BENZYL ELEMENT

[75] Inventors: William J. Greenlee, Teaneck, N.J.; David Hangauer, East Amherst, N.Y.; Arthur A. Patchett; Thomas F. Walsh, both of Westfield, N.J.; Kenneth J. Fitch, Cranford, N.J.; Daljit S. Dhanoa, Tinton Falls, N.J.; Ralph A. Rivero, Eatontown, N.J.

[73] Assignee: Merck & Co., Inc., Rahway, N.J.

[21] Appl. No.: 744,138

[22] Filed: Aug. 13, 1991

Related U.S. Application Data

[63] Continuation-in-part of Ser. No. 671,552, Mar. 19, 1991, abandoned, which is a continuation of Ser. No. 479,786, Feb. 13, 1990, abandoned.

[51] Int. Cl.$^5$ ................ A61K 31/505; C07D 239/90
[52] U.S. Cl. ................ 514/259; 544/244; 544/284; 544/287; 544/288; 544/289
[58] Field of Search ............. 544/287, 284, 288, 289, 544/244; 514/259

[56] References Cited

U.S. PATENT DOCUMENTS

| | | | |
|---|---|---|---|
| 3,360,518 | 12/1967 | Shetty | 544/288 |
| 4,522,945 | 6/1985 | Vandenberk et al. | 544/287 |
| 4,849,518 | 7/1989 | Glazer | 544/289 |

*Primary Examiner*—C. Warren Ivy
*Assistant Examiner*—James H. Turnipseed
*Attorney, Agent, or Firm*—William H. Nicholson; Valerie J. Camara; Joseph F. DiPrima

[57] ABSTRACT

Substituted heterocycles attached through a methylene bridge to novel substituted phenyl derivatives of the Formula I are useful as angiotensin II antagonists.

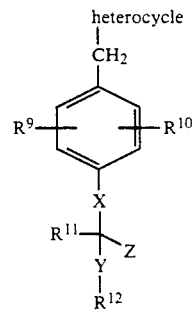

8 Claims, No Drawings

QUINAZOLINONE, TRIAZOLINONE AND PYRIMIDINONE ANGIOTENSIN II ANTAGONISTS INCORPORATING A SUBSTITUTED BENZYL ELEMENT

BACKGROUND OF THE INVENTION

The present application is a continuation in part of copending application Ser. No. 671,552 filed on Mar. 19, 1991, now abandoned which is a continuation in part application of copending Ser. No. 479,786 filed on Feb. 13, 1990 (now abandoned).

The Renin-angiotensin system (RAS) plays a central role in the regulation of normal blood pressure and seems to be critically involved in hypertension development and maintenance as well as congestive heart failure. Angiotensin II (A II), is an octapeptide hormone produced mainly in the blood during the cleavage of angiotensin I by angiotensin converting enzyme (ACE) localized on the endothelium of blood vessels of lung, kidney, and many other organs. It is the end product of the reninangiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by partial agonist activity and lack of oral absorption [M. Antonaccio. *Clin. Exp. Hypertens.* A4, 27-46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246-271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; 4,582,847; and 4,880,804 and in European Patent Applications 028,834; 245,637; 253,310; and 291,969; and in articles by A. T. Chiu, et al. [*Eur. J. Pharm. Exp. Therap*, 157, 13-21 (1988)] and by P. C. Wong, et al. [*J. Pharm. Exp. Therap*, 247, 1-7 (1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

None of the compounds disclosed within this application or in any U.S. Patent, European Applications or literature publication are of the type containing substituted heterocycles bonded through an alkyl bridge to a novel substituted phenyl of the type disclosed herein. The quinazolin-4(1H)-ones, triazolinones, triazolinimines, and pyrimidinones have been disclosed in earlier U.S. Patent applications focusing on the heterocyclic fragment of the antagonist design. The serial numbers of these applications are Ser. Nos. 351,508; 358,971; 375,655; 360,673; 375,217; and 386,328 and are hereby incorporated by reference.

BRIEF DESCRIPTION OF THE INVENTION

This invention is directed to substituted heterocycles attached through a methylene bridge to novel substituted phenyl derivatives to give compounds of the Formula I, which are angiotensin II antagonists and are useful in the treatment of hypertension and congestive heart failure. The compounds of the invention are useful as ocular antihypertensives.

Specifically, the compounds of this invention contain a heterocyclic moiety which is substituted at the specified positions and to which a methylene bridge connecting a novel substituted phenyl group as defined by the lower portion of Formula I, is attached. Additionally, pharmaceutically acceptable compositions of these novel compounds, as the sole therapeutically active ingredient and in combination with diuretics and other antihypertensive agents, including beta blockers, angiotensin converting enzyme inhibitors, calcium channel blockers or a combination thereof are disclosed and claimed. Further, methods of treating hypertension and congestive heart failure are described and claimed.

The compounds of this invention have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

In addition, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

DETAILED DESCRIPTION OF THE INVENTION

This invention relates to compounds of the general Formula I:

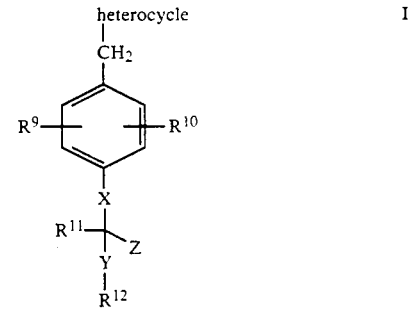

or a pharmaceutically acceptable salt thereof, and the heterocycle is specifically defined as:

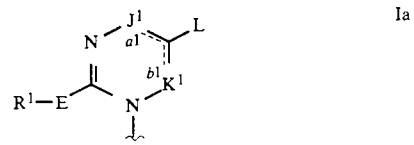

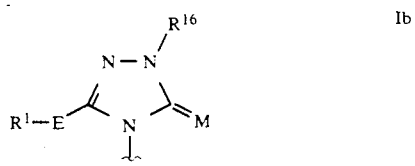

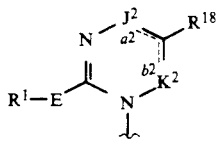

R¹ is:
- (a) (C₁–C₆)-alkyl, (C₂–C₆)-alkenyl or (C₂–C₆)-alkynyl each of which is unsubstituted or substituted with a substituent selected from the group consisting of:
  - i) aryl as defined below,
  - ii) (C₃–C₇)-cycloalkyl,
  - iii) Cl, Br, I, F,
  - iv) OH,
  - v) NH₂,
  - vi) NH(C₁–C₄)-alkyl,
  - vii) N[(C₁–C₄)-alkyl]₂,
  - viii) NHSO₂R²,
  - ix) CF₃,
  - x) COOR², or
  - xi) SO₂NHR²ᵃ; and
- (b) aryl, wherein aryl is defined as phenyl or naphthyl unsubstituted or substituted with 1 or 2 substituents selected from the group consisting of:
  - i) Br, I, Cl, F,
  - ii) (C₁–C₄)-alkyl,
  - iii) (C₁–C₄)-alkoxy,
  - iv) NO₂
  - v) CF₃
  - vi) SO₂NR²ᵃR²ᵃ,
  - vii) (C₁–C₄)-alkylthio,
  - viii) hydroxy,
  - ix) amino,
  - x) (C₃–C₇)-cycloalkyl,
  - xi) (C₃–C₁₀)-alkenyl; and
- (c) an unsubstituted, monosubstituted or disubstituted heteroaromatic 5- or 6-membered cyclic moiety, which have one or two members selected from the group consisting of N, O, S and wherein the substituents are members selected from the group consisting of:
  - i) Cl, Br, I, or F,
  - ii) OH,
  - iii) SH,
  - iv) NO₂,
  - v) (C₁–C₄)-alkyl,
  - vi) (C₂–C₄)-alkenyl,
  - vii) (C₂–C₄)-alkynyl,
  - viii) (C₁–C₄)-alkoxy, or
  - ix) CF₃, or
- (d) (C₁–C₄)-perfluoroalkyl; and E is:
- (a) a single bond,
- (b) —S(O)ₙ(CH₂)ₛ—, or
- (c) —O—; and n is 0 to 2; and
s is 0 to 5; and J¹ is (a)—C(=M)—, (b) J¹ and L are connected together to form a 6-carbon aromatic ring substituted with R⁷ᵃ, R⁷ᵇ, R⁸ᵃ and R⁸ᵇ or (c) J¹ and L are connected together to form a 6-membered aromatic ring having one nitrogen atom not at J¹, substituted with R⁷ᵃ, R⁷ᵇ, R⁸ᵃ and R⁸ᵇ; and K¹ is (a)—C(=M)—, (b) K¹ and L are connected together to form a 6-carbon aromatic ring substituted with R⁷ᵃ, R⁷ᵇ, R⁸ᵃ and R⁸ᵇ, or (c) K¹ and L are connected together to form a 6-membered aromatic ring having one nitrogen atom, substituted on the carbon atoms with R⁷ᵃ, R⁷ᵇ and R⁸ᵇ; and one of a¹ or b¹ is a double bond in structures Ia provided that when J¹ is —C(=M)— then b¹ is a double bond and when K¹ is —C(=M)— then a¹ is a double bond; and L is the point of attachment of the 6-membered fused aromatic ring optionally having one nitrogen atom; and J² is (a)—C(=M)—, or (b) —C(R¹⁷)—; and
K² is (a)—C(=M)—, or (b)—C(R¹⁷)—, provided that one and only one of J² and K² is —C(=M)—; and one of a² or b² is a double bond in structure Ic provided that when J² is —C(=M)— then b² is a double bond and when K² is —C(=M)— then a² is a double bond.

M is O, S or NR¹⁵; and

R² is:
- (a) H, or
- (b) (C₁–C₆)-alkyl; and

R²ᵃ is:
- (a) R²,
- (b) CH₂-aryl, or
- (c) aryl; and

R⁷ᵃ and R⁷ᵇ are independently
- (a) H,
- (b) (C₁–C₆)-alkyl, (C₂–C₆)-alkenyl or (C₂–C₆)-alkynyl,
- (c) Cl, Br, I, F,
- (d) CF₃, or
- (e) when R⁷ᵃ and R⁷ᵇ are bonded to adjacent carbon atoms, they can be joined to form a phenyl ring;

R⁸ᵃ and R⁸ᵇ are independently
- (a) H,
- (b) aryl-(C₁–C₄)-alkyl,
- (c) heteroaryl-(C₁–C₄)-alkyl,
- (d) (C₁–C₆)-alkyl, which is unsubstituted or substituted with a substituent selected from the group consisting of: —CON(R²ᵃ)₂, -heteroaryl, —S(O)ₓ-—R²¹, -tetrazol-5-yl, —CONHSO₂R²¹, —SO₂NH-heteroaryl, —SO₂NHCOR²¹, —PO(OR²)₂, —PO-(OR²ᵃ)₂, —SO₂NH—CN, —NR²COOR²¹, —OH, —NH₂, guanidino, (C₁–C₄)-alkoxy, (C₁–C₄)-alkylthio, (C₁–C₄)-alkylamino, (C₁–C₄)-dialkylamino, —COOR²ᵃ, —CONHR²ᵃ, —O—COR²ᵃ, or aryl,
- (e) —CO-aryl,
- (f) (C₃–C₇)-cycloalkyl,
- (g) Cl, Br, I, F,
- (h) —OH,
- (i) —OR²¹,
- (j) —SH,
- (k) —S(O)ₙ—(C₁–C₄)-alkyl,
- (l) —COR²ᵃ,
- (m) —CO₂H,
- (n) —CO₂—(C₁–C₄)-alkyl,
- (o) —SO₃H,
- (p) —NR²R²¹,
- (q) —NR²COR²¹,
- (r) —NR²COOR²¹,
- (s) —SO₂NHR²ᵃ,
- (t) —SO₂NR²R²ᵃ,
- (u) —NO₂,
- (v) —NHSO₂CF₃,
- (w) —CONR²ᵃR²ᵃ,
- (x) —(C₁–C₄)-perfluoroalkyl,
- (y) —COOR², (z) —SO₃H,
(aa) —N(R²)SO₂R²¹,
(bb) —NR²CONR⁴R²¹,
(cc) —OC(=O)NR²¹R²ᵃ,
(dd) -aryl,
(ee) —NHSO₂CF₃,
(ff) —SO₂NH-heteroaryl,
(gg) —SO₂NHCOR²¹,
(hh) —CONHSO₂R²¹,
(ii) —PO(OR²)₂,
(jj) -tetrazol-5-yl,
(kk) —CONH(tetrazol-5-yl),
(ll) —SO₂NHCN, or
(mm) -heteroaryl; and R⁹ and R¹⁰ are independently:
  (a) H,
  (b) (C₁-C₆)-alkyl, unsubstituted or substituted with (C₃-C₇)-cycloalkyl,
  (c) (C₂-C₆)-alkenyl,
  (d) (C₂-C₆)-alkynyl,
  (e) Cl, Br, F, I,
  (f) (C₁-C₆)-alkoxy,
  (g) when R⁹ and R¹⁰ are on adjacent carbons, they can be joined to form an phenyl ring,
  (h) perfluoro-(C₁-C₆)-alkyl,
  (i) (C₃-C₇)-cycloalkyl, unsubstituted or substituted with (C₁-C₆)-alkyl,
  (j) aryl,
  (k) (C₁-C₆)-alkyl-S(O)ₙ—(CH₂)ₙ—,
  (l) hydroxy-(C₁-C₆)-alkyl,
  (m) —CF₃,
  (n) —CO₂R²ᵃ,
  (o) —OH,
  (p) —NR²R²¹,
  (q) —[(C₁-C₆)-alkyl]NR²R²¹,
  (r) —NO₂,
  (s) —(CH₂)ₙ—SO₂—N(R²)₂,
  (t) —NR²CO—(C₁-C₄)-alkyl, or
  (u) —CON(R²)₂;

X is:
  (a) —O—,
  (b) —S(O)ₙ—,
  (c) —NR¹³—
  (d) —CH₂O—,
  (e) —CH₂S(O)ₙ,
  (f) —CH₂NR¹³—,
  (g) —OCH₂—,
  (h) —NR¹³CH₂—,
  (i) —S(O)ₙCH₂—,
  (j) —CH₂—,
  (k) —(CH₂)₂—,
  (l) single bond, or
  (m) —CH=, wherein Y and R¹² are absent forming a —C=C— bridge to the carbon bearing Z and R¹¹; and Y is:
  (a) single bond,
  (b) —O—,
  (c) —S(O)ₙ—,
  (d) —NR¹³—, or
  (e) —CH₂—; and except that X and Y are not defined in such a way that the carbon atom to which Z is attached also simultaneously is bonded to two heteroatoms (O, N, S, SO, SO₂);

R¹¹ and R¹² are independently:
  (a) H,
  (b) (C₁-C₆)-alkyl, unsubstituted or substituted with a substituent selected from the group consisting of:
    (i) aryl,
    (ii) (C₃-C₇)-cycloalkyl,
    (iii) NR²R²¹,
    (iv) morpholin-4-yl,
    (v) OH,
    (vi) CO₂R²ᵃ, or
    (vii) CON(R²)₂,
  (c) aryl or aryl-(C₁-C₂)-alkyl, unsubstituted or substituted with 1 to 3 substitutents selected from the group consisting of:
    (i) Cl, Br, I, F,
    (ii) (C₁-C₆)-alkyl,
    (iii) [(C₁-C₅)-alkenyl]CH₂—,
    (iv) [(C₁-C₅)-alkynyl]CH₂—,
    (v) (C₁-C₆)-alkyl-S(O)ₙ—(CH₂)ₙ—,
    (vi) —CF₃,
    (vii) —CO₂R²ᵃ,
    (viii) —OH,
    (ix) —NR²R²¹,
    (x) —NO₂,
    (xi) —NR²COR²,
    (xii) —CON(R²)₂,
    (xiii) —G—[(C₁-C₆)-alkyl]-R²³,
    (xiv) —N[CH₂CH₂]₂Q, or
    (xv) —P(O)[O—(C₁-C₄)-alkyl]₂,
    and can additionally be substituted with 1 or 2 substituents selected from the group consisting of: Br, Cl or F,
  (d) (C₃-C₇)-cycloalkyl, or
  (e) when Y is single bond, R¹¹ and R¹² can be joined to form a ring of 5 to 7 carbon atoms, the ring can be benzo-fused and one carbon of which can be replaced with a heteroatom selected from the group consisting of: O, S(O)ₓ and NR²²; and G is: a single bond, O, S(O)ₓ or NR²³; and
Q is: O, S(O)ₓ or NR²²; and
R¹³ is:
  (a) H,
  (b) (C₁-C₆)-alkyl,
  (c) aryl,
  (d) aryl-(C₁-C₆)-alkyl-(C=O)—,
  (e) (C₁-C₆)-alkyl-(C=O)—,
  (f) [(C₂-C₅)-alkenyl]CH₂—,
  (g) [(C₂-C₅)-alkynyl]CH₂—, or
  (h) aryl-CH₂—; and Z is:
  (a) —CO₂H,
  (b) —CO₂R²⁴,
  (c) -tetrazol-5-yl,
  (d) —CONH(tetrazol-5-yl)
  (e) —CONHSO₂-aryl,
  (f) —CONHSO₂—(C₁-C₈)-alkyl, wherein the alkyl group is unsubstituted or substituted with a substituent selected from the group consisting of: —OH, —SH, —O(C₁-C₄)-alkyl, —S—(C₁-C₄)-alkyl, —CF₃, Cl, Br, F, I, —NO₂, —CO₂H, —CO₂—(C₁-C₄)-alkyl, —NH₂, —NH[(C₁-C₄)-alkyl], —N[(C₁-C₄)-alkyl]₂; and
  (g) —CONHSO₂—(C₁-C₄)-perfluoroalkyl,
  (h) —CONHSO₂-heteroaryl, or
  (i) —CONHSO₂NR²ᵃR²ᵃ; and
  (j) —SO₂NHCO-aryl,
  (k) —SO₂NHCO—(C₁-C₈)-alkyl, wherein the alkyl group is unsubstituted or substituted with a substituent selected from the group consisting of: —OH, —SH, —O(C₁-C₄)-alkyl, —S—(C₁-C₄)-alkyl, —CF$_3$, Cl, Br, F, I, —NO$_2$, —CO$_2$H, —CO$_2$—(C$_1$-C$_4$)-alkyl, —NH$_2$, —NH[(C$_1$-C$_4$)-alkyl], —N[(C$_1$-C$_4$)-alkyl]$_2$; and
- (l) —SO$_2$NHCO—(C$_1$-C$_4$)-perfluoroalkyl,
- (m) —SO$_2$NHCO-heteroaryl,
- (n) —SO$_2$NHCONR$^{2a}$R$^{2a}$;
- (o) —PO(OH)$_2$,
- (p) —PO(OR$^2$)$_2$, or
- (q) —PO(OH)(OR$^2$); and R$^{14}$ is:
- (a) H,
- (b) (C$_1$-C$_8$)-alkyl,
- (c) (C$_1$-C$_8$)-perfluoroalkyl,
- (d) (C$_3$-C$_6$)-cycloalkyl,
- (e) phenyl, or
- (f) benzyl; and R$^{15}$ is
- (a) H,
- (b) aryl, which is unsubstituted or substituted with 1 or 2 substituents selected from the group consisting of: Cl, Br, I, F —O—(C$_1$-C$_4$)-alkyl, (C$_1$-C$_4$)-alkyl, —NO$_2$, —CF$_3$, —SO$_2$NR$^2$R$^{2a}$, —S—(C$_1$-C$_4$)-alkyl, —OH, —NH$_2$, (C$_3$-C$_7$)-cycloalkyl, (C$_3$-C$_{10}$)-alkenyl;
- (c) (C$_1$-C$_6$)-alkyl, (C$_2$-C$_6$)-alkenyl or (C$_2$-C$_6$)-alkynyl each of which is unsubstituted or substituted with one or more substituents selected from the group consisting of: aryl, (C$_3$-C$_7$)-cycloalkyl, Cl, Br, I, F, —OH, —NH$_2$, —NH[(C$_1$-C$_4$)-alkyl], —N[(C$_1$-C$_4$)-alkyl]$_2$, —NH—SO$_2$R$^{2a}$, —COOR$^{2a}$, —SO$_2$NHR$^{2a}$; or
- (d) an unsubstituted, monosubstituted or disubstituted aromatic 5 or 6 membered ring which can contain one or two heteroatoms selected from the group consisting of N, O, S, and wherein the substituents are members selected from the group consisting of —OH, —SH, (C$_1$-C$_4$)-alkyl, (C$_1$-C$_4$)-alkyloxy, —CF$_3$, Cl, Br, I, F, or NO$_2$; and R$^{16}$ is
- (a) (C$_1$-C$_{10}$)-alkyl;
- (b) substituted (C$_1$-C$_{10}$)-alkyl in which one or two substituent(s) selected from the group consisting of:
  - (1) I, Br, Cl, F,
  - (2) hydroxy,
  - (3) (C$_1$-C$_{10}$)-alkoxy,
  - (4) (C$_1$-C$_5$)-alkoxycarbonyl,
  - (5) (C$_1$-C$_5$)-acyloxy,
  - (6) (C$_3$-C$_8$)-cycloalkyl,
  - (7) aryl,
  - (8) substituted aryl, in which the substituents are V and W,
  - (9) (C$_1$-C$_{10}$)-alkyl-S(O)$_n$,
  - (10) (C$_3$-C$_8$)-cycloalkyl-S(O)$_n$,
  - (11) phenyl-S(O)$_n$,
  - (12) substituted phenyl-S(O)$_n$, in which the substituents are V and W,
  - (13) oxo,
  - (14) carboxy,
  - (15) NR$^{2a}$R$^{2a}$,
  - (16) (C$_1$-C$_5$)alkylaminocarbonyl,
- (c) (C$_1$-C$_4$)-perfluoroalkyl,
- (d) (C$_2$-C$_{10}$)-alkenyl,
- (e) (C$_2$-C$_{10}$)-alkynyl,
- (f) (C$_3$-C$_8$)-cycloalkyl,
- (g) substituted (C$_3$-C$_8$)-cycloalkyl, in which the substituent is selected from:
  - (1) (C$_1$-C$_5$)-alkyl, or
  - (2) (C$_1$-C$_5$)-alkoxy;
- (h) aryl,
- (i) substituted aryl, in which the substituents are V and W,
- (j) aryl-(CH$_2$)$_r$—(M$_1$)$_z$—(CH$_2$)$_t$—
- (k) substituted aryl-(CH$_2$)$_r$—(M$_1$)$_z$—(CH$_2$)$_t$— in which the aryl group is substituted with V and W, (l) 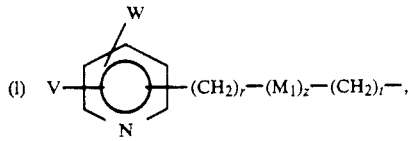

(m) 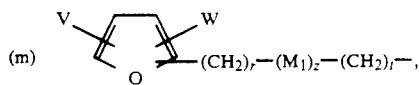

(n) 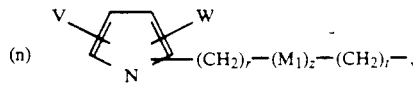

(o) 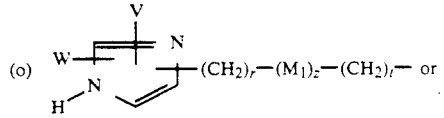 or (p) 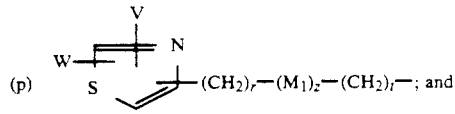; and

- (q) -[(C$_1$-C$_4$)-alkyl]NR$^2$R$^{21}$,
- (r) -[(C$_1$-C$_4$)-alkyl]NR$^2$COR$^{21}$,
- (s) -[(C$_1$-C$_4$)-alkyl]NR$^2$COOR$^{21}$,
- (t) -[(C$_1$-C$_4$)-alkyl]CONR$^{2a}$R$^{2a}$,
- (u) -[(C$_1$-C$_4$)-alkyl]N(R$^2$)SO$_2$R$^{21}$,
- (v) -[(C$_1$-C$_4$)-alkyl]NR$^2$CONR$^4$R$^{21}$, or
- (w) -[(C$_1$-C$_4$)-alkyl]OC(=O)NR$^{21}$R$^{2a}$; and V and W are each independently selected from:
- (a) H,
- (b) (C$_1$-C$_5$)-alkoxy,
- (c) (C$_1$-C$_5$)-alkyl,
- (d) hydroxy,
- (e) (C$_1$-C$_5$)-alkyl-S(O)$_n$,
- (f) —CN,
- (g) —NO$_2$,
- (h) —NR$^2$R$^{2a}$,
- (i) (C$_1$-C$_5$)-acyl-NR$^2$R$^{2a}$,
- (j) —CO$_2$R$^{2a}$,
- (k) (C$_1$-C$_5$)-alkyl-carbonyl,
- (l) CF$_3$,
- (m) I, Br, Cl, F,
- (n) hydroxy-(C$_1$-C$_4$)-alkyl-,
- (o) carboxy-(C$_1$-C$_4$)-alkyl-,
- (p) -tetrazol-5-yl,
- (q) —NH—SO$_2$CF$_3$, or
- (r) aryl; and M$_1$ is M or —C(O)—; and
z is 0 or 1; and
r and t are 0 to 2; and
R$^{17}$ and R$^{18}$ are each independently selected from:
- (a) H,
- (b) aryl-(C$_1$-C$_4$)-alkyl-,
- (c) heteroaryl-(C$_1$-C$_4$)-alkyl-, (d) $(C_1-C_4)$-alkyl unsubstituted or substituted with a substituent selected from the group consisting of —OH, —NH$_2$, guanidino, $(C_1-C_4)$-alkoxy, $(C_1-C_4)$-alkylthio, $(C_1-C_4)$-alkylamino, $(C_1-C_4)$-dialkylamino, —COOR$^{2a}$, —CONHR$^{2a}$, —O—COR$^{2a}$, CF$_3$;
(e) $(C_1-C_4)$-alkenyl,
(f) —CO-aryl,
(g) $(C_3-C_7)$-cycloalkyl,
(h) Cl, Br, I, F,
(i) —OH,
(j) —O—$(C_1-C_4)$-alkyl,
(k) -$(C_1-C_4)$-perfluoroalkyl,
(l) —SH,
(m) —S(O)$_n$—$(C_1-C_4)$-alkyl,
(n) —CHO,
(o) —CO$_2$R$^{2a}$
(p) —SO$_3$H,
(q) —NH$_2$,
(r) —NH[$(C_1-C_4)$-alkyl],
(s) —N[$(C_1-C_4)$-alkyl]$_2$,
(t) —NHCO$_2$—$(C_1-C_4)$-alkyl,
(u) —SO$_2$NR$^2$R$^{2a}$,
(v) —CH$_2$OCOR$^{2a}$
(w) —NH—SO$_2$—$(C_1-C_4)$-alkyl,
(x) 5 or 6 membered saturated heterocycle having one nitrogen atom and optionally having one other heteroatom selected from N, O, or S, wherein the 5- or 6-membered saturated heterocycle is selected from the group consisting of: pyrrolidine, morpholine, or piperazine,
(y) aryl,
(z) heteroaryl, wherein heteroaryl is a 5 or 6 membered aromatic ring having one or two heteroatoms selected from the group consisting of O, N, or S,
(aa) tetrazol-5-yl,
(bb) -[$(C_1-C_4)$-alkyl]NR$^2$R$^{21}$,
(cc) -[$(C_1-C_4)$-alkyl]NR$^2$COR$^{21}$,
(dd) -[$(C_1-C_4)$-alkyl]NR$^2$COOR$^{21}$,
(ee) -[$(C_1-C_4)$-alkyl]CONR$^{2a}$R$^{2a}$,
(ff) -[$(C_1-C_4)$-alkyl]N(R$^2$)SO$_2$R$^{21}$,
(gg) -[$(C_1-C_4)$-alkyl]NR$^2$CONR$^4$R$^{21}$, or
(hh) -[$(C_1-C_4)$-alkyl]OC(=O)NR$^{21}$R$^{2a}$; and
R$^{21}$ is:
(a) aryl, or
(b) $(C_1-C_4)$-alkyl, is unsubstituted or substituted with:
  i) NH$_2$,
  ii) NH[$(C_1-C_4)$-alkyl],
  iii) N[$(C_1-C_4)$-alkyl]$_2$,
  iv) CO$_2$H,
  v) CO$_2$($C_1-C_4$)-alkyl,
  vi) OH,
  vii) SO$_3$H, or
  viii) SO$_2$NH$_2$; and
R$^{22}$ is:
(a) H,
(b) $(C_1-C_4)$-alkyl,
(c) $(C_1-C_4)$-alkoxyl,
(d) aryl,
(e) aryl-$(C_1-C_4)$-alkyl,
(f) CO$_2$R$^{2a}$,
(g) CON(R$^2$)$_2$,
(h) SO$_2$R$^{2a}$,
(i) SO$_2$N(R$^2$)$_2$,
(j) P(O)[$(C_1-C_4)$-alkoxyl]$_2$, or
(k) imidazol-2-yl or imidazol-4-yl, in which the imidazolyl can be substituted with $(C_1-C_4)$-alkyl; and
R$^{23}$ is:

(a) OH,
(b) NR$^2$R$^{21}$,
(c) CO$_2$R$^{2a}$,
(d) CON(R$^2$)$_2$,
(e) S(O)$_x$—$(C_1-C_4)$-alkyl, or
(f) N(CH$_2$CH$_2$)$_2$Q,
R$^{24}$ is:
(a) $(C_1-C_4)$-alkyl,
(b) CHR$^{25}$—O—COR$^{26}$,
(c) CH$_2$CH$_2$—N[$(C_1-C_2)$-alkyl]$_2$,
(d) CH$_2$CH$_2$—N[CH$_2$CH$_2$]$_2$O,
(e) (CH$_2$CH$_2$O)$_y$—O—[$(C_1-C_4)$-alkyl], wherein y is 1 or 2,
(f) aryl or CH$_2$-aryl, where aryl is as defined above or optionally substituted with CO$_2$($C_1-C_4$)-alkyl,

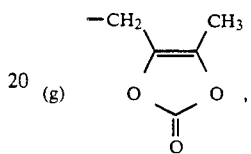
(g)

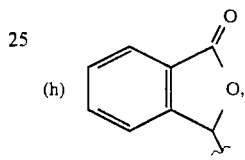
(h)

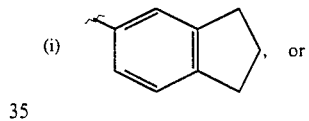
(i) , or

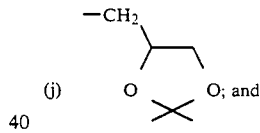
(j) ; and

R$^{25}$ and R$^{26}$ independently are $(C_1-C_6)$-alkyl or phenyl.
Wherein another embodiment is when:
R$^1$ is:
(a) $(C_1-C_6)$-alkyl or $(C_2-C_6)$-alkenyl or $(C_2-C_6)$-alkynyl each of which is unsubstituted or substituted with a substituent selected from the group consisting of:
  i) $(C_1-C_4)$-alkylthio,
  ii) $(C_1-C_4)$-alkoxy,
  iii) CF$_3$,
  iv) CF$_2$CF$_3$, or
  v) $(C_3-C_5)$-cycloalkyl,
(b) $(C_1-C_4)$-perfluoroalkyl, or
(c) $(C_3-C_5)$-cycloalkyl; and
E is:
(a) single bond,
(b) —S—, or
(c) —O—; and
n is 0, 1, or 2; and
J$^1$ is (a) —C(=M)—, (b) J$^1$ and L are connected together to form a 6-carbon aromatic ring substituted with R$^{7a}$, R$^{7b}$, R$^{8a}$ and R$^{8b}$ or (c) J$^1$ and L are connected together to form a 6-membered aromatic ring having one nitrogen atom not at J$^1$, substituted with R$^{7a}$, R$^{7b}$, R$^{8a}$ and R$^{8b}$; and
K$^1$ is (a) —C(=M)—, or (b) K$^1$ and L are connected together to form a 6-carbon aromatic ring substituted with $R^{7a}$, $R^{7b}$, $R^{8a}$ and $R^{8b}$, or (c) $K^1$ and L are connected together to form a six-membered aromatic ring having one nitrogen atom substituted with $R^{7a}$, $R^{7b}$ and $R^{8a}$ provided that one and only one of $J^1$ and $K^1$ is —C(=M)—; and one of $a^1$ or $b^1$ is a double bond in structure Ia provided that when $J^1$ is —C(=M)— then $b^1$ is a double bond and when $K^1$ is —C(=M)— then $a^1$ is a double bond;

L is the point of attachment of the 6-membered fused aromatic ring optionally having one nitrogen atom; and $J^2$ is (a) —C(=M)—, or (b) —C($R^{17}$)—; and $K^2$ is (a) —C(=M)—, or (b) —C($R^{17}$)—, provided that one and only one of $J^2$ and $K^2$ is —C(=M)—; and one of $a^2$ or $b^2$ is a double bond in structure Ic provided that when $J^2$ is —C(=M)— then $b^2$ is a double bond and when $K^2$ is —C(=M)— then $a^2$ is a double bond;

M is O, S or $NR^{15}$; and $R^2$ is:
- (a) H,
- (b) ($C_1$-$C_6$)-alkyl; and $R^{2a}$ is:
- (a) $R^2$,
- (b) $CH_2$aryl, or
- (c) aryl; and $R^{7a}$ and $R^{7b}$ are independently
- (a) H,
- (b) ($C_1$-$C_6$)-alkyl, ($C_2$-$C_6$)-alkenyl or ($C_2$-$C_6$)-alkynyl,
- (c) Cl, Br, I, F,
- (d) $CF_3$, or
- (e) when $R^{7a}$ and $R^{7b}$ are bonded to adjacent carbon atoms, they can be joined to form a phenyl ring;

$R^{8a}$ and $R^{8b}$ are independently
- (a) H,
- (b) aryl-($C_1$-$C_4$)-alkyl,
- (c) heteroaryl-($C_1$-$C_4$)-alkyl,
- (d) ($C_1$-$C_6$)-alkyl, is unsubstituted or substituted with a substituent selected from the group consisting of: —CON($R^{2a}$)$_2$, -heteroaryl, —S(O)$_x$—$R^{21}$, -tetrazol-5-yl, —CONHSO$_2R^{21}$, —SO$_2$NH-heteroaryl, —SO$_2$NHCOR$^{21}$, —PO(OR$^2$)$_2$, —PO(OR$^{2a}$)$_2$, —SO$_2$NH—CN, —NR$^2$COOR$^{21}$, —OH, —NH$_2$, guanidino, ($C_1$-$C_4$)-alkoxy, ($C_1$-$C_4$)-alkylthio, ($C_1$-$C_4$)-alkylamino, ($C_1$-$C_4$)-dialkylamino, —COOR$^{2a}$, —CONHR$^{2a}$, —O—COR$^{2a}$, or aryl,
- (e) —CO-aryl,
- (f) ($C_3$-$C_7$)-cycloalkyl,
- (g) Cl, Br, I, F,
- (h) —OH,
- (i) —OR$^{21}$,
- (j) —SH,
- (k) —S(O)$_n$—($C_1$-$C_4$)-alkyl,
- (l) —COR$^{2a}$,
- (m) —CO$_2$H,
- (n) —CO$_2$—($C_1$-$C_4$)-alkyl,
- (o) —SO$_3$H,
- (p) —NR$^2$R$^{21}$,
- (q) —NR$^2$COR$^{21}$,
- (r) —NR$^2$COOR$^{21}$,
- (s) —SO$_2$NR$^{2a}$,
- (t) —SO$_2$NR$^2$R$^{2a}$,
- (u) —NO$_2$,
- (v) —NHSO$_2$CF$_3$,
- (w) —CONR$^{2a}$R$^{2a}$,
- (x) —($C_1$-$C_4$)-perfluoroalkyl,
- (y) —COOR$^2$,
- (z) —SO$_3$H,
- (aa) —N(R$^2$)SO$_2$R$^{21}$,
- (bb) —NR$^2$CONR$^{2a}$R$^{21}$,
- (cc) —OC(=O)NR$^{21}$R$^{2a}$,
- (dd) -aryl,
- (ee) —NHSO$_2$CF$_3$,
- (ff) —SO$_2$NH-heteroaryl,
- (gg) —SO$_2$NHCOR$^{21}$,
- (hh) —CONHSO$_2$R$^{21}$,
- (ii) —PO(OR$^2$)$_2$,
- (jj) -tetrazol-5-yl,
- (kk) —CONH(tetrazol-5-yl),
- (ll) —SO$_2$NHCN, or
- (mm) -heteroaryl; and $R^9$ and $R^{10}$ are independently:
- (a) H,
- (b) ($C_1$-$C_6$)-alkyl, unsubstituted or substituted with ($C_3$-$C_7$)-cycloalkyl,
- (c) ($C_2$-$C_6$)-alkenyl,
- (d) ($C_2$-$C_6$)-alkynyl,
- (e) Cl, Br, F, I,
- (f) ($C_1$-$C_6$)-alkoxy,
- (g) when $R^9$ and $R^{10}$ are on adjacent carbons, they can be joined to form a phenyl ring,
- (h) ($C_1$-$C_6$)-perfluoroalkyl,
- (i) ($C_3$-$C_7$)-cycloalkyl, unsubstituted or substituted with ($C_1$-$C_6$)-alkyl,
- (j) aryl,
- (k) ($C_1$-$C_6$)-alkyl-S(O)$_n$—(CH$_2$)$_n$—,
- (l) hydroxy-($C_1$-$C_6$)-alkyl,
- (m) —CF$_3$,
- (n) —CO$_2$R$^{2a}$,
- (o) —OH,
- (p) —NR$^2$R$^{21}$,
- (q) -[($C_1$-$C_6$)-alkyl]NR$^2$R$^{21}$,
- (r) —NO$_2$,
- (s) —(CH$_2$)$_n$—SO$_2$—N(R$^2$)$_2$,
- (t) —NR$^2$CO—($C_1$-$C_4$)-alkyl, or
- (u) —CON(R$^2$)$_2$; and X is:
- (a) —O—,
- (b) —S(O)$_n$—,
- (c) —NR$^{13}$—
- (d) —CH$_2$O—,
- (e) —CH$_2$S(O)$_n$,
- (f) —CH$_2$NR$^{13}$—,
- (g) —OCH$_2$—,
- (h) —NR$^{13}$CH$_2$—,
- (i) —S(O)$_n$CH$_2$—,
- (j) —CH$_2$—,
- (k) —(CH$_2$)$_2$—,
- (l) single bond, or
- (m) —CH=, wherein Y and $R^{12}$ are absent forming a —C=C— bridge to the carbon bearing Z and $R^{11}$; and Y is:
- (a) single bond,
- (b) —O—,
- (c) —S(O)n—,
- (d) —NR$^{13}$—, or
- (e) —CH$_2$—; and except that X and Y are not defined in such a way that the carbon atom to which Z is attached also simultaneously is bonded to two heteroatoms (O, N, S, SO, SO$_2$);

$R^{11}$ and $R^{12}$ are independently:
- (a) H,
- (b) ($C_1$-$C_6$)-alkyl, unsubstituted or substituted with a substituent selected from the group consisting of:

(i) aryl,
(ii) $(C_3-C_7)$-cycloalkyl,
(iii) $NR^2R^{21}$,
(iv) morpholin-4-yl,
(v) OH,
(vi) $CO_2R^{2a}$, or
(vii) $CON(R^2)_2$,
(c) aryl or aryl-$(C_1-C_2)$-alkyl, unsubstituted or substituted with 1 to 3 substituents selected from the group consisting of:
(i) Cl, Br, I, F,
(ii) $(C_1-C_6)$-alkyl,
(iii) $[(C_1-C_5)$-alkenyl]$CH_2-$,
(iv) $[(C_1-C_5)$-alkynyl]$CH_2-$,
(v) $(C_1-C_6)$-alkyl-$S(O)_n-(CH_2)_n-$,
(vi) $-CF_3$,
(vii) $-CO_2R^{2a}$,
(viii) $-OH$,
(ix) $-NR^2R^{21}$,
(x) $-NO_2$,
(xi) $-NR^2COR^2$,
(xii) $-CON(R^2)_2$,
(xiii) $-G-[(C_1-C_6)$-alkyl$]-R^{23}$,
(xiv) $-N[CH_2CH_2]_2Q$, or
(xv) $-P(O)[O-(C_1-C_4)$-alkyl$]_2$,
and can additionally be substituted with 1 or 2 substituents selected from the group consisting of: Br, Cl or F,
(d) $(C_3-C_7)$-cycloalkyl, or
(e) when Y is single bond, $R^{11}$ and $R^{12}$ can be joined to form a ring of 5 to 7 carbon atoms, the ring can be benzo-fused and one carbon of which can be replaced with a heteroatom selected from the group consisting of: O, $S(O)_x$ and $NR^{22}$; and
G is: a single bond, O, $S(O)_x$ or $NR^{23}$; and
Q is: O, $S(O)_x$ or $NR^{22}$; and
$R^{13}$ is:
(a) H,
(b) $(C_1-C_6)$-alkyl,
(c) aryl,
(d) aryl-$(C_1-C_6)$-alkyl-$(C=O)-$,
(e) $(C_1-C_6)$-alkyl-$(C=O)-$,
(f) $[(C_2-C_5)$-alkenyl]$CH_2-$,
(g) $[(C_2-C_5)$-alkynyl]$CH_2-$, or
(h) aryl-$CH_2-$; and
Z is:
(a) $-CO_2H$,
(b) $-CO_2R^{24}$,
(c) -tetrazol-5-yl,
(d) $-CONH$(tetrazol-5-yl)
(e) $-CONHSO_2$-aryl,
(f) $-CONHSO_2-(C_1-C_8)$-alkyl, wherein the alkyl group is unsubstituted or substituted with a substituent selected from the group consisting of: $-OH$, $-SH$, $-O(C_1-C_4)$-alkyl, $-S-(C_1-C_4)$-alkyl, $-CF_3$, Cl, Br, F, I, $-NO_2$, $-CO_2H$, $-CO_2-(C_1-C_4)$-alkyl, $-NH_2$, $-NH[(C_1-C_4)$-alkyl], $-N[(C_1-C_4)$-alkyl]$_2$; and
(g) $-CONHSO_2-(C_1-C_4)$-perfluoroalkyl,
(h) $-CONHSO_2$-heteroaryl,
(i) $-CONHSO_2NR^{2a}R^{2a}$,
(j) $-SO_2NHCO$-aryl,
(k) $-SO_2NHCO-(C_1-C_8)$-alkyl, wherein the alkyl group is unsubstituted or substituted with a substituent selected from the group consisting of: $-OH$, $-SH$, $-O(C_1-C_4)$-alkyl, $-S-(C_1-C_4)$-alkyl, $-CF_3$, Cl, Br, F, I, $-NO_2$, $-CO_2H$, $-CO_2-(C_1-C_4)$-alkyl, $-NH_2$, $-NH[(C_1-C_4)$-alkyl], $-N[(C_1-C_4)$-alkyl]$_2$; and
(l) $-SO_2NHCO-(C_1-C_4)$-perfluoroalkyl,
(m) $-SO_2NHCO$-heteroaryl, or
(n) $-SO_2NHCONR^{2a}R^{2a}$; and
$R^{15}$ is:
(a) H,
(b) aryl, is unsubstituted or substituted with 1 or 2 substituents selected from the group consisting of Cl, Br, I, F, $-O-(C_1-C_4)$-alkyl, $(C_1-C_4)$-alkyl, $-NO_2$, $-CF_3$, $-SO_2NR^2R^{2a}$, $-S-(C_1-C_4)$-alkyl, $-OH$, $-NH_2$, $(C_3-C_7)$-cycloalkyl, $(C_3-C_{10})$-alkenyl;
(c) $(C_1-C_6)$-alkyl, $(C_2-C_6)$-alkenyl or $(C_2-C_6)$-alkynyl each of which is unsubstituted or substituted with one or more substituents selected from the group consisting of: aryl, $(C_3-C_7)$-cycloalkyl, Cl, Br, I, F, $-OH$, $-NH_2$, $-NH[(C_1-C_4)$-alkyl], Br, I, F, $-OH$, $-NH_2$, $-NH[(C_1-C_4)$-alkyl], $-N[(C_1-C_4)$-alkyl]$_2$, $-NH-SO_2R^{2a}$, $-COOR^{2a}$, $-SO_2NHR^{2a}$; or
(d) an unsubstituted, monosubstituted or disubstituted aromatic 5 or 6 membered ring which have one or two heteroatoms selected from the group consisting of N, O, S, and wherein the substituents are members selected from the group consisting of $-OH$, $-SH$, $(C_1-C_4)$-alkyl, $(C_1-C_4)$-alkyloxy $-CF_3$, Cl, Br, I, F, or $NO_{2l}$; and
$R^{16}$ is:
(a) $(C_1-C_{10})$-alkyl,
(b) substituted $(C_1-C_{10})$-alkyl in which one or two substituent(s) is (are) selected from:
(1) hydroxy,
(2) $(C_1-C_5)$-alkoxy,
(3) $(C_1-C_5)$-alkoxycarbonyl,
(4) phenyl,
(5) carboxy,
(6) $C(=O)NH-(C_1-C_5)$-alkyl,
(c) aryl, or
(d) aryl substituted with V and W; and
V and W are selected from:
(a) H,
(b) $(C_1-C_5)$-alkoxy,
(c) $(C_1-C_5)$-alkyl,
(d) hydroxy,
(e) $-CN$,
(f) $-NO_2$,
(g) $-NR^2R^{2a}$,
(h) $-CO_2R^{2a}$,
(i) $-CF_3$,
(j) I, Br, Cl, F,
(k) hydroxy-$(C_1-C_4)$-alkyl-,
(l) tetrazol-5-yl,
(m) $-NHSO_2CF_3$,
(n) -$[(C_1-C_4)$-alkyl]$NR^2R^{21}$,
(o) -$[(C_1-C_4)$-alkyl]$NR^2COR^{21}$,
(p) -$[(C_1-C_4)$-alkyl]$NR^2COOR^{21}$,
(q) -$[(C_1-C_4)$-alkyl]$CONR^{2a}R^{2a}$,
(r) -$[(C_1-C_4)$-alkyl]$N(R^2)SO_2R^{21}$,
(s) -$[(C_1-C_4)$-alkyl]$NR^2CONR^4R^{21}$, or
(t) -$[(C_1-C_4)$-alkyl]$OC(=O)NR^{21}R^{2a}$; and
$R^{17}$ and $R^{18}$ are independently:
(a) H,
(b) aryl-$(C_1-C_4)$-alkyl-,
(c) heteroaryl-$(C_1-C_4)$-alkyl-,
(d) $(C_1-C_4)$-alkyl, unsubstituted or substituted with a substituent selected from the group consisting of:

—OH, —NH$_2$, guanidino, (C$_1$-C$_4$)-alkoxy, (C$_1$-C$_4$)-alkylthio, (C$_1$-C$_4$)-alkylamino, (C$_1$-C$_4$)-dialkylamino, —COOR$^{2a}$, —CONHR$^{2a}$, or —O—COR$^{2a}$, CF$_3$,
- (e) (C$_1$-C$_4$)-alkenyl,
- (f) —CO—aryl,
- (g) (C$_3$-C$_7$)-cycloalkyl,
- (h) Cl, Br, I, F,
- (i) —OH,
- (j) —O—(C$_1$-C$_4$)-alkyl,
- (k) —(C$_1$-C$_4$)-perfluoroalkyl,
- (l) —SH,
- (m) —S(O)$_n$—(C$_1$-C$_4$)-alkyl,
- (n) —CHO,
- (o) —CO$_2$R$^{2a}$,
- (p) —SO$_3$H,
- (q) —NH$_2$,
- (r) —NH[(C$_1$-C$_4$)-alkyl],
- (s) —N[(C$_1$-C$_4$)-alkyl]$_2$,
- (t) —NHCO$_2$—(C$_1$-C$_4$)-alkyl,
- (u) —SO$_2$NR$^2$R$^{2a}$,
- (v) —CH$_2$OCOR$^{2a}$,
- (w) —NHSO$_2$—(C$_1$-C$_4$)-alkyl,
- (x) 5 or 6 membered saturated heterocycle having one nitrogen atom and optionally having one other heteroatom selected from N, O, or S wherein the 5- or 6- membered saturated heterocycle is selected from the group consisting of: pyrrolidine, morpholine, or piperazine,
- (y) aryl,
- (z) heteroaryl, wherein heteroaryl is a 5 or 6 membered aromatic ring having one or two heteroatoms selected from the group consisting of O, N, or S; and
- (aa) tetrazol-5-yl, or
- (bb) -[(C$_1$-C$_4$)-alkyl]NR$^2$R$^{21}$,
- (cc) -[(C$_1$-C$_4$)-alkyl]NR$^2$COR$^{21}$,
- (dd) -[(C$_1$-C$_4$)-alkyl]NR$^2$COOR$^{21}$,
- (ee) -[(C$_1$-C$_4$)-alkyl]CONR$^{2a}$R$^{2a}$,
- (ff) -[(C$_1$-C$_4$)-alkyl]N(R$^2$)SO$_2$R$^{21}$,
- (gg) -[(C$_1$-C$_4$)-alkyl]NR$^2$CONR$^4$R$^{21}$, or
- (hh) -[(C$_1$-C$_4$)-alkyl]OC(=O)NR$^{21}$R$^{2a}$; and R$^{21}$ is:
- (a) aryl, or
- (b) (C$_1$-C$_4$)-alkyl which is unsubstituted or substituted with:
  - i) NH$_2$,
  - ii) NH[(C$_1$-C$_4$)-alkyl],
  - iii) N[(C$_1$-C$_4$)-alkyl]$_2$,
  - iv) CO$_2$H,
  - v) CO$_2$(C$_1$-C$_4$)-alkyl,
  - vi) OH,
  - vii) SO$_3$H, or
  - viii) SO$_2$NH$_2$; and R$^{22}$ is:
- (a) H,
- (b) (C$_1$-C$_4$)-alkyl,
- (c) (C$_1$-C$_4$)-alkoxyl,
- (d) aryl,
- (e) aryl-(C$_1$-C$_4$)-alkyl,
- (f) CO$_2$R$^{2a}$,
- (g) CON(R$^2$)$_2$,
- (h) SO$_2$R$^{2a}$,
- (i) SO$_2$N(R$^2$)$_2$,
- (j) P(O)[(C$_1$-C$_4$)-alkoxyl]$_2$, or
- (k) imidazol-2-yl or imidazol-4-yl, in which the imidazolyl can be substituted with (C$_1$-C$_4$)-alkyl; and R$^{23}$ is:
- (a) OH,
- (b) NR$^2$R$^{21}$,
- (c) CO$_2$R$^{2a}$,
- (d) CON(R$^2$)$_2$,
- (e) S(O)$_x$—(C$_1$-C$_4$)-alkyl, or
- (f) N[CH$_2$CH$_2$]$_2$Q; and R$^{24}$ is:
- (a) (C$_1$-C$_4$)-alkyl,
- (b) CHR$^{25}$—O—COR$^{26}$,
- (c) CH$_2$CH$_2$—N[(C$_1$-C$_2$)-alkyl]$_2$,
- (d) CH$_2$CH$_2$—N[CH$_2$CH$_2$]$_2$O,
- (e) (CH$_2$CH$_2$O)$_y$—O—[(C$_1$-C$_4$)-alkyl], wherein y is 1 or 2,
- (f) aryl or CH$_2$-aryl, where aryl is as defined above or optionally substituted with CO$_2$(C$_1$-C$_4$)-alkyl,

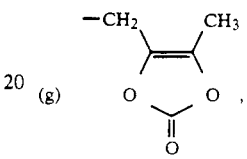

(g)

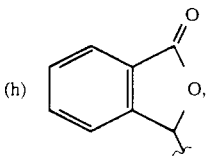

(h)

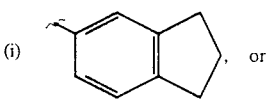

(i) , or

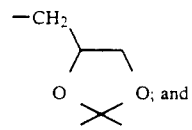

(j) ; and

R$^{25}$ and R$^{26}$ independently are (C$_1$-C$_6$)-alkyl or phenyl

Wherein yet another embodiment of the invention is when:

R$^1$ is:
- (a) (C$_1$-C$_6$)-alkyl (C$_2$-C$_6$)-alkenyl or (C$_2$-C$_6$)-alkynyl each of which is unsubstituted or substituted with a substituent selected from the group consisting of:
  - i) (C$_1$-C$_4$)-alkylthio,
  - ii) (C$_1$-C$_4$)-alkoxy,
  - iii) CF$_3$,
  - iv) CF$_2$CF$_3$, or
  - v) (C$_3$-C$_5$)-cycloalkyl, or
- (b) (C$_1$-C$_4$)-perfluoroalkyl; and E is a single bond; and n is 0 to 2; and J$^1$ and L are connected together to form a 6-carbon aromatic ring substituted with R$^{7a}$, R$^{7b}$, R$^{8a}$ and R$^{8b}$; or J$^1$ and L are connected together to form a 6-membered aromatic ring having one nitrogen atom not at J$^1$, substituted with R$^{7a}$, R$^{7b}$, R$^{8a}$ and R$^{8b}$; and K$^1$ is —C(=M)—; and a$^1$ is a double bond; and L is the point of attachment of the 6-membered fused aromatic ring optionally having one nitrogen atom; and J$^2$ is —C(R$^{17}$)—; and K$^2$ is —C(=M)—; and $a^2$ is a double bond; and
M is O, or $NR^{15}$; and
$R^2$ is:
 (a) H,
 (b) $(C_1-C_6)$-alkyl, or
 (c) $(C_1-C_6)$-alkyl; and
$R^{2a}$ is:
 (a) $R^2$,
 (b) benzyl, or
 (c) phenyl; and
$R^{7a}$ and $R^{7b}$ are independently
 (a) H,
 (b) $(C_1-C_6)$-alkyl, $(C_2-C_6)$-alkenyl or $(C_2-C_6)$-alkynyl,
 (c) Cl, Br, I, F,
 (d) $CF_3$, or
 (e) when $R^{7a}$ and $R^{7b}$ are bonded to adjacent carbon atoms, they can be joined to form a phenyl ring;
$R^{8a}$ and $R^{8b}$ are independently
 (a) H,
 (b) aryl-$(C_1-C_4)$-alkyl,
 (c) heteroaryl-$(C_1-C_4)$-alkyl,
 (d) $(C_1-C_6)$-alkyl, unsubstituted or substituted with a substituent selected from the group consisting of: —$CON(R^{2a})_2$, -heteroaryl, —$S(O)_n$—$R^{21}$, -tetrazol-5-yl, —$CONHSO_2R^{21}$, —$SO_2NH$-heteroaryl, —$SO_2NHCOR^{21}$, —$PO(OR^2)_2$, —$PO(OR^{2a})_2$, —$SO_2NH$—CN, —$NR^2COOR^{21}$, —OH, —$NH_2$, guanidino, $(C_1-C_4)$-alkoxy, $(C_1-C_4)$-alkylthio, $(C_1-C_4)$-alkylamino, $(C_1-C_4)$-dialkylamino, —$COOR^{2a}$, —$CONHR^{2a}$, —O—$COR^{2a}$, or aryl,
 (e) —CO—aryl,
 (f) $(C_3-C_7)$-cycloalkyl,
 (g) Cl, Br, I, F,
 (h) —OH,
 (i) —$OR^{21}$,
 (j) —SH,
 (k) —$S(O)_n$—$(C_1-C_4)$-alkyl,
 (l) —$COR^{2a}$,
 (m) —$CO_2H$,
 (n) —$CO_2$—$(C_1-C_4)$-alkyl,
 (o) —$SO_3H$,
 (p) —$NR^2R^{21}$,
 (q) —$NR^2COR^{21}$,
 (r) —$NR^2COOR^{21}$,
 (s) —$SO_2NR^{2a}$,
 (t) —$SO_2NR^2R^{2a}$,
 (u) —$NO_2$,
 (v) —$NHSO_2CF_3$,
 (w) —$CONR^{2a}R^{2a}$,
 (x) —$(C_1-C_4)$-perfluoroalkyl,
 (y) —$COOR^2$,
 (z) —$SO_3H$,
 (aa) —$N(R^2)SO_2R^{21}$,
 (bb) —$NR^2CONR^4R^{21}$,
 (cc) —$OC(=O)NR^{21}R^{2a}$,
 (dd) —aryl,
 (ee) —$NHSO_2CF_3$,
 (ff) —$SO_2NH$-heteroaryl,
 (gg) —$SO_2NHCOR^{21}$,
 (hh) —$CONHSO_2R^{21}$,
 (ii) —$PO(OR^2)_2$,
 (jj) —tetrazol-5-yl,
 (kk) —CONH(tetrazol-5-yl),
 (ll) —$SO_2NHCN$, or
 (mm) —heteroaryl; and
$R^9$ and $R^{10}$ are independently:
 (a) H,
 (b) $(C_1-C_6)$-alkyl, unsubstituted or substituted with $(C_3-C_7)$-cycloalkyl,
 (c) $(C_2-C_6)$-alkenyl,
 (d) $(C_2-C_6)$-alkynyl,
 (e) Cl, Br, F, I,
 (f) $(C_1-C_6)$-alkoxy,
 (g) when $R^9$ and $R^{10}$ are on adjacent carbons, they can be joined to form a phenyl ring,
 (h) $(C_1-C_6)$-perfluoroalkyl,
 (i) $(C_3-C_7)$-cycloalkyl, unsubstituted or substituted with $(C_1-C_6)$-alkyl,
 (j) aryl; and
X is:
 (a) —O—,
 (b) —$S(O)_n$—,
 (c) —$NR^{13}$—
 (d) —$CH_2O$—,
 (e) —$CH_2S(O)_n$,
 (f) —$CH_2NR^{13}$—,
 (g) —$OCH_2$—,
 (h) —$NR^{13}CH_2$—,
 (i) —$S(O)_nCH_2$—,
 (j) —$CH_2$—,
 (k) —$(CH_2)_2$—,
 (l) single bond, or
 (m) —CH=, wherein Y and $R^{12}$ are absent forming a —C=C— bridge to the carbon bearing Z and $R^{11}$; and
Y is:
 (a) single bond,
 (b) —O—,
 (c) —$S(O)n$—,
 (d) —$NR^{13}$—, or
 (e) —$CH_2$—; and
except that X and Y are not defined in such a way that the carbon atom to which Z is attached also simultaneously is bonded to two heteroatoms (O, N, S, SO, $SO_2$);
$R^{11}$ and $R^{12}$ are independently:
 (a) H,
 (b) $(C_1-C_6)$-alkyl, unsubstituted or substituted with a substituent selected from the group consisting of:
  (i) aryl,
  (ii) $(C_3-C_7)$-cycloalkyl,
  (iii) $NR^2R^{21}$,
  (iv) morpholin-4-yl,
  (v) OH,
  (vi) $CO_2R^{2a}$, or
  (vii) $CON(R^2)_2$,
 (c) aryl or aryl-$(C_1-C_2)$-alkyl, unsubstituted or substituted with 1 to 3 substitutents selected from the group consisting of:
  (i) Cl, Br, I, F,
  (ii) $(C_1-C_6)$-alkyl,
  (iii) [$(C_1-C_5)$-alkenyl]$CH_2$—,
  (iv) [$(C_1-C_5)$-alkynyl]$CH_2$—,
  (v) $(C_1-C_6)$-alkyl-$S(O)_n$—$(CH_2)_n$—,
  (vi) —$CF_3$,
  (vii) —$CO_2R^{2a}$,
  (viii) —OH,
  (ix) —$NR^2R^{21}$,
  (x) —$NO_2$,
  (xi) —$NR^2COR^2$,
  (xii) —$CON(R^2)_2$,
  (xiii) —G—[$(C_1-C_6)$-alkyl]-$R^{23}$,
  (xiv) —$N[CH_2CH_2]_2Q$, or
  (xv) —$P(O)[O$—$(C_1-C_4)$-alkyl]$_2$, and can additionally be substituted with 1 or 2 substituents selected from the group consisting of: Br, Cl or F, (d) $(C_3-C_7)$-cycloalkyl, or (e) when Y is single bond, $R^{11}$ and $R^{12}$ can be joined to form a ring of 5 to 7 carbon atoms, the ring can be benzo-fused and one carbon of which can be replaced with a heteroatom selected from the group consisting of: O, $S(O)_x$ and $NR^{22}$; and G is: a single bond, O, $S(O)_x$ or $NR^{23}$; and Q is: O, $S(O)_x$ or $NR^{22}$; and $R^{13}$ is:
(a) H,
(b) $(C_1-C_6)$-alkyl,
(c) aryl,
(d) aryl-$(C_1-C_6)$-alkyl-(C=O)—,
(e) $(C_1-C_6)$-alkyl-(C=O)—,
(f) [$(C_2-C_5)$-alkenyl]$CH_2$—,
(g) [$(C_2-C_5)$-alkynyl]$CH_2$—, or
(h) aryl-$CH_2$—; and Z is:
(a) —$CO_2H$,
(b) —$CO_2R^{24}$,
(c) -tetrazol-5-yl,
(d) —CONH(tetrazol-5-yl)
(e) —$CONHSO_2$-aryl,
(f) —$CONHSO_2$-$(C_1-C_8)$-alkyl, wherein the alkyl group is unsubstituted or substituted with a substituent selected from the group consisting of: —OH, —SH, —O$(C_1-C_4)$-alkyl, —S—$(C_1-C_4)$-alkyl, —$CF_3$, Cl, Br, F, I, —$NO_2$, —$CO_2H$, —$CO_2$—$(C_1-C_4)$-alkyl, —$NH_2$, —NH[$(C_1-C_4)$-alkyl], —N[$(C_1-C_4)$-alkyl]$_2$; and
(g) —$CONHSO_2$—$(C_1-C_4)$-perfluoroalkyl,
(h) —$CONHSO_2$-heteroaryl,
(i) —$CONHSO_2NR^{2a}R^{2a}$,
(j) —$SO_2NHCO$-aryl,
(k) —$SO_2NHCO$—$(C_1-C_8)$-alkyl, wherein the alkyl group is unsubstituted or substituted with a substituent selected from the group consisting of: —OH, —SH, —O$(C_1-C_4)$-alkyl, —S—$(C_1-C_4)$-alkyl, —$CF_3$, Cl, Br, F, I, —$NO_2$, —$CO_2H$, —$CO_2$—$(C_1-C_4)$-alkyl, —$NH_2$, —NH[$(C_1-C_4)$-alkyl], —N[$(C_1-C_4)$-alkyl]$_2$; and
(l) —$SO_2NHCO$—$(C_1-C_4)$-perfluoroalkyl,
(m) —$SO_2NHCO$-heteroaryl, or
(n) —$SO_2NHCONR^{2a}R^{2a}$; and $R^{15}$ is:
(a) H,
(b) aryl, unsubstituted or substituted with 1 or 2 substituents selected from the group consisting of: Cl, Br, I, F —O—$(C_1-C_4)$-alkyl, $(C_1-C_4)$-alkyl, —$NO_2$, —$CF_3$, —$SO_2NR^2R^{2a}$, —S—$(C_1-C_4)$-alkyl, —OH, —$NH_2$, $(C_3-C_7)$-cycloalkyl, $(C_3-C_{10})$-alkenyl
(c) $(C_1-C_6)$-alkyl, $(C_2-C_6)$-alkenyl or $(C_2-C_6)$-alkynyl each of which is unsubstituted or substituted with one or more substituents selected from the group consisting of aryl as defined above, $(C_3-C_7)$-cycloalkyl, Cl, Br, I, F, —OH, —$NH_2$, —NH[$(C_1-C_4)$-alkyl], —N[$(C_1-C_4)$-alkyl]$_2$, —NH—$SO_2R^{2a}$, —$COOR^{2a}$, —$SO_2NHR^{2a}$; or
(d) an unsubstituted, monosubstituted or disubstituted aromatic 5 or 6 membered ring which have one or two heteroatoms selected from the group consisting of N, O, S, and wherein the substituents are members selected from the group consisting of:
—OH, —SH, $(C_1-C_4)$-alkyl, $(C_1-C_4)$-alkyloxy —$CF_3$, Cl, Br, I, F, or $NO_2$; and $R^{16}$ is
(a) $(C_1-C_{10})$-alkyl;
(b) substituted $(C_1-C_{10})$-alkyl in which one or more substituent(s) is selected from
(1) hydroxy,
(2) $(C_1-C_5)$-alkoxy,
(3) $(C_1-C_5)$-alkoxycarbonyl,
(4) phenyl,
(5) carboxy,
(6) C(=O)NH—$(C_1-C_5)$-alkyl,
(c) aryl, or
(d) aryl substituted with V and W; and V and W are selected from:
(a) H,
(b) $(C_1-C_5)$-alkoxy,
(c) $(C_1-C_5)$-alkyl,
(d) hydroxy,
(e) —CN,
(f) —$NO_2$,
(g) —$NR^2R^{2a}$,
(h) —$CO_2R^{2a}$,
(i) —$CF_3$,
(j) I, Br, Cl, F,
(k) hydroxy-$(C_1-C_4)$-alkyl-,
(l) -1H-tetrazol-5-yl, or
(m) —$NHSO_2CF_3$; and $R^{17}$ and $R^{18}$ are independently
(a) H,
(b) aryl-$(C_1-C_4)$-alkyl-,
(c) heteroaryl-$(C_1-C_4)$-alkyl-,
(d) $(C_1-C_4)$-alkyl, unsubstituted or substituted with a substituent selected from the group consisting of: —OH, —$NH_2$, guanidino, $(C_1-C_4)$-alkoxy, $(C_1-C_4)$-alkylthio, $(C_1-C_4)$-alkylamino, $(C_1-C_4)$-dialkylamino, —$COOR^{2a}$, —$CONHR^{2a}$, —O—$COR^{2a}$ or $CF_3$,
(e) $(C_1-C_4)$-alkenyl,
(f) —CO-aryl,
(g) $(C_3-C_7)$-cycloalkyl,
(h) Cl, Br, I, F,
(i) —OH,
(j) —O—$(C_1-C_4)$-alkyl,
(k) —$(C_1-C_4)$-perfluoroalkyl,
(l) —SH,
(m) —$S(O)_n$—$(C_1-C_4)$-alkyl,
(n) —CHO,
(o) —$CO_2R^{2a}$
(p) —$SO_3H$,
(q) —$NH_2$,
(r) —NH[$(C_1-C_4)$-alkyl],
(s) —N[$(C_1-C_4)$-alkyl]$_2$,
(t) —$NHCO_2$—$(C_1-C_4)$-alkyl,
(u) —$SO_2NR^{2a}$,
(v) —$CH_2OCOR^{2a}$,
(w) —$NHSO_2$—$(C_1-C_4)$-alkyl,
(x) 5 or 6 membered saturated heterocycle having one nitrogen atom and optionally having one other heteroatom selected from N, O, or S, wherein the 5 or 6 membered saturated heterocycle is selected from the group consisting of: pyrrolidine, morpholine, or piperazine,
(y) aryl,
(z) heteroaryl, or
(aa) tetrazol-5-yl; and $R^{21}$ is:
(a) aryl, or (b) ($C_1$-$C_4$)-alkyl which is unsubstituted or substituted with:
 i) $NH_2$,
 ii) $NH[(C_1$-$C_4)$-alkyl],
 iii) $N[(C_1$-$C_4)$-alkyl]$_2$,
 iv) $CO_2H$,
 v) $CO_2(C_1$-$C_4)$-alkyl,
 vi) OH,
 vii) $SO_3H$, or
 viii) $SO_2NH_2$; and $R^{22}$ is:
 (a) H,
 (b) ($C_1$-$C_4$)-alkyl,
 (c) ($C_1$-$C_4$)-alkoxyl,
 (d) aryl,
 (e) aryl-($C_1$-$C_4$)-alkyl,
 (f) $CO_2R^{2a}$,
 (g) $CON(R^2)_2$,
 (h) $SO_2R^{2a}$,
 (i) $SO_2N(R^2)_2$,
 (j) $P(O)[(C_1$-$C_4)$-alkoxyl]$_2$, or
 (k) imidazol-2-yl or imidazol-4-yl, in which the imidazolyl can be substituted with ($C_1$-$C_4$)-alkyl; and $R^{23}$ is:
 (a) OH,
 (b) $NR^2R^{21}$,
 (c) $CO_2R^{2a}$,
 (d) $CON(R^2)_2$,
 (e) $S(O)_x$—($C_1$-$C_4$)-alkyl, or
 (f) $N(CH_2CH_2)_2Q$; and $R^{24}$ is:
 (a) ($C_1$-$C_4$)-alkyl,
 (b) $CHR^{25}$—O—$COR^{26}$,
 (c) $CH_2CH_2$—$N[(C_1$-$C_2)$-alkyl]$_2$,
 (d) $CH_2CH_2$—$N[CH_2CH_2]_2O$,
 (e) $(CH_2CH_2O)_y$—O—[($C_1$-$C_4$)-alkyl], wherein y is 1 or 2,
 (f) aryl or $CH_2$-aryl, where aryl is as defined above or optionally substituted with $CO_2(C_1$-$C_4)$-alkyl, (g) 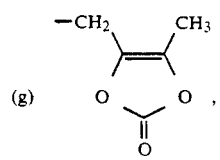

(h) 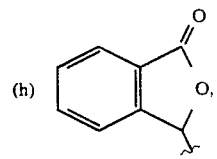

(i) 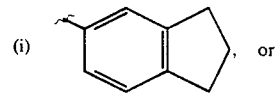, or (j) 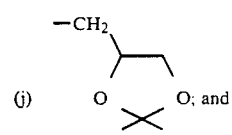; and $R^{25}$ and $R^{26}$ independently are: ($C_1$-$C_6$)-alkyl or phenyl.

The alkyl substitutents recited above denote straight and branched chain hydrocarbons of the length specified such as methyl, ethyl, isopropyl, isobutyl, neopentyl, isopentyl, etc.

The alkenyl and alkynyl substituents denote alkyl groups as described above which are modified so that each contains a carbon to carbon double bond or triple bond, respectively, such as vinyl, allyl and 2-butenyl.

Cycloalkyl denotes rings composed of 3 to 8 methylene groups, each which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl.

Preferred compounds of the present invention which are illustrative of subclasses of Formula Ia are:

QUINAZOLIN-4(3H)-ONES

3-[4-[(1-Carboxy)(1-phenyl)methoxy]phenyl]methyl-6-methyl-2-propylquinazolin-4(3H)-one 2-Butyl-3-[4-[(1-carboxy)(1-phenyl)methoxy]phenyl]methyl-6-methylquinazolin-4(3H)-one 2-Butyl-3-[4-[(1-carboxy)(1-phenyl)methoxy]phenyl]methyl-6-dimethylaminoquinazolin-4(3H)-one 2-Butyl-3-[4-[(1-carboxy)(1-phenyl)methoxy]phenyl]methyl-6-[(N-methoxycarbonyl)amino]quinazolin-4(3H)-one 2-Butyl-3-[4-[(1-carboxy)(1-phenyl)methoxy]phenyl]methyl-6-[(N-methyl)(N-methoxycarbonyl)amino]quinazolin-4(3H)-one 2-Butyl-3-[4-[(1-carboxy)(1-phenyl)methoxy]phenyl]methyl-6-[(N-methyl)(N-iso-butyloxycarbonyl)amino]quinazolin-4(3H)-one 2-Butyl-3-[4-[(1-carboxy)(1-phenyl)methoxy]phenyl]methyl-6-[(N-benzyl)(N-iso-butyloxycarbonyl)amino]quinazolin-4(3H)-one 2-Butyl-3-[4-[(1-carboxy)(1-phenyl)methoxy]phenyl]methyl-6-[(N-benzyl)(N-n-butyloxycarbonyl)amino]quinazolin-4(3H)-one 2-Butyl-3-[4-[(1-carboxy)(1-phenyl)methoxy]phenyl]methyl-6-[(N-benzyl)(N-(N-ethyl-N-methyl)aminocarbonyl)amino]quinazolin-4(3H)-one 2-Butyl-3-[4-[(1-carboxy)(1-phenyl)methoxy]phenyl]methyl-6-[(N-benzoyl)(N-n-pentyl)amino]quinazolin-4(3H)-one 2-Butyl-3-[4-[(1-carboxy)(1-phenyl)methoxy]phenyl]methyl-6-[(N-benzoyl)(N-benzyl)amino]quinazolin-4(3H)-one 2-Butyl-3-[4-[(1-carboxy)(1-phenyl)methoxy]phenyl]methyl-6-[(N-benzyl)(N-n-butyryl)amino]quinazolin-4(3H)-one 2-Butyl-3-[4-[(1-carboxy)(1-phenyl)methoxy]phenyl]methyl-6-[(N-(4-chlorobenzoyl))(N-n-pentyl)amino]quinazolin-4(3H)-one 2-Butyl-3-[4-[(1-carboxy)(1-(2-chlorophenyl))methoxy]phenyl]methyl-6-[(N-benzyl)(N-iso-butyloxycarbonyl)amino]quinazolin-4(3H)-one 2-Butyl-3-[4-[(1-carboxy)(1-(2-chlorophenyl))methoxy]phenyl]methyl-6-[(N-benzyl)(N-n-butyloxycarbonyl)amino]quinazolin-4(3H)-one 2-Butyl-3-[4-[(1-carboxy)(1-(2-chlorophenyl))methoxy]phenyl]methyl-6-[(N-benzyl)(N-(N-ethyl-N-methyl)aminocarbonyl)amino]quinazolin-4(3H)-one 2-Butyl-3-[4-[(1-carboxy)(1-(2-chlorophenyl)))methoxy]phenyl]methyl-6-[(N-benzoyl)(N-n-pentyl)amino]-quinazolin-4(3H)-one 2-Butyl-3-[4-[(1-carboxy)(1-(2-chlorophenyl)))methoxy]phenyl]methyl-6-[(N-benzoyl)(N-benzyl)amino]-quinazolin-4(3H)-one 2-Butyl-3-[4-[(1-carboxy)(1-(2-chlorophenyl)))methoxy]phenyl]methyl-6-[(N-benzyl)(N-n-butyryl)amino]-quinazolin-4(3H)-one 2-Butyl-3-[4-[(1-carboxy)(1-(2-chlorophenyl)))methoxy]phenyl]methyl-6-[(N-(4-chlorobenzoyl))(N-n-pentyl)amino]quinazolin-4(3H)-one 2-Butyl-3-[4-[(1-carboxy)(1-phenyl)methoxy]-3-propylphenyl]methyl-6-[(N-benzyl)(N-iso-butyloxycarbonyl)amino]quinazolin-4(3H)-one 2-Butyl-3-[4-[(1-carboxy)(1-phenyl)methoxy]-3-propylphenyl]methyl-6-[(N-benzyl)(N-n-butyloxycarbonyl)amino]quinazolin-4(3H)-one 2-Butyl-3-[4-[(1-carboxy)(1-phenyl)methoxy]-3-propylphenyl]methyl-6-[(N-benzyl)(N-(N-ethyl-N-methyl)aminocarbonyl)amino]quinazolin-4(3H)-one 2-Butyl-3-[4-[(1-carboxy)(1-phenyl)methoxy]-3-propylphenyl]methyl-6-[(N-benzoyl)(N-n-pentyl)amino]quinazolin-4(3H)-one 2-Butyl-3-[4-[(1-carboxy)(1-phenyl)methoxy]-3-propylphenyl]methyl-6-[(N-benzoyl)(N-benzyl)amino]-quinazolin-4(3H)-one 2-Butyl-3-[4-[(1-carboxy)(1-phenyl)methoxy]-3-propylphenyl]methyl-6-[(N-benzoyl)(N-n-butyryl)amino]-quinazolin-4(3H)-one 2-Butyl-3-[4-[(1-carboxy)(1-phenyl)methoxy]-3-propylphenyl]methyl-6-[(N-(4-chlorobenzoyl))(N-n-pentyl)amino]quinazolin-4(3H)-one 2-Butyl-3-[4-[(1-carboxy)(1-(2-chlorophenyl)))methoxy]-3-propylphenyl]methyl-6-[(N-benzyl)(N-iso-butyloxycarbonyl)amino]quinazolin-4(3H)-one 2-Butyl-3-[4-[(1-carboxy)(1-(2-chlorophenyl)))methoxy]-3-propylphenyl]methyl-6-[(N-benzyl)(N-n-butyloxycarbonyl)amino]quinazolin-4(3H)-one 2-Butyl-3-[4-[(1-carboxy)(1-(2-chlorophenyl)))methoxy]-3-propylphenyl]methyl-6-[(N-benzyl)(N-(N-ethyl-N-methyl)aminocarbonyl)amino]quinazolin-4(3H)-one 2-Butyl-3-[4-[(1-carboxy)(1-(2-chlorophenyl)))methoxy]-3-propylphenyl]methyl-6-[(N-benzoyl)(N-n-pentyl)amino]quinazolin-4(3H)-one 2-Butyl-3-[4-[(1-carboxy)(1-(2-chlorophenyl)))methoxy]-3-propylphenyl]methyl-6-[(N-benzoyl)(N-benzyl)amino]quinazolin-4(3H)-one 2-Butyl-3-[4-[(1-carboxy)(1-(2-chlorophenyl)))methoxy]-3-propylphenyl]methyl-6-[(N-benzoyl)(N-n-butyryl)amino]quinazolin-4(3H)-one 2-Butyl-3-[4-[(1-carboxy)(1-(2-chlorophenyl)))methoxy]-3-propylphenyl]methyl-6-[(N-(4-chlorobenzoyl))(N-n-pentyl)amino]quinazolin-4(3H)-one 2-Butyl-3-[4-[(1-carboxy)(1-phenyl)methoxy]-3-chloro-5-methoxyphenyl]methyl-6-[-(N-methyl)(N-iso-butyloxycarbonyl)amino]quinazolin-4(3H)-one 3-[4-[(1-Carboxy)(1-phenyl)methoxy]-3-chloro-5-methoxyphenyl]methyl-6-[(N-methyl)(N-iso-butyloxycarbonyl)amino]-2-propylquinazolin-4(3H)-one 3-[4-[(1-Carboxy)(1-phenyl)methoxy]-3-propylphenyl]methyl-6[(N-methyl)(N-iso-butyloxycarbonyl)amino]-2-propylquinazolin-4(3H)-one 2-Butyl-3-[4-[(1-carboxy)(1-phenyl)methoxy]phenyl]methyl-6-methylsulfonylquinazolin-4(3H)-one 2-Butyl-3-[4-[(1-carboxy)(1-(2-chlorophenyl)))methoxy]phenyl]methyl-6-methylquinazolin-4(3H)-one 2-Butyl-3-[4-[(1-carboxy)(-1-(2-chlorophenyl)))methoxy]phenyl]methyl-6-methylsulfonylquinazolin-4(3H)-one 2-Butyl-3-[4-[(1-carboxy)(1-(2-methylphenyl)))methoxy]phenyl]methyl-6-methylsulfonylquinazolin-4(3H)-one 2-Butyl-3-[4-[(1-carboxy)(1-(2-methoxyphenyl)))methoxy]phenyl]methyl-6-methylsulfonylquinazolin-4(3H)-one 2-Butyl-3-[4-[(1-carboxy)(1-(2,6-dimethylphenyl)))methoxy]phenyl]methyl-6-methylsulfonylquinazolin-4(3H)-one 2-Butyl-3-[4-[(1-carboxy)(1-(2-trifluoromethylphenyl))methoxy]phenyl]methyl-6-methylsulfonylquinazolin-4(3H)-one 2-Butyl-3-[4-[(1-carboxy)(1-(2-dimethylaminophenyl))methoxy]phenyl]methyl-6-methylsulfonylquinazolin-4(3H)-one 2-Butyl-3-[4-[(1-carboxy)(1-(2-chlorophenyl)))methoxy]phenyl]methyl-5-hydroxymethylquinazolin-4(3H)-one 2-Butyl-5-carbomethoxy-3-[4-[(1-carboxy)(1-(2-chlorophenyl)))methoxy]phenyl]methylquinazolin-4(3H)-one 2-Butyl-5-carbomethoxy-3-[4-[(1-carboxy)(1-(2-chlorophenyl)))methoxy]phenyl]methyl-6-methylquinazolin-4(3H)-one 2-Butyl-3-[4-[(1-carboxy)(1-(1-naphthyl))methoxy]phenyl]methyl-6-methylquinazolin-4(3H)-one 2-Butyl-3-[4-[(1-carboxy)(1-phenyl)methoxy]-3-chlorophenyl]methyl-6-methylquinazolin-4(3H)-one 2-Butyl-3-[4-[(1-carboxy)(1-phenyl)methoxy]-3-methylphenyl]methyl-6-methylquinazolin-4(3H)-one 2-Butyl-3-[4-[(1-carboxy)(1-phenyl)methoxy]-3-ethylphenyl]methyl-6-methylquinazolin-4(3H)-one 2-Butyl-3-[4-[(1-carboxy)(1-phenyl)methoxy]-3-allylphenyl]methyl-6-methylquinazolin-4(3H)-one 2-Butyl-3-[4-[(1-carboxy)(1-phenyl)methoxy]-3-propylphenyl]methyl-6-methylquinazolin-4(3H)-one 6-Methyl-2-propyl-3-[4-[(1-tetrazol-5-yl)(1-phenyl)methoxy]phenyl]methylquinazolin-4(3H)-one 2-Butyl-6-methyl-3-[4-[(1-tetrazol-5-yl)(1-phenyl)methoxy]phenyl]methylquinazolin-4(3H)-one 2-Butyl-6-dimethyamino-3-[4-[(1-tetrazol-5-yl)(1-phenyl)methoxy]phenyl]methylquinazolin-4(3H)-one 2-Butyl-6-(N-methoxycarbonylamino)-3-[4-[(1-tetrazol-5-yl)(1-phenyl)methoxy]phenyl]methylquinazolin-4(3H)-one 2-Butyl-6-[(N-methyl)(N-methoxycarbonyl)amino]-3-[4-[(1-tetrazol-5-yl)(1-phenyl)methoxy]phenyl]methylquinazolin-4(3H)-one 2-Butyl-6-[(N-methyl)(N-iso-butyloxycarbonyl)amino]-3-[4-[(1-tetrazol-5-yl)(1-phenyl)methoxy]phenyl]methylquinazolin-4(3H)-one 2-Butyl-6-methylsulfonyl-3-[4-[(1-tetrazol-5-yl)(1-phenyl)methoxy]phenyl]methylquinazolin-4(3H)-one 2-Butyl-6-methyl-3-[4-[(1-tetrazol-5-yl)(1-(2-chlorophenyl)))methoxy]phenyl]methylquinazolin-4(3H)-one 2-Butyl-6-methylsulfonyl-3-[4-[(1-tetrazol-5-yl)(1-(2-chlorophenyl)))methoxy]phenyl]methylquinazolin-4(3H)-one 2-Butyl-6-methylsulfonyl-3-[4-[(1-tetrazol-5-yl)(1-(2-methylphenyl)))methoxy]phenyl]methylquinazolin-4(3H)-one 2-Butyl-6-methylsulfonyl-3-[4-[(1-tetrazol-5-yl)(1-(2-methoxyphenyl))methoxy]phenyl]methylquinazolin-4-(3H)-one 2-Butyl-6-methylsulfonyl-3-[4-[(1-tetrazol-5-yl)(1-(2,6-dimethylphenyl))methoxy]phenyl]methylquinazolin-4(3H)-one 2-Butyl-6-methylsulfonyl-3-[4-[(1-tetrazol-5-yl)(1-(2-trifluoromethylphenyl))methoxy]phenyl]methyl-quinazolin-4(3H)-one 2-Butyl-6-methylsulfonyl-3-[4-[(1-tetrazol-5-yl)(1-(2-dimethylaminophenyl))methoxy]phenyl]methyl-quinazolin-4(3H)-one 2-Butyl-5-hydroxymethyl-3-[4-[(1-tetrazol-5-yl)(1-(2-chlorophenyl))methoxy]phenyl]methylquinazolin-4-(3H)-one 2-Butyl-5-carbomethoxy-3-[4-[(1-tetrazol-5-yl)(1-(2-chlorophenyl))methoxy]phenyl]methylquinazolin-4(3H)-one 2-Butyl-5-carbomethoxy-6-methyl-3-[4-[(1-tetrazol-5-yl)(1-(2-chlorophenyl))methoxy]phenyl]methyl-quinazolin-4(3H)-one 2-Butyl-6-methyl-3-[4-[(1-tetrazol-5-yl)(1-(1-naphthyl))methoxy]phenyl]methylquinazolin-4(3H)-one 2-Butyl-3-[4-[(1-(N-phenylsulfonyl)carboxamido)(1-(2-chlorophenyl))methoxy]phenyl]methyl-6-methylsulfonylquinazolin-4(3H)-one N-Methyl 2-butyl-3-[4-[(1-carboxy)(1-(2-chlorophenyl))methoxy]phenyl]methyl-6-methylsulfonylquinazolin-4(3H)-imine Preferred compounds of the present invention which are illustrative of subclasses of Formula Ib are:

DIHYDROTRIAZOLONES

2-Benzyl-5-butyl-4-[4-[(1-carboxy)(1-(2-chlorophenyl))methoxy]phenyl]methyl-2,4-dihydro-3H-1,2,4-triazol-3-one 2-Benzyl-5-butyl-4-[4-[(1-carboxy)(1-(2-chlorophenyl))methoxy]-3-methylphenyl]methyl-2,4-dihydro-3H-1,2,4-tiriazol-3-one 2-Benzyl-5-butyl-4-[4-[(1-carboxy)(1-(2-chlorophenyl))methoxy]-3-allylphenyl]methyl-2,4-dihydro-3H-1,2,4-triazol-3-one 2-Benzyl-5-butyl-4-[4-[(1-carboxy)(1-(2-chlorophenyl))methoxy-3-propylphenyl]methyl-2,4-dihydro-3H-1,2,4-triazol-3-one 2-Benzyl-4-[4-[(1-carboxy)(1-(2-chlorophenyl))methoxy]-phenyl]methyl-2,4-dihydro-5-propyl-3H-1,2,4-triazol-3-one 2-Butyl-4-[4-[(1-carboxy)(1-(2-chlorophenyl))methoxy]phenyl]methyl-2,4-dihydro-5-propyl-3H-1,2,4-triazol-3-one 4-[4-[(1-carboxy)(1-(2-chlorophenyl))methoxy]phenyl]methyl-2,5-dibutyl-2,4-dihydro-3H-1,2,4-triazol-3-one 4-[4-[(1-carboxy)(1-(2-chlorophenyl))methoxy]phenyl]methyl-2-cyclopentyl-2,4-dihydro-5-propyl-3H-1,2,4-triazol-3-one 5-Butyl-4-[4-[(1-carboxy)(1-(2-chlorophenyl))methoxy]phenyl]methyl-2,4-dihydro-2-carbomethoxymethyl-3H-1,2,4-triazol-3-one 5-Butyl-4-[4-[(1-carboxy)(1-(2-chlorophenyl))methoxy]phenyl]methyl-2-carboxymethyl-2,4-dihydro-3H-1,2,4-triazol-3-one 5-Butyl-4-[4-[(1-carboxy)(1-(2-chlorophenyl))methoxy]phenyl]methyl-2,4-dihydro-2-hydroxymethyl-3H-1,2,4-triazol-3-one 5-Butyl-4-[4-[(1-carboxy)(1-phenyl)methoxyphenyl]-methyl-2,4-dihydro-2-(2-carboxyphenyl)-3H-1,2,4-triazol-3-one 5-Butyl-4-[4-[(1-carboxy)(1-phenyl)methoxyphenyl]-methyl-2-(2-chlorophenyl)-2,4-dihydro-3H-1,2,4-triazol-3-one 5-Butyl-4-[4-[(1-carboxy)(1-phenyl)methoxy]-3-methylphenyl]methyl-2-(2-chlorophenyl)-2,4-dihydro-3H-1,2,4-triazol-3-one 5-Butyl-4-[4-[(1-carboxy)(1-phenyl)methoxy]-3-allylphenyl]methyl-2-(2-chlorophenyl)-2,4-dihydro-3H-1,2,4-triazol-3-one 5-Butyl-4-[4-[(1-carboxy)(1-phenyl)methoxy]-3-propylphenyl]methyl-2-(2-chlorophenyl)-2,4-dihydro-3H-1,2,4-triazol-3-one 5-Butyl-4-[4-[(1-carboxy)(1-phenyl)methoxyphenyl]-methyl-2,4-dihydro-2-(2-trifluoromethylphenyl)-3H-1,2,4-triazol-3-one 5-Butyl-4-[4-[(1-carboxy)(1-phenyl)methoxyphenyl]-methyl-2,4-dihydro-2-(2-methylphenyl)-3H-1,2,4-triazol-3-one 5-Butyl-4-[4-[(1-carboxy)(1-phenyl)methoxy]-3-methylphenyl]methyl-2,4-dihydro-2-(2-methylphenyl)-3H-1,2,4-triazol-3-one 5-Butyl-4-[4-[(1-carboxy)(1-phenyl)methoxy]-3-allylphenyl]methyl-2,4-dihydro-2-(2-methylphenyl)-3H-1,2,4-triazol-3-one 5-Butyl-4-[4-[(1-carboxy)(1-phenyl)methoxy]-3-propylphenyl]methyl-2,4-dihydro-2-(2-methylphenyl)-3H-1,2,4-triazol-3-one 5-Butyl-4-[4-[(1-carboxy)(1-phenyl)methoxyphenyl]-methyl-2,4-dihydro-2-(2-nitrophenyl)-3H-1,2,4-triazol-3-one 5-Butyl-4-[4-[(1-carboxy)(1-phenyl)methoxyphenyl]-methyl-2,4-dihydro-2-(2-hydroxymethylphenyl)-3H-1,2,4-triazol-3-one 5-Butyl-4-[4-[(1-carboxy)(1-phenyl)methoxyphenyl]-methyl-2,4-dihydro-2-(2-chloro-4-methoxyphenyl)-3H-1,2,4-triazol-3-one 5-Butyl-4-[4-[(1-carboxy)(1-(2-chlorophenyl))methoxy]phenyl]methyl-2,4-dihydro-2-(2-chlorophenyl)-3H-1,2,4-triazol-3-one 5-Butyl-4-[4-[(1-carboxy)(1-(1-naphthyl))methoxy]-phenyl]-methyl-2,4-dihydro-2-(2-chlorophenyl)-3H-1,2,4-triazol-3-one 5-Butyl-4-[4-[(1-carboxy)(1-(2-methyl)phenyl))methoxy]phenyl]methyl-2,4-dihydro-2-(2-chlorophenyl)-3H-1,2,4-triazol-3-one 5-Butyl-4-[4-[(1-carboxy)(1-(2-isopropylphenyl))methoxy]-phenyl]methyl-2,4-dihydro-2-(2-chlorophenyl)-3H-1,2,4-triazol-3-one 5-Butyl-4-[4-[N-[(1-carboxy)(1-(2-chlorophenyl))]methylamino]phenyl]methyl-2,4-dihydro-2-(2-chlorophenyl)-3H-1,2,4-triazol-3-one 5-Butyl-4-[4-[N-[(1-carboxy)(1-(2-chlorophenyl))methyl]-N-methylamino]phenyl]methyl-2,4-dihydro-2-(2-chlorophenyl)-3H-1,2,4-triazol-3-one 5-Butyl-4-[4-[N-[(1-carboxy)(1-(2-chlorophenyl))methyl]-N-butylamino]phenyl]methyl-2,4-dihydro-2-(2-chlorophenyl)-3H-1,2,4-triazol-3-one 5-Butyl-4-[4-[(1-carboxy)(1-(2-chlorophenyl))methylthio]phenyl]methyl-2,4-dihydro-2-(2-chlorophenyl)-3H-1,2,4-triazol-3-one 5-Butyl-4-[4-[(1-carboxy)(1-(2-chlorophenyl))methylsulfonyl]phenyl]methyl-2,4-dihydro-2-(2-chlorophenyl)-3H-1,2,4-triazol-3-one 2-Benzyl-5-butyl-4-[4-[(1-carboxy)(1-(2-chlorophenyl))methoxy]phenyl]methyl-2,4-dihydro-3H-1,2,4-triazol-3-one 2-Benzyl-5-butyl-2,4-dihydro-4-[4-[(1-tetrazol-5-yl)(1-(2-chlorophenyl))methoxy]phenyl]methyl-3H-1,2,4-triazol-3-one 2-Benzyl-2,4-dihydro-5-propyl-4-[4-[(1-tetrazol-5-yl)(1-(2-chlorophenyl))methoxy]phenyl]methyl-3H-1,2,4-triazol-3-one 2-Butyl-2,4-dihydro-5-propyl-4-[4-[-(1-tetrazol-5-yl)(1-(2-chlorophenyl))methoxy]phenyl]methyl-3H-1,2,4-triazol-3-one 5-Butyl-2,4-dihydro-4-[4-[(1-tetrazol-5-yl)(1-phenyl)methoxy]phenyl]methyl-2-(2-trifluoromethylphenyl)-3H-1,2,4-triazol-3-one 2-Butyl-2,4-dihydro-5-propyl-4-[4-[(1-tetrazol-5-yl)(1-(2-methylphenyl))methoxy]phenyl]methyl-3H-1,2,4-triazol-3-one 2-Cyclopentyl-2,4-dihydro-5-propyl-4-[4-[(1-tetrazol-5-yl)(1-(2-chlorophenyl))methoxy]phenyl]methyl-3H-1,2,4-triazol-3-one 5-Butyl-2,4-dihydro-2-carbomethoxymethyl-4-[4-[(1-tetrazol-5-yl)(1-(2-chlorophenyl))methoxy]phenyl]methyl-3H-1,2,4-triazol-3-one 5-Butyl-2-carboxymethyl-2,4-dihydro-4-[4-[(1-tetrazol-5-yl)(1-(2-chlorophenyl))methoxy]phenyl]methyl-3H-1,2,4-triazol-3-one 5-Butyl-2,4-dihydro-2-hydroxymethyl-4-[4-[(1-tetrazol-5-yl)(1-(2-chlorophenyl))methoxy]phenyl]methyl-3H-1,2,4-triazol-3-one 5-Butyl-2,4-dihydro-2-(2-carboxy)phenyl-4-[4-[(1-tetrazol-5-yl)(1-phenyl)methoxy]phenyl]methyl-3H-1,2,4-triazol-3-one 5-Butyl-2,4-dihydro-2-(2-chlorophenyl)-4-[4-[(1-tetrazol-5-yl)(1-phenyl)methoxy]phenyl]methyl-3H-1,2,4-triazol-3-one 5-Butyl-2,4-dihydro-2-(2-methylphenyl)-4-[4-[(1-tetrazol-5-yl)(1-phenyl)methoxy]phenyl]methyl-3H-1,2,4-triazol-3-one 5-Butyl-2,4-dihydro-2-(2-nitrophenyl)-4-[4-[(1-tetrazol-5-yl)(1-phenyl))methoxy]phenyl]methyl-3H-1,2,4-triazol-3-one 5-Butyl-2,4-dihydro-2-(2-hydroxymethylphenyl)-4-[4-[(1-tetrazol-5-yl)(1-phenyl)methoxy]phenyl]methyl-3H-1,2,4-triazol-3-one 5-Butyl-2,4-dihydro-2-(2-chloro-4-methoxyphenyl)-4-[4-[(1-tetrazol-5-yl)(1-phenyl)methoxy]phenyl]methyl-3H-1,2,4-triazol-3-one 5-Butyl-2,4-dihydro-2-(2-chlorophenyl)-4-[4-[(1-tetrazol-5-yl)(1-(2-chlorophenyl))methoxy]phenyl]methyl-3H-1,2,4-triazol-3-one 5-Butyl-2,4-dihydro-2-(2-chlorophenyl)-4-[4-[(1-tetrazol-5-yl)(1-(1-naphthyl))methoxy]phenyl]methyl-3H-1,2,4-triazol-3-one 5-Butyl-2,4-dihydro-2-(2-chlorophenyl)-4-[4-[(1-tetrazol-5-yl)(1-(2-methylphenyl))methoxy]phenyl]methyl-3H-1,2,4-triazol-3-one 5-Butyl-4-[4-[N-((1-carboxy)(1-(2-chlorophenyl))methyl)amino]phenyl]methyl-2,4-dihydro-2-(2-chlorophenyl)-3H-1,2,4-triazol-3-one 5-Butyl-4-[4-(N-((1-tetrazol-5-yl)(1-(2-chlorophenyl))methyl)(N-methyl))amino]phenyl]methyl-2,4-dihydro-2-(2-chlorophenyl)-3H-1,2,4-triazol-3-one 5-Butyl-4-[4-[(N-((1-tetrazol-5-yl)(1-(2-chlorophenyl))methyl)(N-butyl))amino]phenyl]methyl-2,4-dihydro-2-(2-chlorophenyl)-3H-1,2,4-triazol-3-one 5-Butyl-4-[4-[(1-tetrazol-5-yl)(1-(2-chlorophenyl))methylthio]phenyl]methyl-2,4-dihydro-2-(2-chlorophenyl)-3H-1,2,4-triazol-3-one 5-Butyl-4-[4-[(1-tetrazol-5-yl)(1-(2-chlorophenyl))methylsulfonyl]phenyl]methyl-2,4-dihydro-2-(2-chlorophenyl)-3H-1,2,4-triazol-3-one 5-Butyl-4-[4-[(1-(N-phenylsulfonyl)carboxamido)(1-phenyl)methoxy]phenyl]methyl-2,4-dihydro-2-(2-chlorophenyl)-3H-1,2,4-triazol-3-one 5-Butyl-4-[4-[(1-(N-methylsulfonyl)carboxamido)(1-phenyl)methoxy]phenyl]methyl-2,4-dihydro-2-(2-chlorophenyl)-3H-1,2,4-triazol-3-one 5-Butyl-4-[4-[(1-(N-trifluoromethylsulfonyl)carboxamido)(1-phenyl)methoxy]phenyl]methyl-2,4-dihydro-2-(2-chlorophenyl)-3H-1,2,4-triazol-3-one N-Methyl 5-butyl-4-[4-[(1-carboxy)(1-phenyl)methoxy]phenyl]methyl-2,4-dihydro-2-(2-chlorophenyl)-3H-1,2,4-triazol-3-imine Preferred compounds of the present invention which are illustrative of subclasses of Formula Ic are:

PYRIMIDIN-4(3H)-ONES

3-[4-[(1-Carboxy)(1-phenyl)methoxy]phenyl]methyl-6-methyl-2-propylpyrimidin-4(3H)-one 2-Butyl-3-[4-[(1-carboxy)(1-phenyl)methoxy]phenyl]methyl-6-methylpyrimidin-4(3H)-one 2-Butyl-3-[4-[(1-carboxy)(1-phenyl)methoxy]phenyl]methyl-6-phenylpyrimidin-4(3H)-one 2-Butyl-3-[4-[(1-carboxy)(1-phenyl)methoxy]phenyl]methyl-6-(2-chlorophenyl)pyrimidin-4(3H)-one 2-Butyl-3-[4-[(1-carboxy)(1-phenyl)methoxy]phenyl]methyl-5,6-dimethylpyrimidin-4(3H)-one 2-Butyl-3-[4-[(1-carboxy)(1-phenyl)methoxy]phenyl]methyl-5-(2-chlorophenyl)pyrimidin-4(3H)-one 2-Butyl-3-[4-[(1-carboxy)(1-phenyl)methoxy]phenyl]methyl-5-(2-methylphenyl)pyrimidin-4(3H)-one 2-Butyl-3-[4-[(1-carboxy)(1-(2-chlorophenyl))methoxy]phenyl]methyl-6-methylpyrimidin-4(3H)-one 2-Butyl-3-[4-[(1-carboxy)(1-(2-chlorophenyl))methoxy]phenyl]methyl-6-methylpyrimidin-4(3H)-one 2-Butyl-3-[4-[(1-carboxy)(1-(2-methylphenyl))methoxy]phenyl]methyl-6-methylpyrimidin-4(3H)-one 2-Butyl-3-[4-[(1-carboxy)(1-(2-methoxyphenyl))methoxy]phenyl]methyl-6-methylpyrimidin-4(3H)-one 2-Butyl-3-[4-(1-carboxy)(1-(2,6-dimethylphenyl))methoxy]phenyl]methyl-6-methylpyrimidin-4(3H)-one 2-Butyl-3-[4-[(1-carboxy)(1-(2-trifluoromethylphenyl))methoxy]phenyl]methyl-6-methylpyrimidin-4(3H)-one 2-Butyl-3-[4-[(1-carboxy)(1-(2-dimethylaminophenyl))methoxy]phenyl]methyl-6-methylpyrimidin-4(3H)-one 2-Butyl-3-[4-[(1-carboxy)(1-phenyl)methoxy]phenyl]methyl-6-methyl-5-phenylpyrimidin-4(3H)-one 2-Butyl-3-[4-[(1-carboxy)(1-phenyl)methoxy]phenyl]methyl-6-methyl-5-(pentafluoroethyl)pyrimidin-4(3H)-one 2-Butyl-3-[4-[(1-carboxy)(1-phenyl)methoxy]phenyl]methyl-5-(2-chlorophenyl)-6-methylpyrimidin-4(3H)-one 2-Butyl-3-[4-[(1-carboxy)(1-phenyl)methoxy]phenyl]methyl-5-(2,6-dichlorophenyl)-6-methylpyrimidin-4(3H)-one 2-Butyl-3-[4-[(1-carboxy)(1-phenyl)methoxy]phenyl]methyl-6-methyl-5-(2-trifluoromethylphenyl)pyrimidin-4(3H)-one 2-Butyl-3-[4-[(1-carboxy)(1-phenyl)methoxy]-3-methylphenyl]methyl-6-methyl-5-phenylpyrimidin-4(3H)-one 2-Butyl-3-[4-[(1-carboxy)(1-phenyl)methoxy]-3-methylphenyl]methyl-6-methyl-5-(pentafluoroethyl)pyrimidin-4(3H)-one 2-Butyl-3-[4-[(1-carboxy)(1-phenyl))methoxy]-3-methylphenyl]methyl-5-(2-chlorophenyl)-6-methylpyrimidin-4(3H)-one 2-Butyl-3-[4-[(1-carboxy)(1-phenyl)methoxy]-3-methylphenyl]methyl-5-(2,6-dichlorophenyl)-6-methylpyrimidin-4(3H)-one 2-Butyl-3-[4-[(1-carboxy)(1-phenyl)methoxy]-3-methylphenyl]methyl-6-methyl-5-(2-trifluoromethylphenyl)pyrimidin-4(3H)-one 2-Butyl-3-[4-[(1-carboxy)(1-phenyl)methoxy]-3-chlorophenyl]methyl-6-methyl-5-phenylpyrimidin-4(3H)-one 2-Butyl-3-[4-[(1-carboxy)(1-phenyl)methoxy]-3-chlorophenyl]methyl-6-methyl-5-(pentafluoroethyl)pyrimidin-4(3H)-one 2-Butyl-3-[4-[(1-carboxy)(1-phenyl)methoxy]-3-chlorophenyl]methyl-5-(2-chlorophenyl)-6-methylpyrimidin-4(3H)-one 2-Butyl-3-[4-[(1-carboxy)(1-phenyl)methoxy]-3-chlorophenyl]methyl-5-(2,6-dichlorophenyl)-6-methylpyrimidin-4(3H)-one 2-Butyl-3-[4-[(1-carboxy)(1-phenyl)methoxy]-3-chlorophenyl]methyl-6-methyl-5-(2-trifluoromethylphenyl)pyrimidin-4(3H)-one 2-Butyl-3-[4-[(1-carboxy)(1-phenyl)methoxy]-3-propylphenyl]methyl-6-methyl-5-phenylpyrimidin-4(3H)-one 2-Butyl-3-[4-[(1-carboxy)(1-phenyl)methoxy]-3-propylphenyl]methyl-6-methyl-5-(pentafluoroethyl)pyrimidin-4(3H)-one 2-Butyl-3-[4-[(1-carboxy)(1-phenyl)methoxy]-3-propylphenyl]methyl-5-(2-chlorophenyl)-6-methylpyrimidin-4(3H)-one 2-Butyl-3-[4-[(1-carboxy)(1-phenyl)methoxy]-3-propylphenyl]methyl-5-(2,6-dichlorophenyl)-6-methylpyrimidin-4(3H)-one 2-Butyl-3-[4-[(1-carboxy)(1-phenyl)methoxy]-3-propylphenyl]methyl-6-methyl-5-(2-trifluoromethylphenyl)pyrimidin-4(3H)-one 2-Butyl-3-[4-[(1-carboxy)(1-(2-chlorophenyl))methoxy]-3-propylphenyl]methyl-6-methyl-5-phenylpyrimidin-4(3H)-one 2-Butyl-3-[4-[(1-carboxy)(1-(2-chlorophenyl))methoxy]-3-propylphenyl]methyl-6-methyl-5-(pentafluoroethyl)pyrimidin-4(3H)-one 2-Butyl-3-[4-[(1-carboxy)(1-(2-chlorophenyl))methoxy]-3-propylphenyl]methyl-5-(2-chlorophenyl)-6-methylpyrimidin-4(3H)-one 2-Butyl-3-[4-[(1-carboxy)(1-(2-chlorophenyl))methoxy]-3-propylphenyl]methyl-5-(2,6-dichlorophenyl)-6-methylpyrimidin-4(3H)-one 2-Butyl-3-[4-[(1-carboxy)(1-(2-chlorophenyl))methoxy]-3-propylphenyl]methyl-6-methyl-5-(2-trifluoromethylphenyl)pyrimidin-4(3H)-one 2-Butyl-3-[4-(1-carboxy)(1-(2-chlorophenyl))methoxy]-phenyl]methyl-5-hydroxymethylpyrimidin-4(3H)-one 2-Butyl-5-carbomethoxy-3-[4-[(1-carboxy)(1-(2-chlorophenyl))methoxy]phenyl]methylpyrimidin-4(3H)-one 2-Butyl-5-carbomethoxy-3-[4-[(1-carboxy)(1-(2-chlorophenyl))methoxy]phenyl]methyl-6-methylpyrimidin-4(3H)-one 2-Butyl-3-[4-[(1-carboxy)(1-(1-naphthyl))methoxy]phenyl]methyl-6-methylpyrimidin-4(3H)-one 6-Methyl-2-propyl-3-[4-[(1-tetrazol-5-yl)(1-phenyl)methoxy]phenyl]methylpyrimidin-4(3H)-one 2-Butyl-6-methyl-3-[4-[(1-tetrazol-5-yl)(1-phenyl)methoxy]phenyl]methylpyrimidin-4(3H)-one 2-Butyl-5,6-dimethyl-3-[4-[(1-tetrazol-5-yl)(1-phenyl)methoxy]phenyl]methylpyrimidin-4(3H)-one 2-Butyl-6-phenyl-3-[4-[(1-tetrazol-5-yl)(1-phenyl)methoxy]phenyl]methylpyrimidin-4(3H)-one 2-Butyl-6-(2-chlorophenyl)-3-[4-[(1-tetrazol-5-yl)(1-phenyl)methoxy]phenyl]methylpyrimidin-4(3H)-one 2-Butyl-5-(2-chlorophenyl)-3-[4-[(1-tetrazol-5-yl)(1-phenyl)methoxy]phenyl]methylpyrimidin-4(3H)-one 2-Butyl-6-methyl-3-[4-[(1-tetrazol-5-yl)(1-(2-chlorophenyl))methoxy]phenyl]methylpyrimidin-4(3H)-one 2-Butyl-6-methyl-3-[4-[(1-tetrazol-5-yl)(1-(2-chlorophenyl))methoxy]phenyl]methylpyrimidin-4(3H)-one 2-Butyl-6-methyl-3-[4-[(1-tetrazol-5-yl)(1-(2-methylphenyl))methoxy]phenyl]methylpyrimidin-4(3H)-one 2-Butyl-6-methyl-3-[4-[(1-tetrazol-5-yl)(1-(2-methoxyphenyl))methoxy]phenyl]methylpyrimidin-4(3H)-one 2-Butyl-6-methyl-3-[4-[(1-tetrazol-5-yl)(1-(2,6-dimethylphenyl))methoxy]phenyl]methylpyrimidin-4(3H)-one 2-Butyl-6-methyl-3-[4-[(1-tetrazol-5-yl)(1-(2-trifluoromethylphenyl))methoxy]phenyl]methylpyrimidin-4(3H)-one 2-Butyl-6-methyl-3-[4-[(1-tetrazol-5-yl)(1-(2-dimethylaminophenyl))methoxy]phenyl]methylpyrimidin-4(3H)-one 2-Butyl-5-hydroxymethyl-3-[4-[(1-tetrazol-5-yl)(1-(2-chlorophenyl))methoxy]phenyl]methylpyrimidin-4(3H)-one 2-Butyl-5-carbomethoxy-3-[4-[(1-tetrazol-5-yl)(1-(2-chlorophenyl))methoxy]phenyl]methylpyrimidin-4(3H)-one 2-Butyl-5-carbomethoxy-6-methyl-3-[4-[(1-tetrazol-5-yl)(1-(2-chlorophenyl))methoxy]phenyl]methylpyrimidin-4(3H)-one 2-Butyl-6-methyl-3-[4-[(1-tetrazol-5-yl)(1-(1-naphthyl))methoxy]phenyl]methylpyrimidin-4(3H)-one 2-Butyl-3-[4-[(1-(N-phenylsulfonyl)carboxamido)(1-phenyl)methoxy]phenyl]methyl-5-(2-chlorophenyl)-6-methylpyrimidin-4(3H)-one 2-Butyl-3-[4-[(1-(N-methylsulfonyl)carboxamido)(1-(2-chlorophenyl))methoxy]phenyl]methyl-5-(2-chlorophenyl)-6-methylpyrimidin-4(3H)-one 2-Butyl-3-[4-[(1-(N-trifluoromethylsulfonyl)carboxamido)(1-(2-chlorophenyl))methoxy]phenyl]methyl-5-(2-chlorophenyl)-6-methylpyrimidin-4(3H)-one N-Methyl-2-Butyl-3-[4-[(1-carboxy)(1-(2-chlorophenyl))methoxy)phenyl]methyl-5-(2-chlorophenyl)-6-methylpyrimidin-4(3H)-imine.

GENERAL METHODS FOR PREPARATION OF COMPOUNDS OF GENERAL FORMULA I

The methods described in PART I AND PART II below illustrate the preparation of angiotensin II antagonists of Formula I. There are several general approaches to the synthesis of antagonists of Formula I, and it is taken as a general principle that one or another method may be more readily applicable for the preparation of a given antagonist; some of the approaches illustrated below may not be readily applicable for the preparation of certain antagonists of Formula I.

It should be recognized that antagonists of Formula I consist of a heterocyclic component designated above by formulas Ia through Ic and a substituted benzyl substitutent which is attached to the heterocyclic component at a nitrogen atom. Thus, two generally applicable approaches to antagonists of formula I are these:

1. A heterocycle, designated above with Formulas Ia through Ic is prepared as described in PART I below. Then the heterocycle is alkylated at a nitrogen atom with a substituted benzyl halide or pseudohalide giving an alkylated heterocycle in the Schemes below, this alkylating agent is often designated as "Ar—CH$_2$Q" where Q is a halide (—Cl, Br, I) or pseudohalide (—OMs, OTs, OTf). In some cases, alkylation may take place at more than one nitrogen atom of the heterocycle, and in these cases, separation by fractional crystallization or by chromotographic methods may be necessary for isolation of the desired product. In some cases, the alkylation step produces a fully-assembled antagonist of Formula I, except that functional groups in the alkylating agent or in the heterocycle may be present in protected form and require deprotection steps to be carried out to complete the synthesis. In other cases, the alkylation is carried out with a substituted benzylic halide or pseudohalide ("Ar—CH$_2$Q"), but here the alkylation step is followed by subsequent steps which are required to assemble the substituted benzyl element of the antagonist of Formula I. The alkylation steps and subsequent steps used to prepare antagonists of Formula I, are described in PART II below.

2. In another approach to antagonists of Formula I, a substituted benzyl element is introduced at the beginning of, or during the preparation of the heterocyclic element. Routes of this type are illustrated in Part II below. In most cases where this general approach is used, the substituted benzyl component which is introduced during the synthesis of the heterocycle must be subjected to further synthetic transformations in order to complete the synthesis of the antagonist of Formula I. In the Schemes shown below in PART II, this substituted benzyl component is designated as "—CH$_2$Ar," and is usually introduced by an alkylation step with a substituted benzyl halide or pseudohalide designated ArCH$_2$—Q (where Q is, for example, Cl, Br, I, F, OTs, or OMs), or is introduced by a route which starts with a substituted benzylamine, designated "ArCH$_2$NH$_2$". The required substituted benzylamine derivatives may be prepared by standard methods, for example from the substituted benzylic halides or pseudohalides ("ArCH$_2$—Q"). Substituted benzyl halides or pseudohalides which are useful in the preparation of alkylated heterocycles described in PART I are illustrated by those listed below in Table 1. Substituted benzyl amines which are useful in the preparation of the alkylated heterocycles described in PART I are illustrated by those listed below in Table 2. In cases where these benzylic halides, pseudohalides and amines are not commercially available, they are prepared as described in Part II below or by standard methods of organic synthesis. Subsequent steps which may be required to complete the synthesis of antagonists of Formula I are described in PART II below.

The compounds of this invention may be resolved using techniques known in the art. The diastereomeric salts or esters of the enantiomers are separated and the desired compound is the more active stereoisomer. The compounds of this invention, their pharmaceutically acceptable salts and their prodrug forms are included within the scope of this invention.

TABLE 1

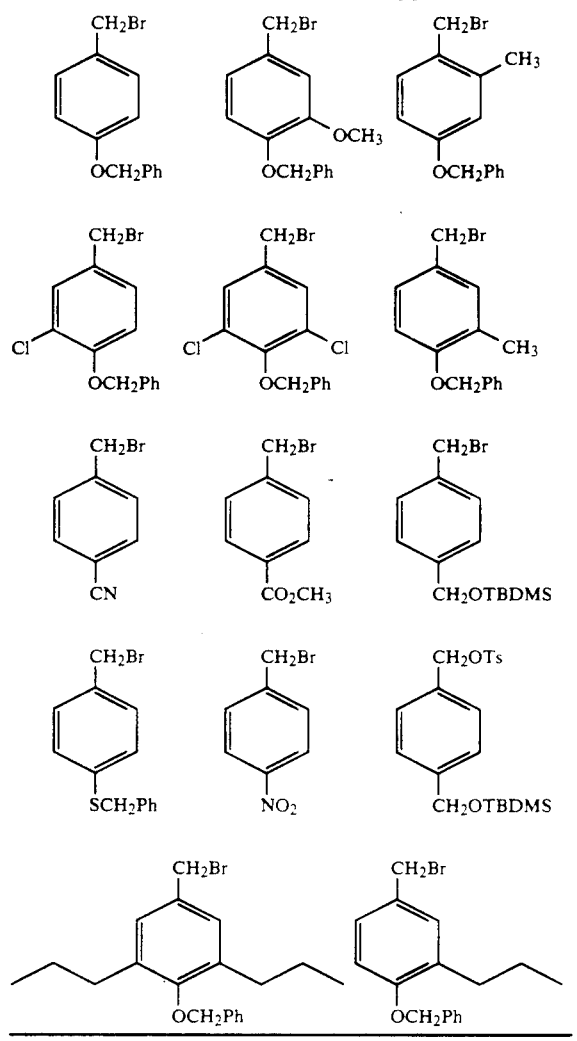

TABLE 1

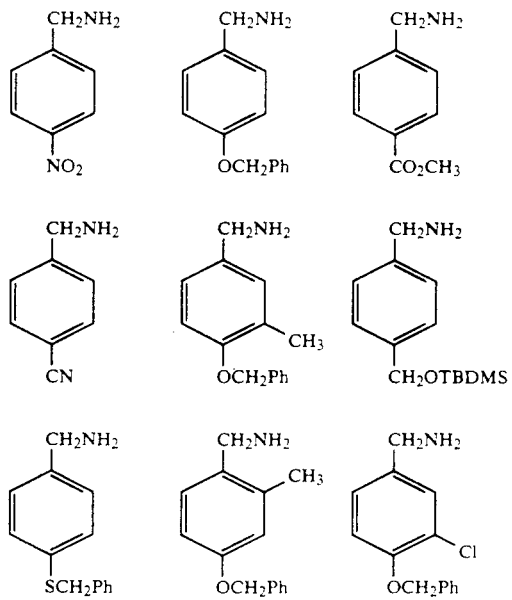

TABLE 1-continued

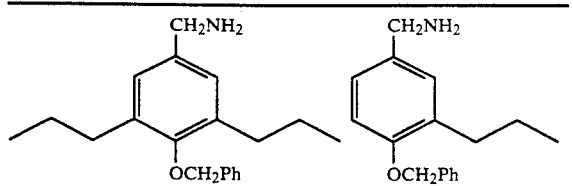

TABLE 3

| Reagents | |
|---|---|
| NBS | N-bromosuccinimide |
| AIBN | Azo(bis) isobutyronitrile |
| DDQ | Dichlorodicyanoquinone |
| Ac$_2$O | acetic anhydride |
| TEA | triethylamine |
| DMAP | 4-dimethylaminopyridine |
| PPh$_3$ | triphenylphosphine |
| TFA | trifluroacetic acid |
| TMS-Cl | trimethylsilyl chloride |
| Im | imidazole |
| AcSK | potassium thioacetate |
| p-TsOH | p-toluenesulfonic acid |
| FMOC-Cl | 9-Fluorenylmethyloxycarbonyl chloride |
| Solvents: | |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| Others: | |
| rt | room temperature |
| TBDMS | t-butyldimethylsilyl |
| OTf | OSO$_2$CF$_3$ |
| Ph | phenyl |
| FAB-MS (FSBMS) | Fast atom bombardment mass spectroscopy |
| NOE | Nuclear Overhauser Effect |
| SiO$_2$ | silica gel |
| trityl | triphenylmethyl |
| Bn | benzyl |

PART I: Preparation of the heterocycles shown in Formulas Ia, Ib, and Ic.

A. Preparation of quinazolinones (Formula Ia)

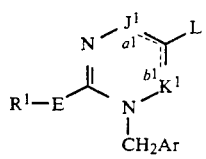

Scheme I-1 illustrates the preparation of 1,2-disubstituted quinazolin-4(1H)-one of Formula Ia wherein $J^1 = -C(O)-$ and E is a single bond. An appropriately substituted anthranilonitrile is acylated using the requisite acyl chloride. The resulting amide is alkylated with sodium hydride and the appropriate alkyl halide (or pseudohalide). The resulting tertiary amide is then rearranged/cyclized with basic hydrogen peroxide[1].

SCHEME I-1

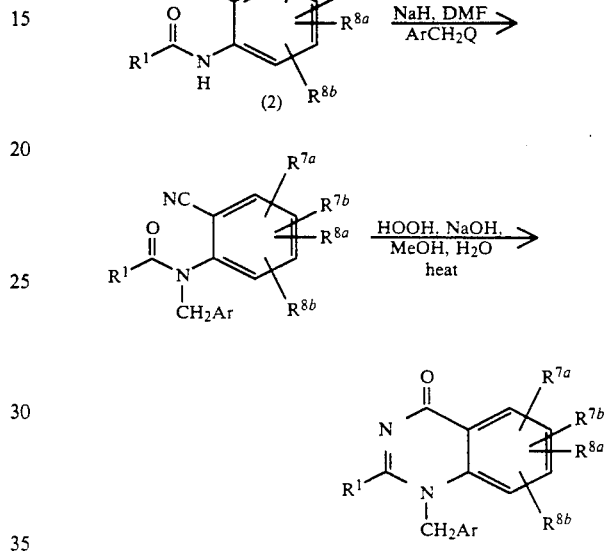

Q = Br, I, OTs, OTf
Ar = is as defined as in the generic structure Formula I

2-Substituted quinazolinones may be prepared from substituted anthranilonitriles as described in the literature and illustrated in Scheme I-2. The appropriately substituted anthranilonitrile is acylated using the requisite acyl chloride then cyclized using basic hydrogen peroxide.[1]

SCHEME I-2

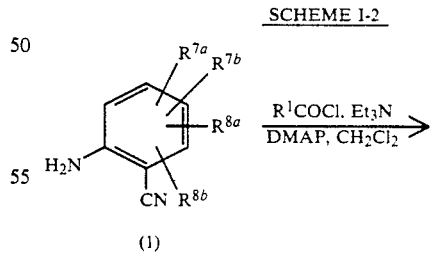

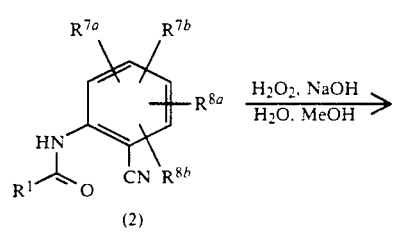

-continued
SCHEME I-2

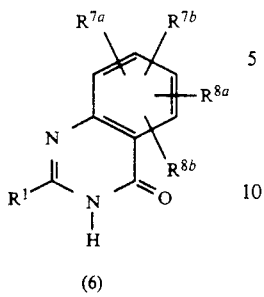

(6)

Scheme I-3 shows an alternate preparation of 2-substituted quinazolinones starting with the corresponding anthranilic acid. The appropriately substituted anthranilic acid is treated with two equivalents of the requisite acyl chloride in DMF with triethylamine and DMAP at 0° C. This is then heated to 110° C. for two hours after which time excess ammonium carbonate is added.[2]

SCHEME I-3

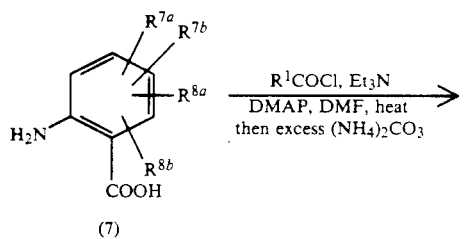

(7)

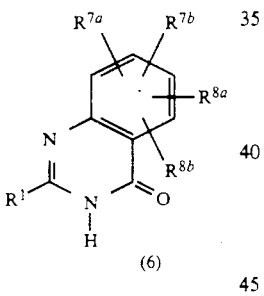

(6)

Scheme I-4 illustrates the general preparation of 2,3-disubstituted quinazolin-4-(3H)-ones of Formula Ia, wherein E is a single bond and $K^1$ is —C(O)—. An appropriately substituted 2-substituted quinazolinone (see Scheme I-2 or Scheme I2 or Scheme I3) is alkylated using sodium hydride and the appropriate alkyl halide (or pseudohalide). This reaction sometimes gives some O-alkylated product, generally less than 20% of the isolated reaction products.

SCHEME I-4

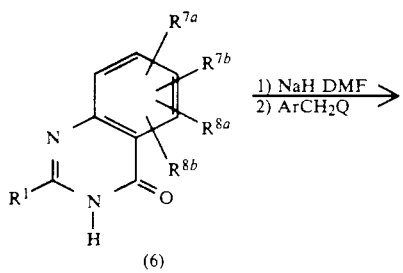

(6)

-continued
SCHEME I-4

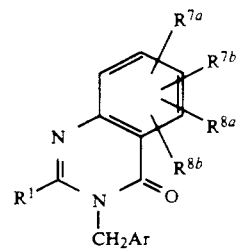

Schemes I-5, I-6, and I-7 provide an alternate route to compounds of Formula Ia, wherein E is a single bond and $K^1$ is —C(O)—.

Two methods for preparing 3,1,4-benzoxazones are illustrated in Scheme I-5. Substituted anthranilic acids may be acylated and cyclized by heating them in DMF with an acyl chloride, triethylamine and DMAP.[3] Alternatively, they may also be prepared by heating an appropriately substituted anthranil with an acyl chloride in pyridine.[4]

The necessary alkyl amine may then be prepared from the alkyl halide (or pseudohalide) using the standard literature procedures (Scheme I-6).[5] Then, the amine and the 3,1,4-benzoxazone are heated together to give the desired 2,3-disubstituted quinazolinone 2 (Scheme I-7).

SCHEME I-5

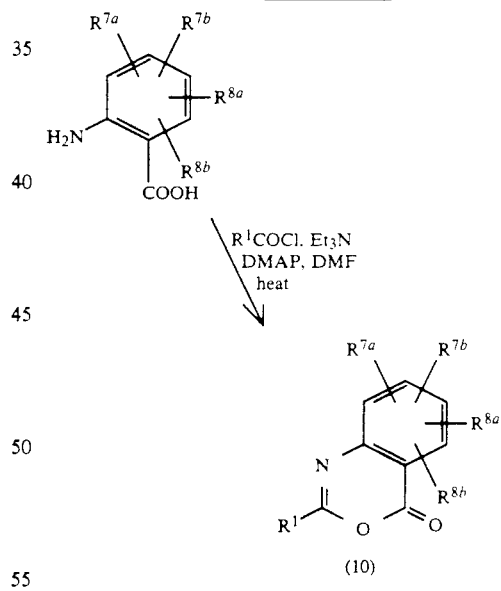

(10)

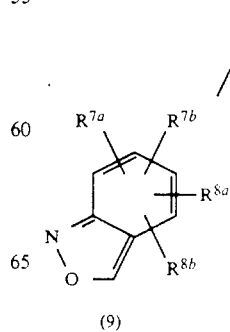

(9)

SCHEME I-6

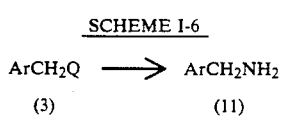

SCHEME I-7

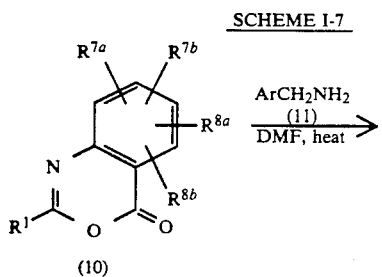

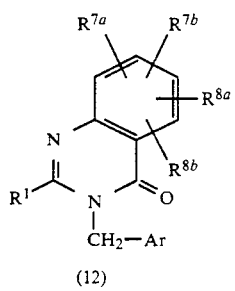

Substituted 2-alkylthioquinazolin-4(3H)-ones wherein $K^1$ is —C(O)— and E is —S— may be prepared from their corresponding substituted anthranilic acids as shown in Scheme I-8. The amine from Scheme I-6 can be converted to its isothiocyanate upon treatment with thiophosgene. This may then be reacted with an appropriately substituted anthranilic acid to give the desired 3-alkyl-2-mercapto-quinazolin-4(3H)-one.[6] A second alkylation of the mercapto group then gives the desired 2-alkylthio-3-alkylquinazolin-4(3H)-one.[7]

SCHEME I-8

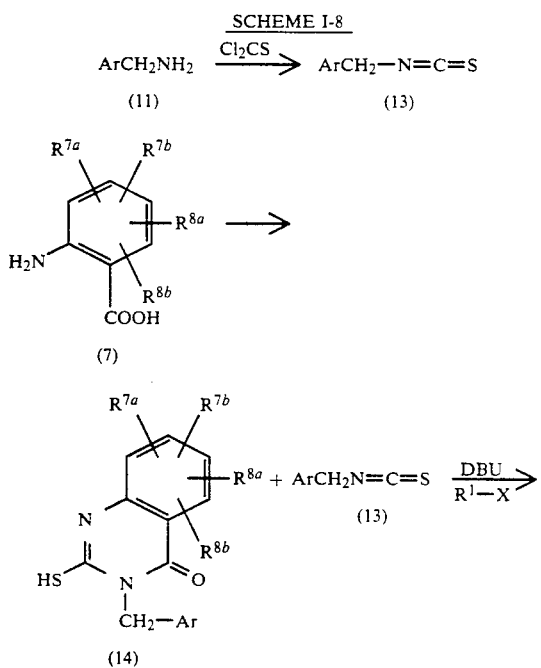

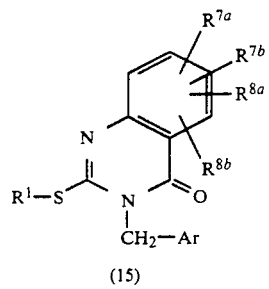

Similarly, 2-alkoxyquinazolin-4(3H)-ones wherein $K^1$ is —C(O)— and E is —O— may be prepared from their corresponding substituted anthranilic acids as shown in Scheme 9.[8] Alkylation with the appropriate alkyl halide according to the methods developed by Lange and Sheibley[9] then gives the final product 17.

SCHEME I-9

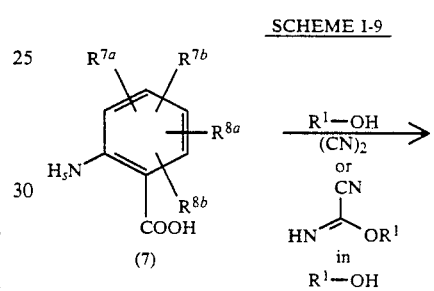

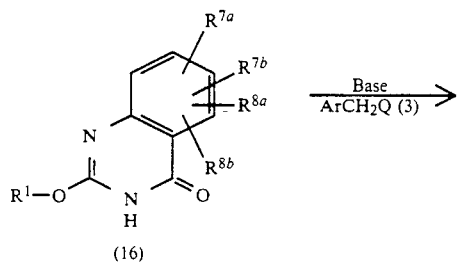

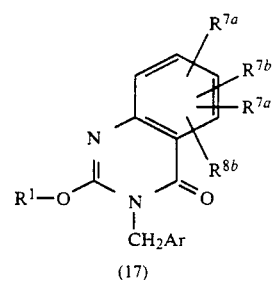

Scheme I-10 illustrates a possible route to the isomeric 1,2-disubstituted quinazolin-4(1H)-ones wherein $J^1$ is —C(O)— and where E is —S— or —O—. An anthranilonitrile can be acylated with an alkyl haloformate or an alkylthiol haloformate.[10] This may then be deprotonated and alkylated with the appropriate alkyl halide to give the intermediate carbamate nitrile shown.[11] Conversion of the intermediate then could occur when the material is treated with basic hydrogen peroxide to yield the desired product 20.

SCHEME I-10

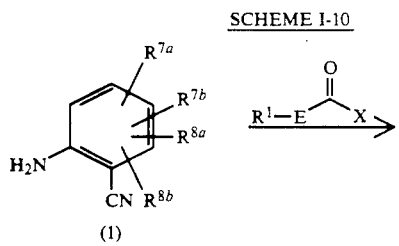

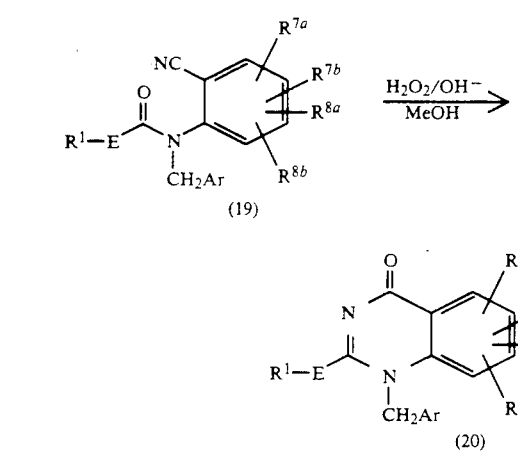

Scheme I-11 illustrates the method by which a 2-amino-3-alkylquinazolinone can be made. The 2-mercaptoquinazolinone (14) shown in Scheme I-8 can be treated with sulfuryl chloride to give the corresponding 2-chloroquinazolinone.[12] Displacement of the chloride with an $R^1$ amine then gives 20 with B=NH.[13]

SCHEME I-11

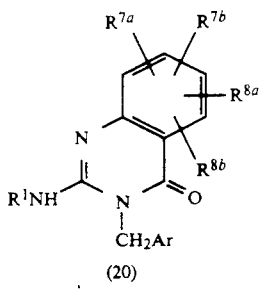

Scheme I-12 illustrates the method by which a 2-amino-1-alkylquinazolinone can be made. The products from Scheme I-10 can be used as a synthetic intermediate if the initial $R^1$ is a protecting group such as benzyl or t-butyl.[14] Deprotection and subjection of the resulting 2-mercapto-1-alkylquinazolinone to the same conditions used in Scheme I-11 will result to the formation of the desired 2-amino-1-alkylquinazolin-4(1H)-one. Alternatively, the sulfide may be displaced directly by an $R^1$ amine as shown in Scheme I-13 ($R^1$—S— and $R^1$—NH$_2$ may or may not have the same $R^1$).

SCHEME I-12

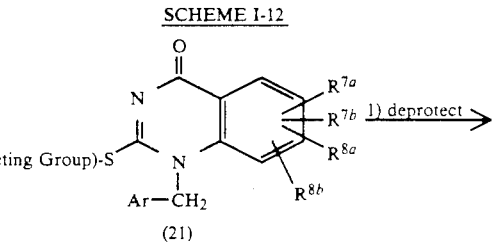

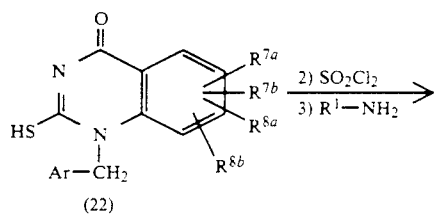

SCHEME I-13

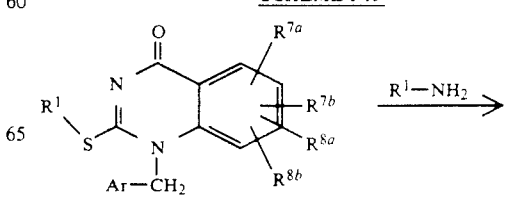

-continued
SCHEME I-13

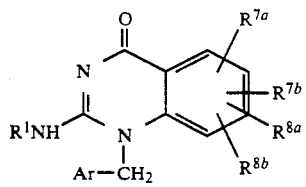

The preparation of quinazolinones of general Formula Ia bearing substituted C-6 amino groups may be accomplished as illustrated in Schemes I-14 through I-16. In order to prepare these derivatives, the amide group of a 6-nitroquinazolin-4(3H)-one is usually first protected with an acid labile protecting group as shown in Scheme I-14. For instance, reaction of the generalized 6-nitroquinazolin-4(3H)-one (24) with a base such as sodium hydride in DMF followed by addition of bis(4-methoxyphenyl)methyl chloride affords the N-protected derivative 25. The nitro group of 25 may be reduced to the amine 26 by reduction with hydrogen over palladium on carbon. The amine (26) may then be reacted with a variety of reagents known to form derivatives of amines such as alkyl- or aryl-carboxylic acid chlorides, chloroformates, sulfonyl and sulfamoyl chlorides, isocyanates and isothiocyanates. Scheme I-14 illustrates the derivatization of amine 26 with a generalized chloroformate to afford substituted carbamates such as 27. The acylation of amine 26 with a chloroformate is best carried out in the presence of a strong base such as sodium hydride to deprotonate the amine. This anion then reacts readily with chloroformates to give the substituted carbamates 27. The carbamate (27) may be isolated, then deprotonated with lithium bis(trimethylsilyl)amide and alkylated to give the N,O-disubstituted carbamates 28. Alternatively, this process may be carried out in one flask by first deprotonating the aniline (i.e. with sodium hydride in DMF), reacting the anion with an acyl halide or chloroformate, then treating the intermediate with an equivalent of a strong base such as lithium bis(trimethylsilyl)amide and finally adding an alkylating agent to obtain 28. The carbamoyl-substituted quinazolinones 27 and 28 may be cleanly deprotected under acidic conditions such as trifluoroacetic acid-anisole to afford the heterocycles 29 and 30 respectively.

SCHEME I-14

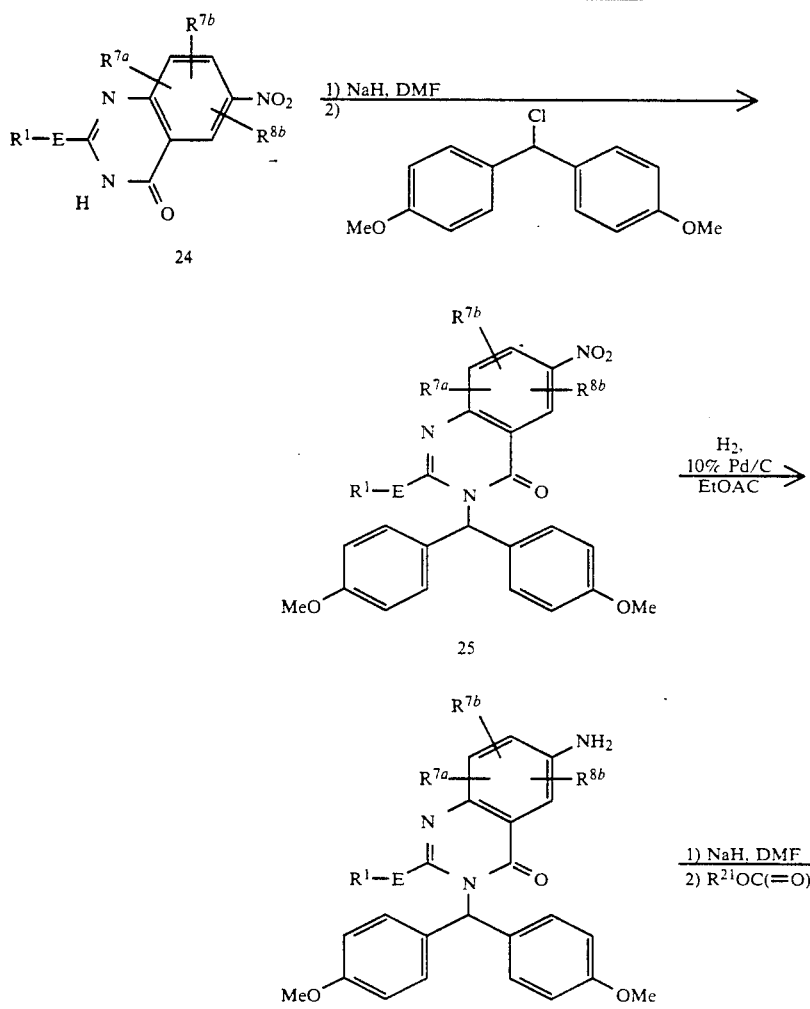

-continued
SCHEME I-14

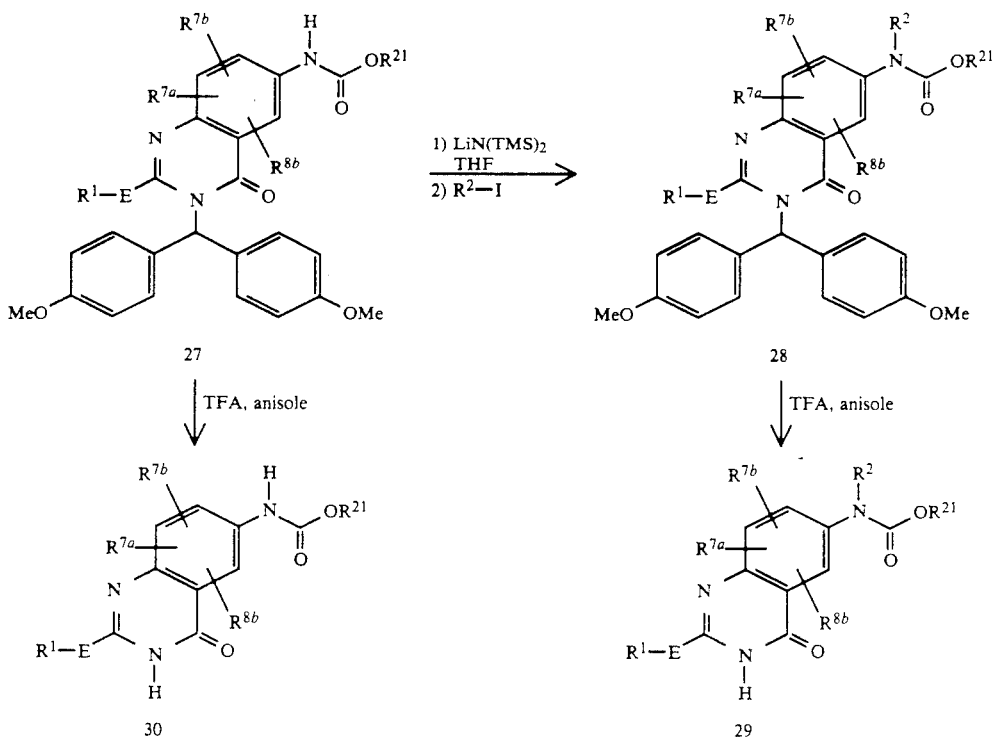

SCHEME I-15

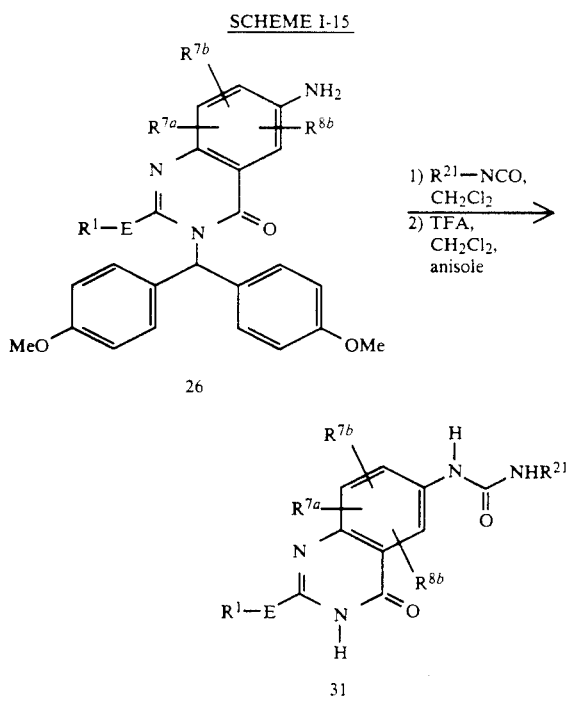

Scheme I-15 illustrates the reaction of amine 25 with isocyanates to give disubstituted ureas (31). Tetrasubstituted and trisubstituted ureas such as 34 and 35 may be prepared from the benzyl carbamate 27 as shown in Scheme I-16. Thus, treatment of 27 with the magnesium salt of a secondary amine formed from the secondary amine and methylmagnesium bromide affords the tri-substituted urea 32. Trisubstituted ureas (32) may be N-alkylated by deprotonation of the remaining hydrogen with lithium bis(trimethylsilyl)amide followed by alkylation with an alkyl iodide to give 33. The urea-substituted quinazolinones 32 and 33 may be cleanly deprotected under acidic conditions such as trifluoroacetic acid-anisole to afford the heterocycles 34 and 35 respectively. The amine 26 (Scheme I-14) may be derivatized or converted to other functional groups using chemical procedures well known to those skilled in the art. After the appropriate 6-substituent has been constructed the protecting group may be removed by treatment with trifluoroacetic acid in the presence of anisole as illustrated in Schemes I-14 through I-16. The heterocycles obtained in this manner may be incorporated into Angiotensin II Antagonists of general Formula Ia as described in Part II.

SCHEME I-16

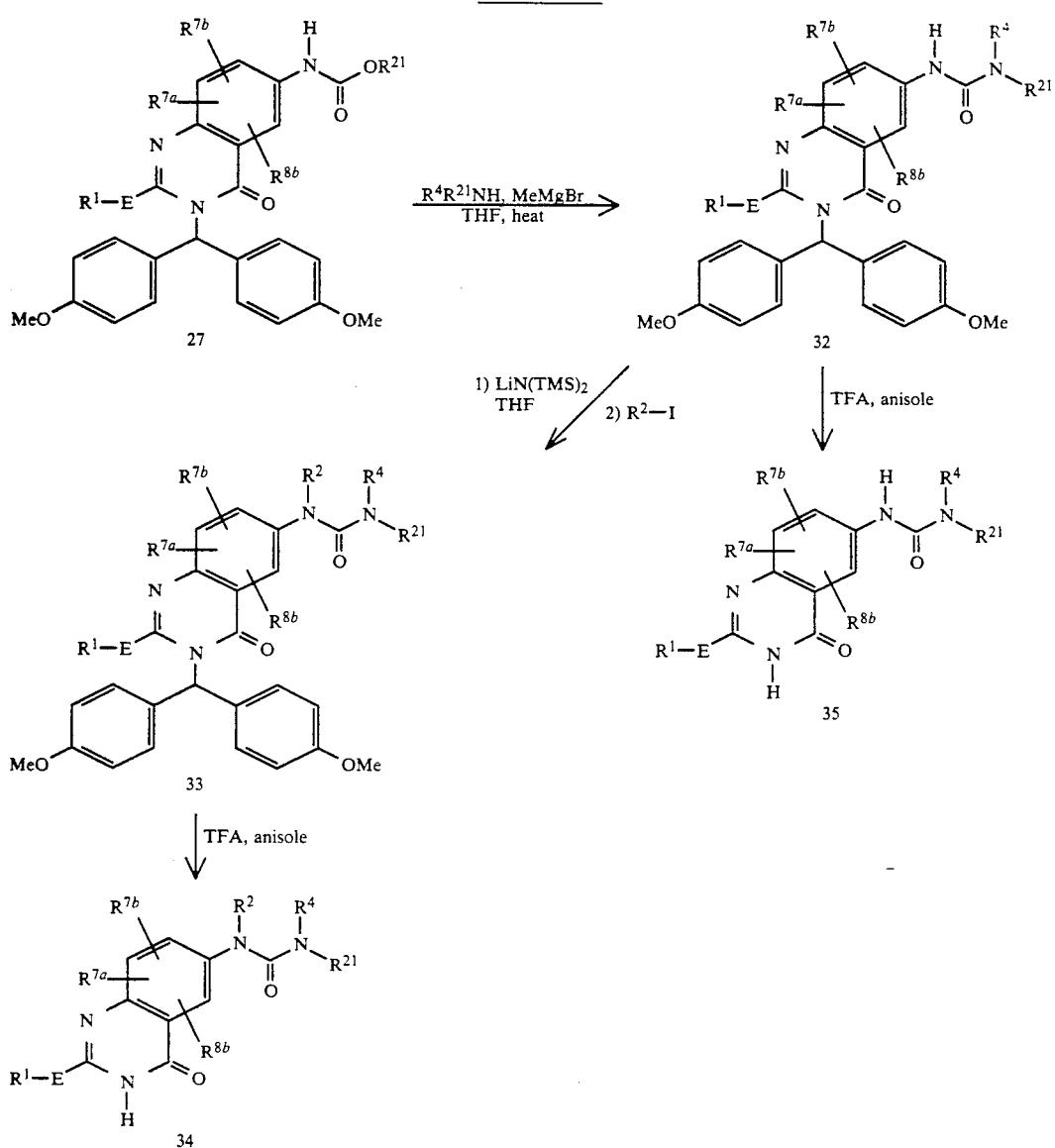

For a general review of the synthesis and reactivity of 2,3-disubstituted pyrido[2,3-d] or [3,4-d] or [3,2-d] or [4,3-d]pyrimidin-4(3H)-ones, see A. R. Katritzky, et al., *Comprehensive Heterocyclic Chemistry*, vol. 3, 201 (1984) and W. J. Irwin, et al., *Advances in Heterocyclic Chemistry*, vol. 10, 149 (1969).

QUINAZOLINONE REFERENCES

[1] E. C. Taylor, R. J. Knopf, A. L. Borror, *J. Am. Chem. Soc.* (1960) 82, 3152. R. L. McKee, M. K. McKee, R. W. Bost, *J. Am. Chem. Soc.* (1946) 68, 1902. A. Khan, R. K. Saksena, *Pharmazie* (1988) 43 H. 12.

[2] M. T. Bogert, W. F. Hand, *J. Am. Chem. Soc.* (1906) 28, 94.

[3] See A. Khan, reference 1. L. A. Errede, J. J. McBrady, H. T. Oien, *J. Org. Chem.* (1977) 42, 656. L. A. Errede, *J. Org. Chem.* (1976) 41 1763. L. A. Errede, H. T. Oien, D. R. Yarian, *J. Org. Chem.* (1977) 42, 12.

[4] K. Wunsch, A. J. Boulton, *Adv. Het. Chem.* (1967) 8. pp 326–9, and references therein. I. R. Gambhir, S. S. Joshi, *J. Ind. Chem. Soc.* (1964) 41, 47.

[5] Bayley, Stranding, Knowles, *Tetrahedron. Lett.* (1978) 3633. Rolla, *J. Org. Chem.* (1982) 47, 4327. Gibson, Bradshaw, *Angew. Chem. Int. Ed. Engl.* (1968) 7, 919.

[6] R. G. Dave, G. S. Mewada, G. C. Amin, *J. Ind. Chem. Soc.* (1960) 37, 595.

[7] J. E. McCarty, E. L. Haines, C. A. VanderWerf, *J. Am. Chem. Soc.* (1960) 82, 964. P. N. Bhargava, P. Ram, *Bull. Chem. Soc. Jap.* (1965) 38, 342. M. R. Chaurasia, A. K. Sharma, *Heterocycles* (1983) 20, 1549. K. Lempert, G. Doleschall, *Chem Ber.* (1963) 96, 1271. H. Singh, K. S. Narang, *J. Ind. Chem. Soc.* (1963) 40, 545. M. S. Dhatt, K. S. Narang, *J. Ind. Chem. Soc.* (1954) 31, 787. M. S. Dhatt, K. S. Narang, *J. Ind. Chem. Soc.* (1954) 31, 864. D. S. Bariana, H. S. Sachdev, K. S. Narang, *J. Ind. Chem. Soc.* (1955) 32, 647.

[8] Griess, *Ber. Deut. Chem. Ges.* (1869) 2, 415.

[9] N. A. Lang, F. E. Sheibley, *J. Am. Chem. Soc.* (1933) 55, 1188.

[10] H. B. Milne, S. L. Razniak, R. P. Bayer, D. W. Fish, *J. Am. Chem. Soc.* (1960) 82, 4582. E. J. Corey, M. G. Bock, A. P. Kozikowski, A. V. R. Rao, D. Floyd, B. Lipshsutz, *Tetrahedron Lett.* (1978) 1051. M. Bergmann, L. Zervas, *Ber.* (1932) 65 1192.

[11] R. L. Dannley, M. Lukin, *J. Org. Chem.* (1957) 22, 268. R. Zibuck, N. J. Liverton, A. B. Smith, *J. Am. Chem. Soc.* (1986) 10,8 2451.

[12] D. J. Brown, *Fused Pyrimidines*, Part I Quinazolines, (1967), J. Wiley & Sons, p. 222.

[13] D. J. Brown, *Fused Pyrimidines, Part I Quinazolines*, (1967), J. Wiley & Sons, p. 323.

[14] T. W. Greene, *Protective Groups in Organic Synthesis*, (1981), J. Wiley & Sons, pp. 193–217.

B. Preparation of triazolinones, triazolinethiones and triazolinimines (Formula Ib)

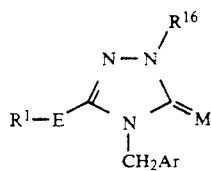

The compounds of Formula Ib can be prepared by a variety of methods typified by those described below in Schemes I-17 to I-28. General synthetic methods for 2,4,5-trisubstituted-1,2,4-triazolin-3(4H)-ones and -triazolin-3(4H)-thiones are discussed in books or review articles such as:

(1) C. Temple and J.A. Montgomery, "Triazoles: 1,2,4" (Vol. 37 of *The Chemistry of Heterocyclic Compounds*, A. Weissberger and E. C. Taylor, eds.), Wiley-Interscience, New York, 1981, pp. 365–442.

(2) J. B. Polya, *Comprehensive Heterocyclic Chemistry. The Structure, Reactions, Synthesis and Uses of Heterocyclic Compounds*, A. R. Katritzky and C. W. Rees, eds., Vol. 5, Pergamon Press, Oxford, 1984, pp. 733–790.

(3) J. H. Boyer, *Heterocyclic Compounds*, R. C. Elderfield, ed., Vol. 7, John Wiley & Sons, New York, 1961, pp. 384–461.

In general, the compounds of Formula Ib are constructed in such a way that $N^1$ and $N^2$ of the triazole ring are derived from hydrazine or a hydrazine derivative, while $N^4$ of the triazole and the 4-(arylmethyl) substituent are derived directly or indirectly from a suitably substituted benzylamine (or isocyanate or isothiocyanate) or from a benzyl halide (or methanesulfonate, p-toluenesulfonate, etc.).

Although the Reaction Schemes described below are reasonably general, it will be understood by those skilled in the art of organic synthesis that one or more functional groups present in a given compound of Formula Ib may render the molecule incompatible with a particular synthetic sequence. In such a case an alternative route, an altered order of steps, or a strategy of protection and deprotection may be employed. In all cases the particular reaction conditions (including reagents, solvent, temperature, and time) should be chosen so that they are consistent with the nature of the functionality present in the molecule.

The Reaction Schemes below have been generalized for simplicity. It is to be understood that the "$ArCH_2$" substituent present at $N^4$ of the triazole derivatives or in their precursors is any substituted arylmethyl moiety consistent with the definition of the $N^4$ substituent in Formula I or which may be transformed to such a grouping either before or after the assembly of the triazole ring system. Such transformations may involve protection and/or deprotection steps, as described above in the "General Methods" section or other modifications. It is also to be understood that in most of the Reaction Schemes, the "$ArCH_2$" (Ar=aryl) substituent is consistent with the definition of Formula I.

It is further to be understood that in the generalized schemes below, unless specified otherwise, the $R^1$ and $R^{16}$ groups represent functionalized or unfunctionalized alkyl, aryl, heteroaryl, aralkyl, and the like. The moiety, $R^{16}Q$, represents an alkylating agent in which $R^{16}$ is typically a functionalized or unfunctionalized alkyl or aralkyl group, while Q is a leaving group such as chloro, bromo, iodo, methanesulfonate, or p-toluenesulfonate. In structures showing an "X" group double-bonded to a carbon atom (as in 22 and products derived therefrom), M is O or S.

REACTION SCHEME I-17

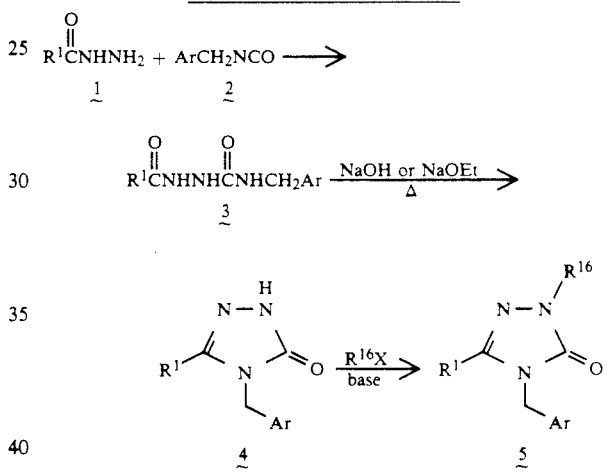

M = 0

One of the most widely used routes to 2,4,5-trisubstituted-2,4-dihydro-3H-1,2,4-triazol-3-ones (2,4,5-trisubstituted-1,2,4-triazolin-3(4H)-ones) is shown in Reaction Schemes I-17 in its adaptation for the synthesis of compounds of Formula Ib. Reaction of a carboxylic acid hydrazide 1 (readily obtained from the corresponding ester) with the appropriate arylmethyl isocyanate 2 gives the 1-acyl-4-(arylmethyl)semicarbazide 3. The isocyanate 2 itself is obtainable by well-known methods from various sources, including the (arylmethyl)amine (by phosgene treatment), the arylmethyl halide (by treatment with cyanate anion), and the arylacetic acid or derivative (via Curtius rearrangement of the acyl azide). Upon heating in the presence of hydroxide or alkoxide, cyclization of 3 to the triazolinone 4 occurs. Finally, in the presence of a base (e.g., sodium hydride, sodium ethoxide, sodium hydroxide, or potassium carbonate), 4 is converted to the trisubstituted triazolinone 5 on treatment with a suitable alkylating agent $R^{16}Q$, where $R^{16}$ is alkyl, aralkyl, etc., and Q is bromo, iodo, chloro, methanesulfonate, p-toluenesulfonate, and the like. Such reaction pathways have been described by D. L. Temple, Jr., and W. G. Lobeck, Jr., U.S. Pat. No. 4,487,773 (1984), R. E. Gammans, D. W. Smith, and J.

P. Yevich, U.S. Pat. No. 4,613,600 (1986), and (in part) H. Gehlen and W. Schade, *Liebigs Ann. Chem.*, 675, 180 (1964), G. Palazzo, U.S. Pat. No. 3,857,845 (1974), and K. H. Hauptmann and K. Zeile, British Patent 971,606 (1964). A modified approach to an intermediate of type 3 and its subsequent cyclization to a triazolinone analogous to 4 have been reported by H. Hrebabecky and J. Beranek, *Collect. Czech. Chem. Commun.*, 50, 779 (1985).

REACTION SCHEME I-18

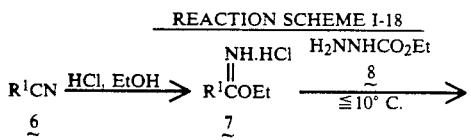

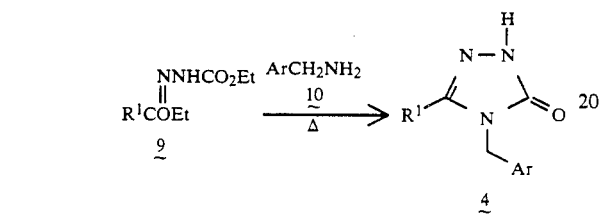

M = 0
R$^{16}$ = H

A highly useful alternative route to 4 is shown in Reaction Scheme I-18. This approach has been described by M. Pesson, S. Duplin, and M. Antoine, *Compt. Rend.*, 253, 285 (1961) and R. Un and A. Ikizler, *Chim. Acta Turc.* 3, 113 (1975). Addition of ethyl carbazate (8) to the imidate 7 (which is readily prepared from the corresponding nitrile 6) yields an adduct 9, which can be converted to the triazolinone 4 on heating with the (arylmethyl)amine 10 (typically at temperatures from 70°-150° C.). As in Reaction Scheme I-17, 4 can be alkylated to give the trisubstituted triazolinone 5.

REACTION SCHEME I-19

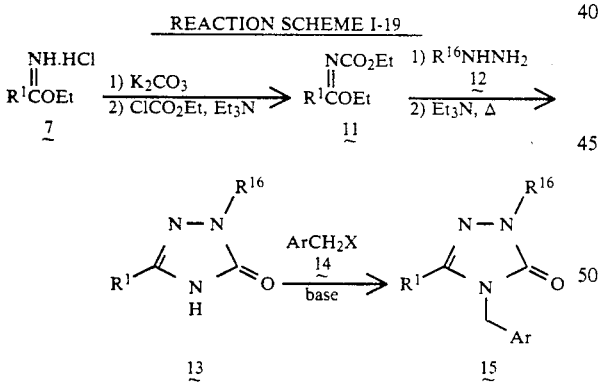

R$^{16}$ = aryl
M = 0

The procedures of Reaction Schemes I-17 and I-18 are not suitable for the introduction of most aryl or heteroaryl substitutents at N$^2$. In contrast, the procedures of Reaction Schemes I-19 to I-22 are especially well suited for the synthesis of compounds of Formula Ib having aryl or heteroaryl substitutents at N$^2$, since the triazolinone ring is constructed with the N$^2$-substitutent in place, whereas the N$^4$-substitutent is introduced subsequently by alkylation. Reaction Scheme I-19 presents a route patterned after that reported by K. Yabutani, K. Taninaka, M. Kajioka, K. Takagi, H. Matsui, K. Sutoh, and M. Yamamoto, European Patent Application 220, 952 (1987). The N-carbethoxy imidate 11 (obtained by reaction of 7 with ethyl chloroformate) is treated with an arylhydrazine 12 (or analog), typically at about 40°-50° C.,) in the presence of a tertiary amine such as triethylamine which effects cyclization to the triazolinone 13. In the presence of a suitable base (e.g., sodium hydride, sodium alkoxide, sodium hydroxide) treatment of 13 with the appropriate ArCH$_2$Q, where Q=bromo, iodo, chloro, methane-sulfonate, p-toluenesulfonate, and the like, yields the N$^4$-alkylated product 15. A variant of the method using a thioimidate has been described by M. Kajioka, H. Kurono, K. Okawa, and M. Harada, U.S. Pat. No. 4,318,731 (1982).

REACTION SCHEME I-20

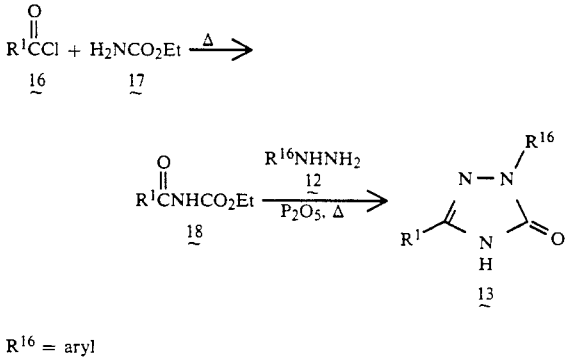

R$^{16}$ = aryl

An alternative route to the N$^2$-substituted triazolinone intermediate 13 is shown in Reaction Scheme I-20. This chemistry has been described by T. N. Ghosh and M. V. Betrabet, *J. Indian Chem. Soc.*, 7, 899 (1930), S. Bellioni, *Ann. Chim. (Rome)*, 52, 187(1962), G. Pallazzo and G. Picconi, *Boll. Chim. Farm.*, 105, 217 (1966), and British Patent 1,021,070 (1966). An acid chloride 16 is heated with urethane (17) typically at 80°-100° C.), to give the acylurethane 18. Reaction of 18 with an arylhydrazine 12 and phosphorous pentoxide (usually in toluene or xylene at reflux) gives 13, which can then be further alkylated on N$^4$ as in Reaction Scheme I-19. A (thioacyl)urethane modification of this pathway has been reported by D. L. Temple, Jr., and W. G. Lobeck, Jr., U.S. Pat. No. 4,487,773 (1984).

REACTION SCHEME I-21

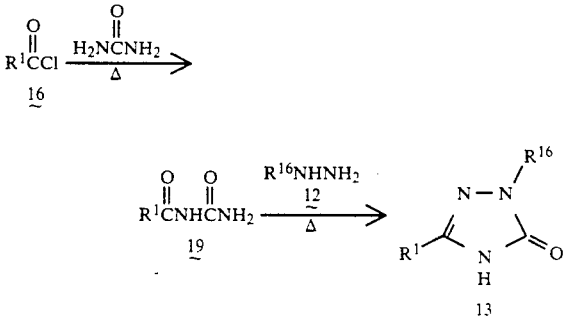

R$^{16}$ = aryl
M = 0

A variation of Reaction Scheme I-20, Shown in Reaction Scheme I-21, has been described by P. Gold-Aubert, D. Melkonian, and L. Toribio, *Helv. Chim. Acta*, 47, 1188 (1964) and A. L. Langis, U.S. Pat. No. 3,499,000 (1970). The readily prepared acylurea 19 upon heating with an arylhydrazine 12 (at about 150°-200° C.) is converted to the triazolinone intermediate 13.

REACTION SCHEME I-22

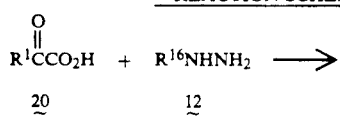

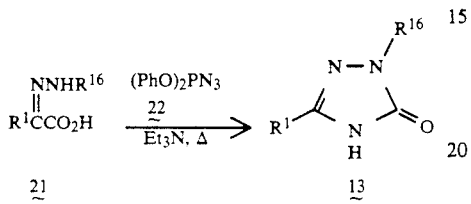

$R^{16}$ = aryl
$M$ = O

In a quite different approach (Reaction Scheme I-22), L. Maravetz, U.S. Pat. No. 4,705,557 (1987) and G. Theodoridis, International Patent Application WO87/03782 (1987) disclose condensing an α-keto acid 20 with the arylhydrazine 12 to give derivatives such as 21, which can be converted to the triazolinone intermediate 13 by heating with diphenylphosphoryl azide and triethylamine (typically at 75°-115° C.). In the last step, an intermediate acyl azide loses nitrogen and undergoes the Curtius rearrangement to an isocyanate, which undergoes ring closure. As shown in Reaction Scheme I-19, 13 can then be alkylated on $N^4$ to give the trisubstituted triazolinone 15.

REACTION SCHEME I-23

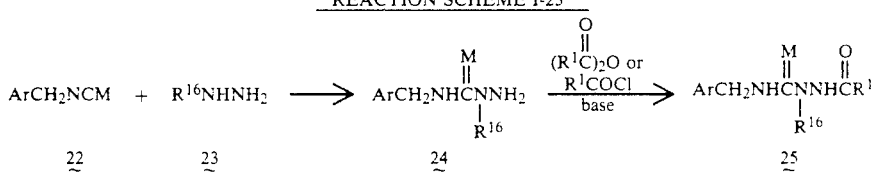

M = O or S

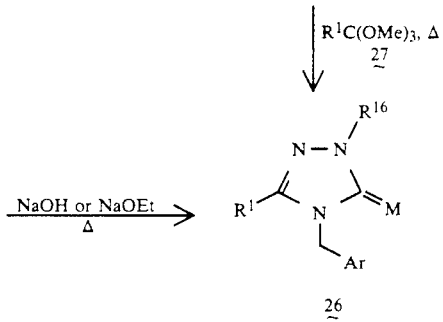

2,4,5-Trisubstituted-2,4-dihydro-3H-1,2,4-triazole-3-thiones (2,4,5-trisubstituted-1,2,4-triazolin-3(4H)-thiones) cannot generally be prepared by routes analogous to those in Reaction Schemes I-17 to I-22 because of the propensity for alkylation to occur on sulfur rather than on the open ring nitrogen. It is thus preferable to have all of the substituents in place at the time of the ring closure to form the heterocycle. As shown in Reaction Scheme I-23, for certain $R^{16}$ groups (e.g., $R^{16}$=CH$_3$), reaction of the hydrazine derivative 23 with the appropriate isocyanate or isothiocyanate 22 yields the 2,4-disubstituted semicarbazide or thiosemicarbazide 24. Acylation of 24 gives 25, which can be cyclized upon heating with hydroxide or alkoxide to give the trisubstituted triazolinone or triazolinethione 26. This approach has been detailed by J. M. Kane and F. P. Miller, U.S. Pat. No. 4,775,688 (1988) and G. F. Duffin, J. D. Kendall, and H. R. J. Waddington, *J. Chem. Soc.*, 3799 (1959). Alternative methods of ring closure, such as heating 24 with the orthoester 27, can also be utilized.

REACTION SCHEME I-24

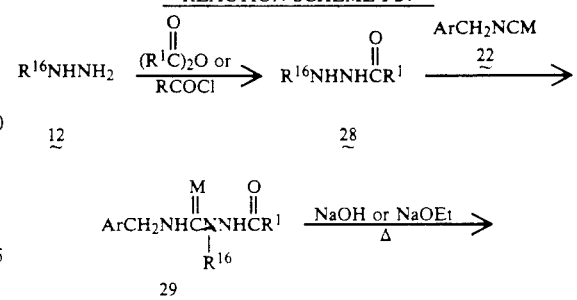

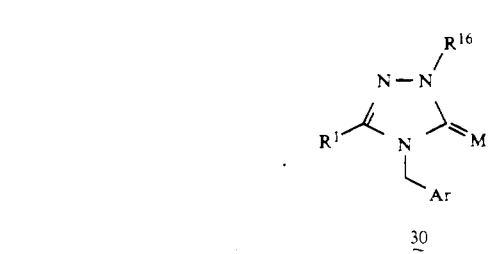

$R^{16}$ = aryl

In Reaction Scheme I-24, acylation of an aryl- or heteroaryl hydrazine gives 28, which can be reacted with the isocyanate or isothiocyanate 22 to yield the 1-acyl-2,4-disubstituted-semicarbazide or -thiosemicarbazide 29. Cyclization of 29 upon heating with hydroxide or alkoxide affords the triazolinone or triazolinethione 30. This chemistry has been described by H. Gehlen and W. Schade, *Liebigs Ann. Chem.*, 675, 180 (1964).

REACTION SCHEME I-25

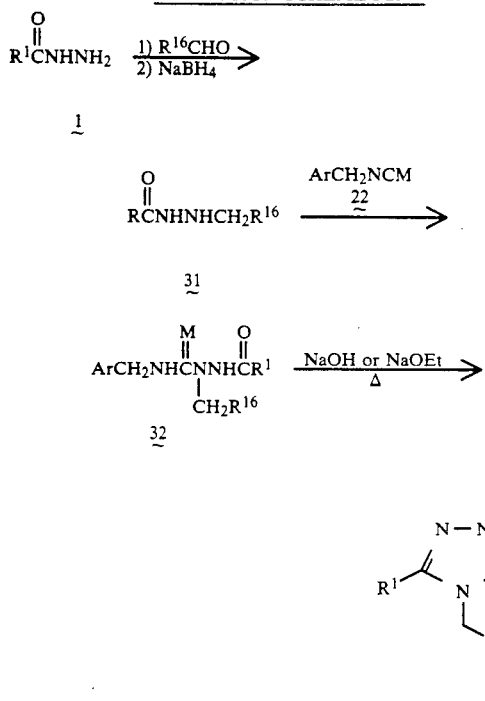

The method of F. Russo, M. Santagati, and G. Pappalardo [*Ann. Chim. (Rome)*, 62, 351 (1972)] (Reaction Scheme I-45) is useful for the synthesis of trisubstituted triazolinones and triazolinethiones having benzylic substituents at $N^2$. Treatment of a hydrazide 1 with an aromatic or heteroaromatic aldehyde followed by reduction with sodium borohydride gives the substituted hydrazide 31. Reaction of 31 with the isocyanate or isothiocyanate 22 affords the semicarbazide or thiosemicarbazide derivative 32, which is cyclized to the triazolinone or triazolinethione 33 upon heating with hydroxide or alkoxide.

REACTION SCHEME I-26

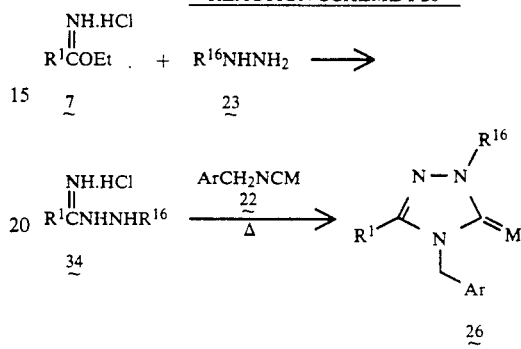

M = O or S

In another approach (Reaction Scheme I-26), imidate 7 is treated with a substituted hydrazine 23 (especially an aryl or heteroaryl hydrazine) to give the amidrazone 34. Heating 34 with the isocyanate or isothiocyanate 22 gives the triazolinone or triazolinethione 26. Syntheses of this type have been reported by M. Santus, *Acta Pol. Pharm.*, 293 (1980); T. Bany, *Rocz. Chem.*, 42, 247 (1968); and, T. Bany and M. Dobosz, *Ann. Univ. Mariae Curie-Sklodowska, Sect. AA*, 26/27, 23 (1971).

REACTION SCHEME I-27

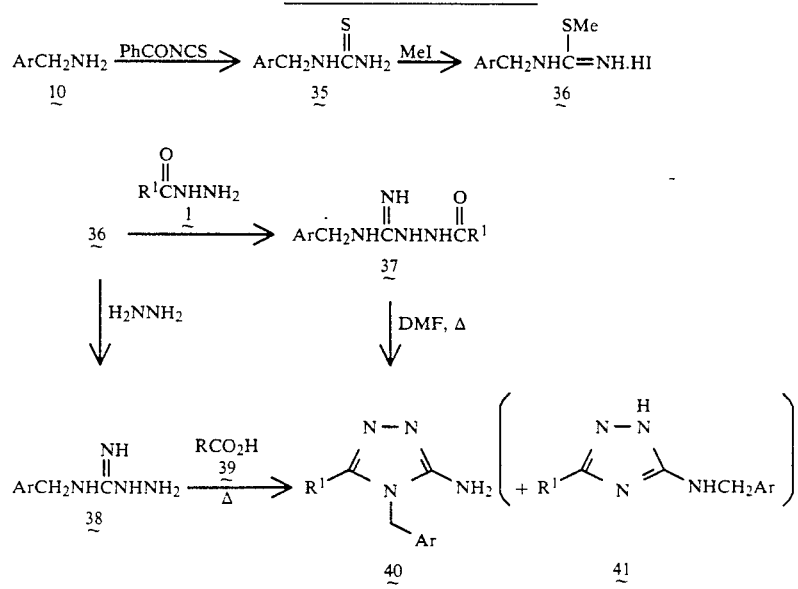

REACTION SCHEME I-27
-continued

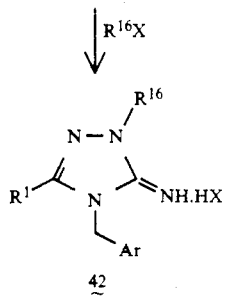

42

A route to 2,4,5-trisubstituted-2,4-dihydro-3H-1,2,4-triazol-3-imines (2,4,5-trisubstituted-1,2,4-triazolin-3(4H)-imines is outlined in Reaction Scheme I-27. Reaction of the (arylmethyl)amine 10 with benzoyl isothiocyanate (or by other means) gives the substituted thiourea 35, which is methylated to prepare the isothiourea derivative 36. Compound 36 can be transformed to the acylaminoguanidine 37 by reacting with the hydrazide 1 or to the aminoguanidine 38 by reacting with hydrazine. Ring closure of 37 by heating in DMF or cyclization of 38 with carboxylic acid 39 at elevated temperature affords the aminotriazole 40, which can be separated from the isomer 41. Such pathways have been described by G. J. Durant, G. M. Smith, R. G. W. Spickett, and S. H. B. Wright, *J. Med. Chem.*, 9, 22 (1966) and E. Akerblom, *Acta Chem. Scand.*, 19, 1135 (1965). Finally, alkylation of 40 with the appropriate Ar—CH$_2$—Q (where Q is a leaving group such as iodo, bromo, chloro, p-toluenesulfonate, or methanesulfonate) leads to the triazolinimine 42, which can be separated from any other isomers or by-products formed during the reaction. This method has been described by E. B. Akerblom and D. E. S. Campbell, *J. Med. Chem.*, 16, 312 (1973).

REACTION SCHEME I-28

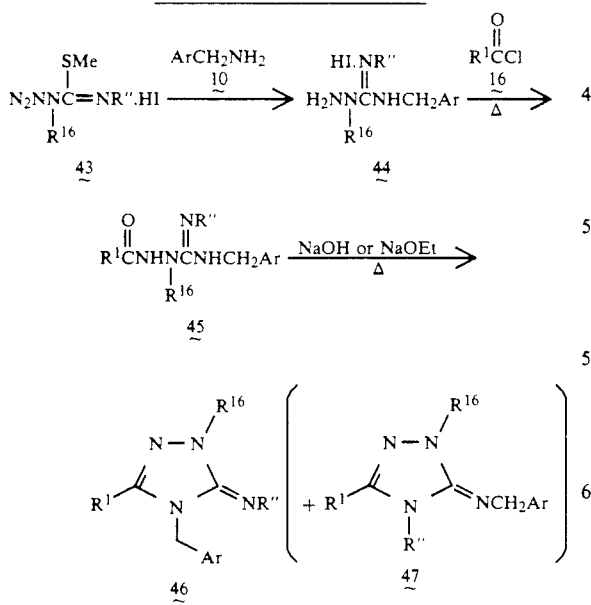

The route shown in Reaction Scheme I-28 utilizes chemistry reported by E. Akerblom, *Acta Chem. Scand.*, 19, 1135 (1965). The substituted isothiourea 43 is treated with amine 10 to give the aminoguanidine derivative 44. Acylation of 44 with the acid chloride 16 provides the intermediate 45, which can be cyclized by heating with hydroxide or alkoxide. The desired triazolinimine 46 is separated from the isomeric product 47.

C. Preparation of Pyrimidinones (Formula Ic)

The compounds of Formula Ic wherein either J$^2$ or K$^2$ is —C(O)— are synthesized as illustrated in Schemes I-49 to I-60 below.

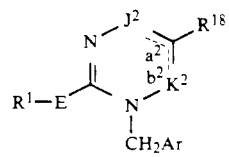

Pyrimidinones of formula Ic (wherein J$^2$ is —C(O)—) substituted in the 1,2,5, and 6-positions may be synthesized as shown in Scheme I-29. Amidines with an R$^1$ substituent may be reacted with a β-carbonyl ester to give a 4-hydroxypyrimidine. Conversion of the hydroxy group to a chloride then to an amine can be achieved by first treating the 4-hydroxypyrimidine with POCl$_3$ then with ammonia.$^1$ Reaction of the 4-aminopyrimidine with the appropriate alkyl followed by treatment with aqueous hydroxide gives the substituted pyrimidin-4(1H)-one.

SCHEME I-29

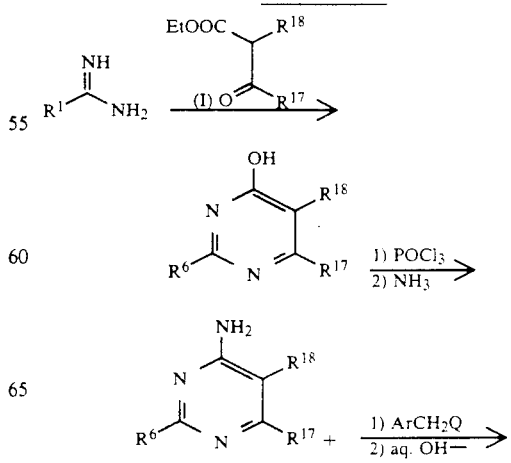

SCHEME I-29 -continued

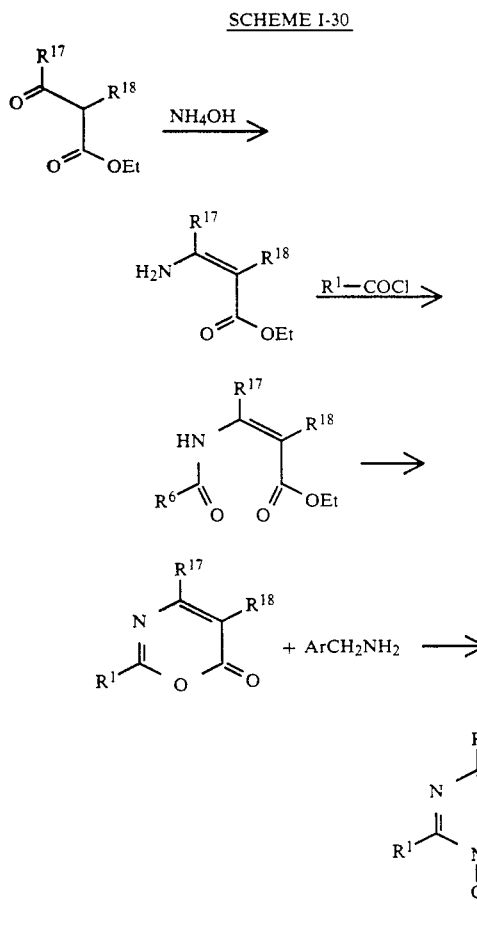

Q is a leaving group (—Cl, —Br, —I, —OTs, etc).

Scheme I-30 provides the method by which the isomeric (wherein $K^2$ is —C(O)—) 2,3,5, and 6-substituted pyrimidinones may be synthesized. A β-carbonyl ester is converted into its corresponding β-aminocrotonate with ammonia.[3] This is then acylated with an $R^1$-containing acyl chloride ($R^1$COCl) and cyclized to a 3,1-oxazin-4-one. When the 3,1-oxazin-4-one is reacted with the substituted benzylamine, the desired fully substituted pyrimidinone 4 results.[4]

SCHEME I-30

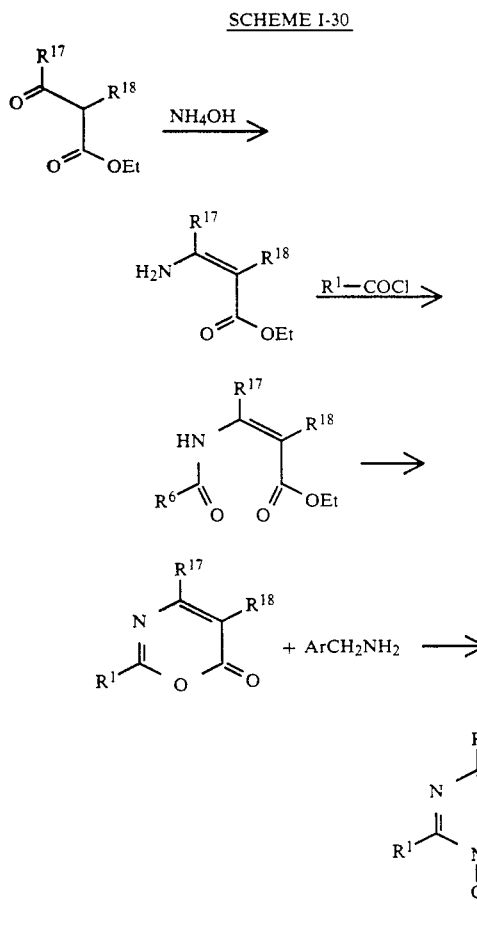

Alternatively, Scheme I-31 shows how an $R^6$ imidate may be converted to an amidine with the substituted benzylamine, followed by treatment with an appropriately substituted α-carbonyl ester to give the desired pyrimidinone 4.[5]

SCHEME I-31

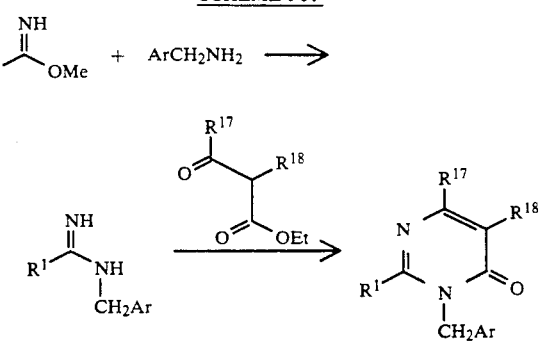

A third alternative is illustrated in Scheme I-52. A simple amidine can be reacted with an appropriately substituted β-carbonyl ester to give the 3-unsubstituted pyrimidinone. This can then be alkylated at the 3-position with KOH in methanol (or with NaH in DMF) and the appropriately substituted alkyl halide to give 4.

SCHEME I-32

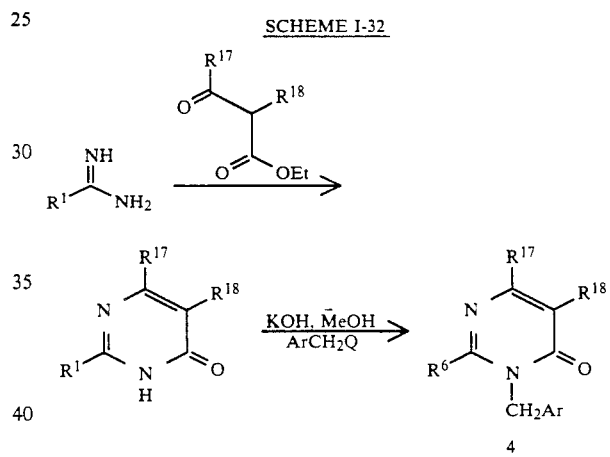

Scheme I-33 illustrates the general synthesis of pyrimidinones of Formula Ic in which E is a sulfur atom. Thiourea when condensed with a β-carbonyl ester gives the 2-thiouracil. This can be bis-trimethylsilylated using hexamethyldisilazane, then alkylated sequentially on the 1-nitrogen atom and then on the sulfur atom using chemistry developed by H. Vorbruggen an P. Strehlke.[6] By this method, one can then obtain compounds of Formula Ic wherein $J^2$ is —C(O)— and E is a sulfur atom.

SCHEME I-33

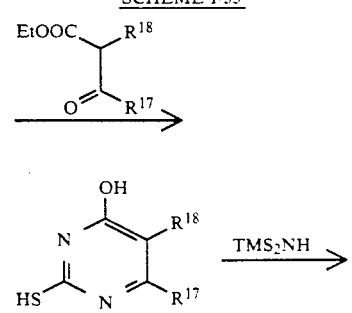

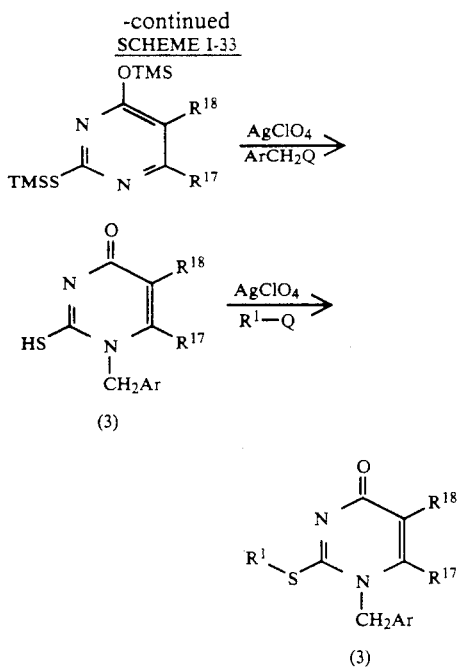

Q is Br, Cl, I, F, OTs, OTf, etc.

The isomeric 2,3-dialkylated thiouracils may be synthesized as shown in Scheme I-34. Thiourea can be condensed with an appropriately substituted β-carbonyl ester to give the 5,6-disubstituted-2-thiouracil.[7] This may then be alkylated sequentially at the sulfur with an $R^1$ halide, and then at the nitrogen atom with an appropriately substituted alkyl halide to give the desired tetrasubstituted pyrimidinone 4.

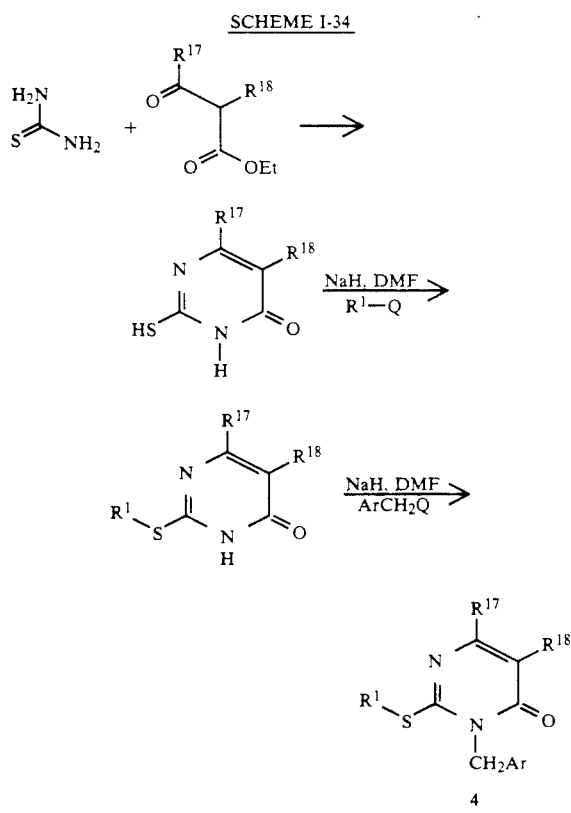

PART II: Preparation of substituted benzyl derivatives of the general Formula I Preparation of compounds of Formula I starting from the heterocycles or benzyl-substituted heterocycles described in Part I is illustrated in the following Schemes and descriptions.

The synthesis of Angiotensin II Antagonists incorporating a substituted benzyl group as shown in Formulas Ia through Ic may be accomplished by two general approaches. In the more convergent approach, a heterocyclic compound (as described in Part I) is deprotonated with a base and alkylated on a nitrogen atom with a benzylic halide or pseudohalide ("Ar—CH$_2$Q") bearing the appropriate substituents $R^9$, $R^{10}$, $R^{11}$, $R^{12}$, X, Y and Z, which leads directly to AII Antagonists described by Formulas Ia to Ic. Following the alkylation of the heterocycle, it may be necessary to perform additional synthetic steps such as ester hydrolysis or the removal of protecting groups in order to complete the preparation of the desired product. For the synthesis of certain derivatives, the alkylation of the heterocyclic compound may be performed with a substituted benzyl halide or pseudohalide which contains a subset of the desired substituents (e.g. $R^9$, $R^{10}$ and X). In these cases, the alkylation step is then followed by additional reactions which are required to assemble the substituted benzyl element of the AII Antagonist. In an alternative approach, compounds with structures described by Formulas Ia through Ic may be synthesized in a linear fashion from a benzyl element which is introduced at the beginning of, or during the preparation of the heterocyclic moiety. Examples of the preparation of Angiotensin II Antagonists described by Formulas Ia-Ic by each of these major approaches are illustrated in the following schemes.

The preparation of the quinazolinone derivative of Formula Ia wherein: $K^1$=—C(O)—, $J^1$ and L are connected together to form a 6-carbon aromatic ring substituted with a methyl group at position 6, E is a single bond, $R^1$ is n-butyl, $R^9$, $R^{10}$, $R^{11}$ are hydrogen, X=O, Y=a single bond, Z=CO$_2$H and $R^{12}$ is phenyl appears in Scheme II-1 and in Example 1 of the Experimental section. Deprotonation of p-cresol (1) with a strong base such as potassium hydride in DMF in the presence of an appropriate crown ether such as 18-crown-6, followed by the addition of methyl 2-bromophenylacetate (2) affords the 2-phenoxy substituted phenylacetic ester 3. Reaction of ester 3 with N-bromosuccinimide (CCl$_4$ reflux, AIBN catalyst), effects benzylic bromination providing the alkylating agent 4. Deprotonation of 2-butyl-6-methylquinazolin-4(1H)-one (5) with sodium hydride in DMF followed by the addition of the alkylating agent 4, results in a mixture of the products of alkylation at the two nitrogen and the oxygen atoms. The desired product (6) in which alkylation has occured on the nitrogen at position 3 is the predominant product, and may be purified from the reaction mixture by chromatographic methods or fractional recrystallization. Alkaline hydrolysis of the ester group of 6 affords the AII Antagonist 7 of Formula Ia.

SCHEME II-1

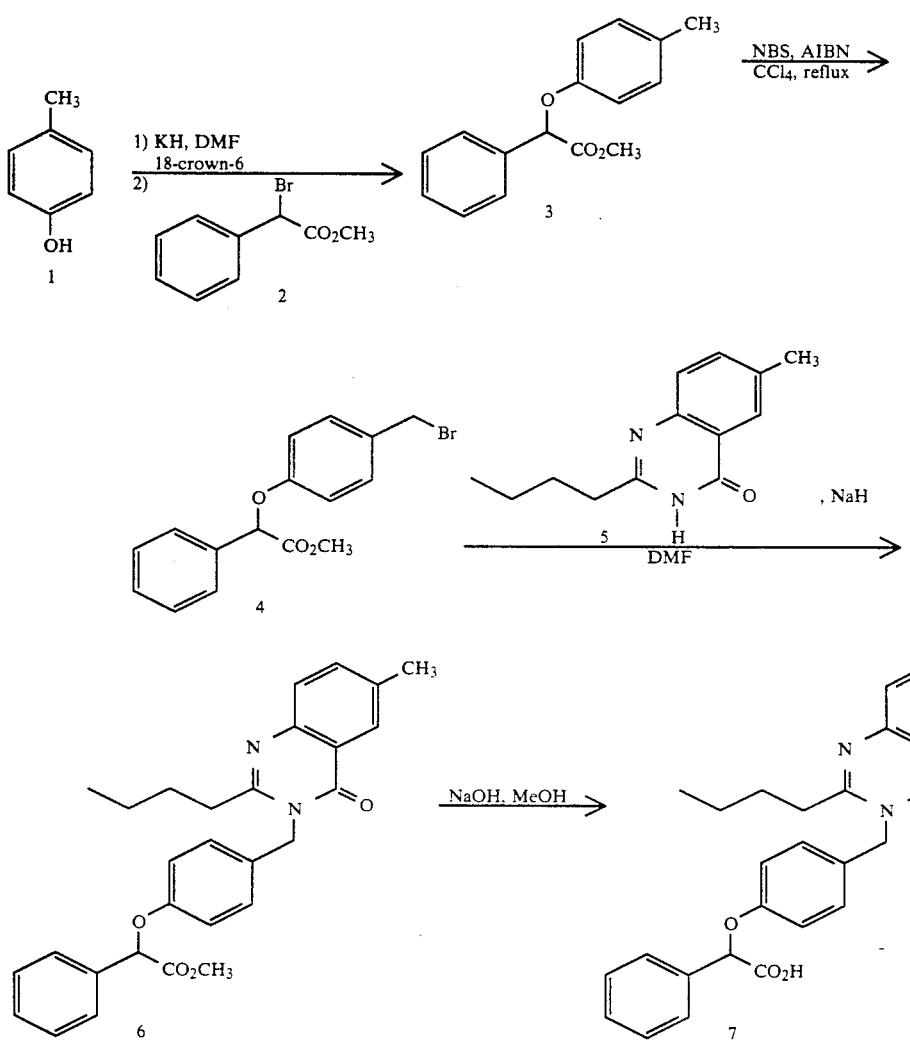

The synthesis of Angiotensin II Antagonists incorporating a substituted benzyl element defined by Formulas Ia–Ic may also be accomplished by the alkylation reaction of a heterocycle (as described in Part I) with a benzylic intermediate bearing a subset of the desired substituents. For instance when it is desired to allow $R^9$ and $R^{10}$ to be hydrogen, alkylation of heterocycle (5) in the presence of a base with 4-benzyloxybenzyl chloride affords the protected phenol 8 as shown in Scheme II-2. The benzyl ether is next removed by hydrogenolysis using hydrogen and an appropriate catalyst such as Pd/C, Pd(OH)$_2$/C or Pt/C which affords the intermediate phenol 9. The phenolic proton is then deprotonated with a base such as sodium hydride in DMF, and the phenolate is alkylated with a 2-bromophenylacetic ester such as 10 to provide ester 11. Finally, the ester is hydrolyzed and the carboxylic acid (12) of Formula Ia where $R^{11}$ is hydrogen, $R^{12}$ is 2-methylphenyl and Y is a single bond is obtained.

SCHEME II-2

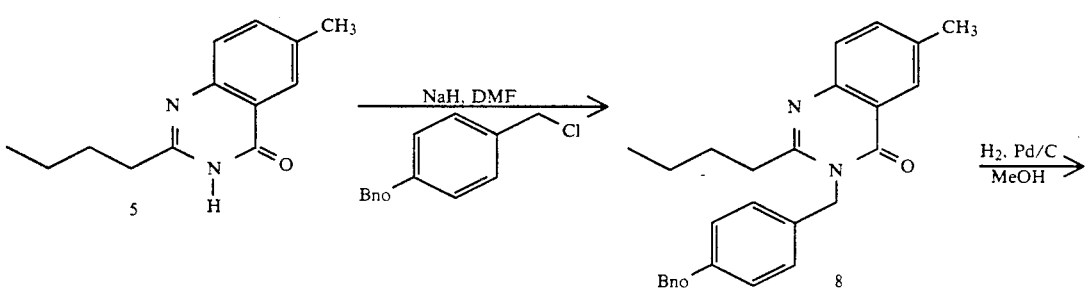

-continued
SCHEME II-2

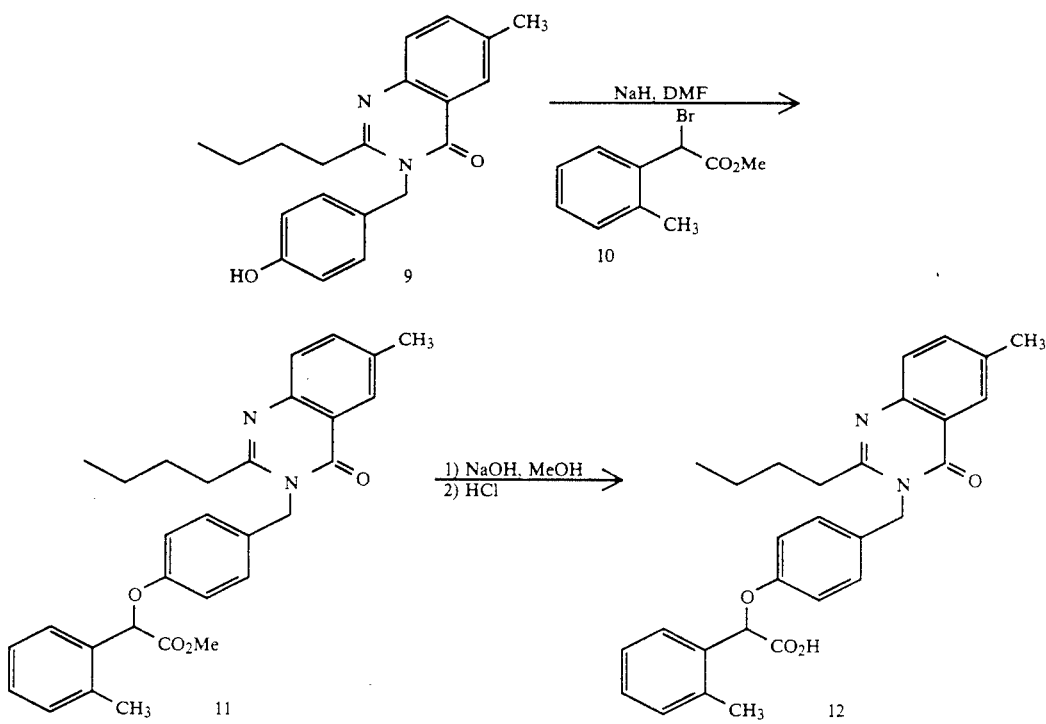

Substituted 2-bromophenylacetic esters are typically employed in the synthesis of compounds of general Formulas Ia–Ic when it is desired that $R^{11}$ be hydrogen, $R^{12}$ be a substituted phenyl group, Y is a single bond and Z is a carboxylic acid. These substituted 2-bromophenylacetic esters (14) are readily prepared from substituted phenylacetic acids (13) by a Hell-Volhard-Zelinsky reaction as shown in Scheme II-3. Alternatively, substituted 2-bromophenylacetic esters may also be obtained from benzaldehydes (15) as shown in Scheme II-4. Reaction of the substituted benzaldehydes (15) with trimethylsilyl cyanide affords the trimethylsilylcyanohydrins 16. Treatment of 16 with anhydrous hydrochloric acid in methanol or ethanol produces the hydroxy esters 17, and subsequent reaction with carbon tetrabromide and triphenylphosphine provides the substituted 2-bromophenylacetic esters 14.

SCHEME II-3

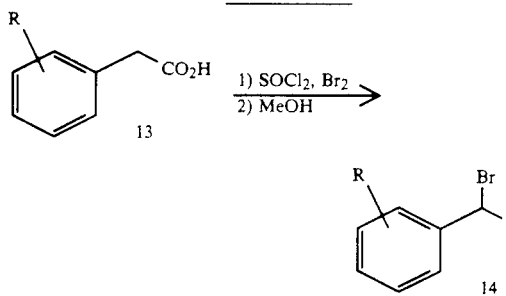

SCHEME II-4

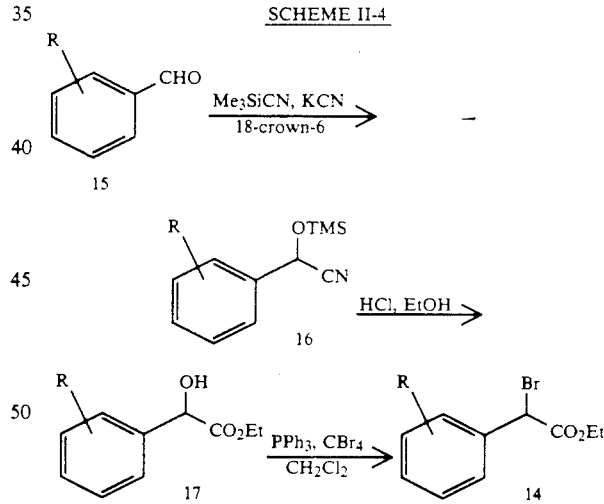

A strategy similar to that shown in Scheme II-1 is applied when a substituent other than hydrogen at $R^{11}$ is desired as shown in Scheme II-5. Intermediate phenoxyphenylacetic esters such as 3 are deprotonated with strong bases such as lithium bis(trimethylsilyl)amide in THF and can then be reacted with an alkylating agent such as an alkyl halide or mesylate. In this case, reaction of the anion derived from phenoxyester 3 with methyl iodide affords the methylated product 15. Reaction of 15 with N-bromosuccinimide gives bromide 16, which is in turn used for alkylation of a heterocyclic compound from Part I. Scheme II-5 illustrates the alkylation of heterocycle 5 with bromide 16 which after ester hydrolysis affords acid 17.

SCHEME II-5

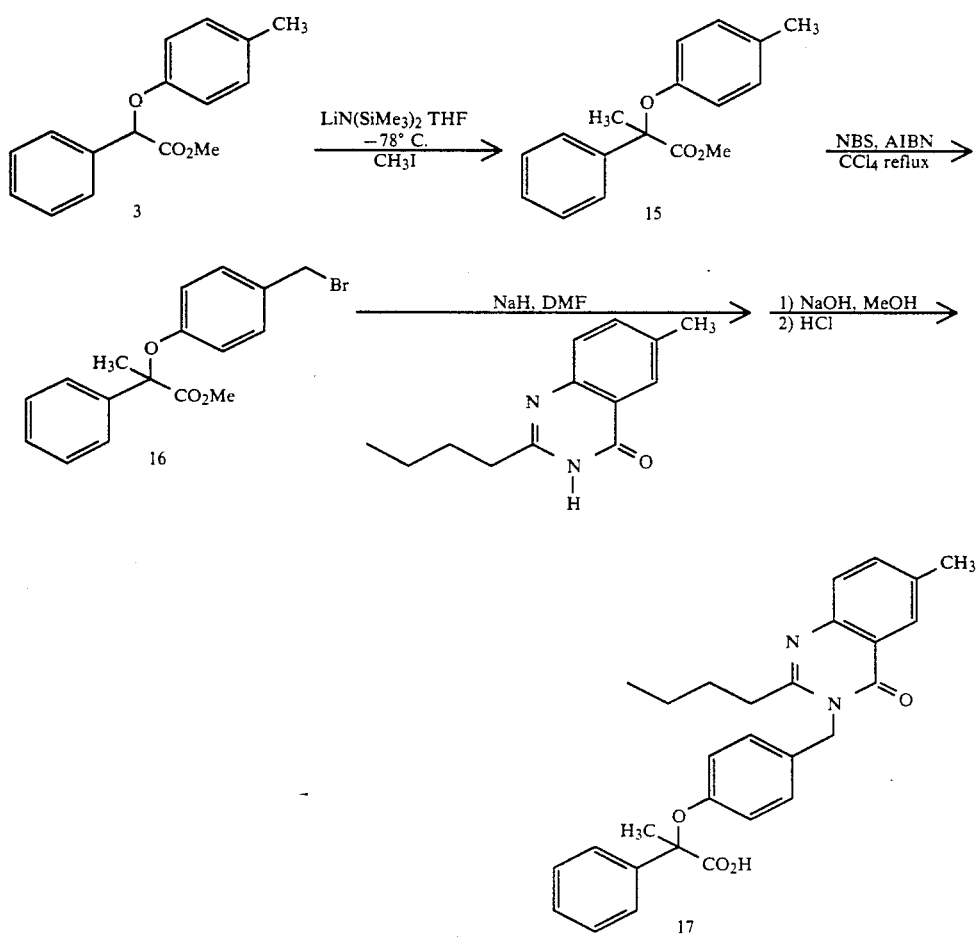

The synthesis of compound 22 of Formula Ia wherein: $K^1=-C(O)-$, $J^1$ and L are connected together to form a 6-carbon aromatic ring substituted with a methyl group at position 6, E=a single bond, $R^1$=n-butyl, $R^9$, $R^{10}$ and $R^{11}$ are H, X=O, Y=$CH_2$, Z=$CO_2H$ and $R^{12}$=phenyl is shown in Scheme II-6. In this example, p-hydroxybenzyl alcohol (18) is selectively alkylated at the phenolic hydroxyl group with methyl bromoacetate when they are refluxed with potassium carbonate in acetone. After the remaining hydroxyl group is protected as a tert-butyldimethyl- silylether, this ether (19) may then be deprotonated with a strong base such as potassium bis(trimethylsilyl)amide and reacted with an alkylating agent in a manner similar to that shown for intermediate 3 in Scheme II-5. Alkylation of ether 19 with benzyl bromide provides 20. Silylether hydrolysis of 20 and bromination of the resulting alcohol affords an alkylating agent (21) which is then used to alkylate a heterocyclic compound from Part I. Alkylation of the anion derived from heterocycle 5, followed by ester hydrolysis affords the AII Antagonist 22 shown in Scheme II-6.

SCHEME II-6

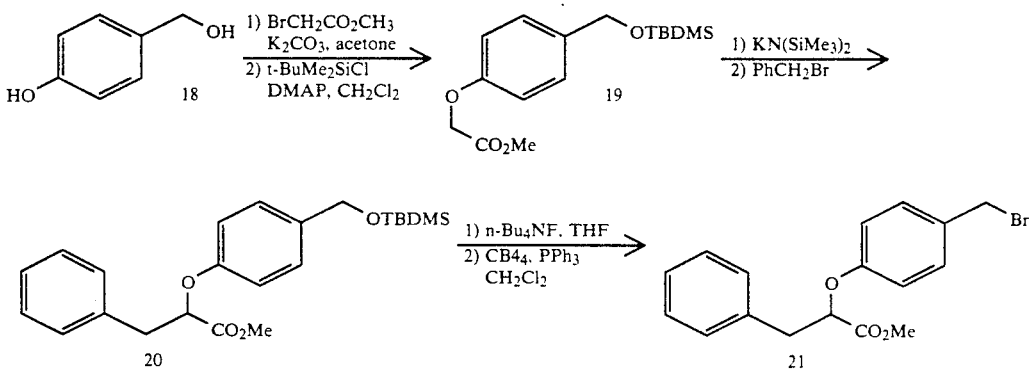

-continued
SCHEME II-6

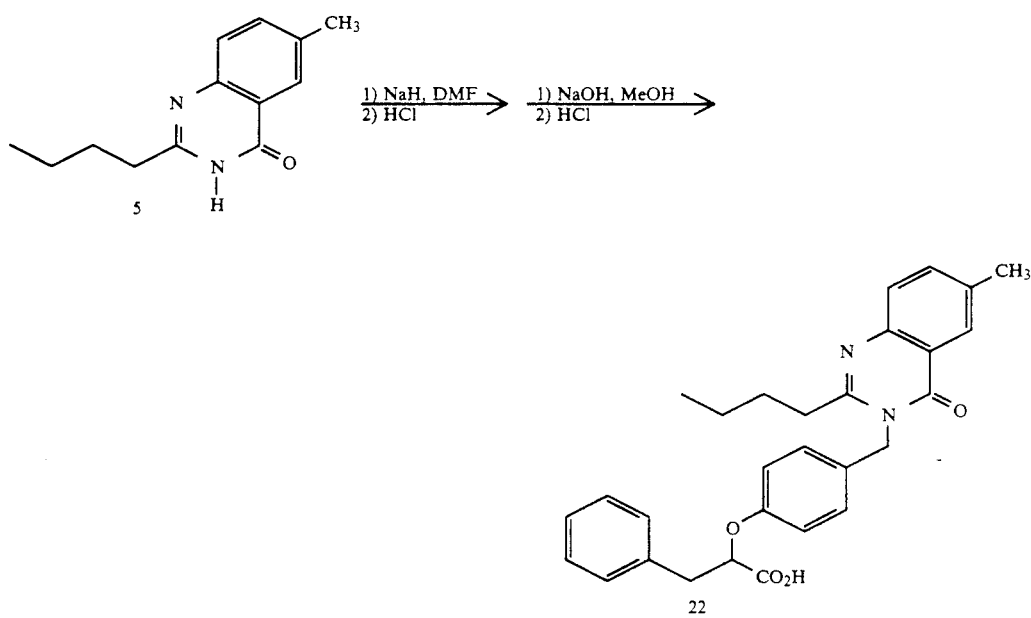

Scheme II-7 illustrates the preparation of an antagonist of Formula Ia wherein: $K^1 = -C(O)-$, $J^1$ and L are connected together to form a 6-carbon aromatic ring substituted with a methyl group at position 6, E = a single bond, $R^1$ = n-butyl, $R^9$, $R^{10}$ and $R^{11}$ are H, X is a single bond, Y = O, Z = $CO_2H$ and, $R^{12}$ = phenyl. In this example, the Hell-Volhard-Zelinsky reaction converts 4'-methyl-phenylacetic acid (23) to the alpha-bromo-ester 24, which is in turn reacted with the potassium salt of phenol to yield 25. Benzylic bromination of 25 provides alkylating agent 26 which is then reacted with a heterocyclic species described in Part I. When the sodium salt of heterocycle 5 is alkylated with the bromide 26 in DMF, followed by alkaline hydrolysis of the resulting ester, the AII Antagonist (27) of general Formula Ia is obtained.

SCHEME II-7

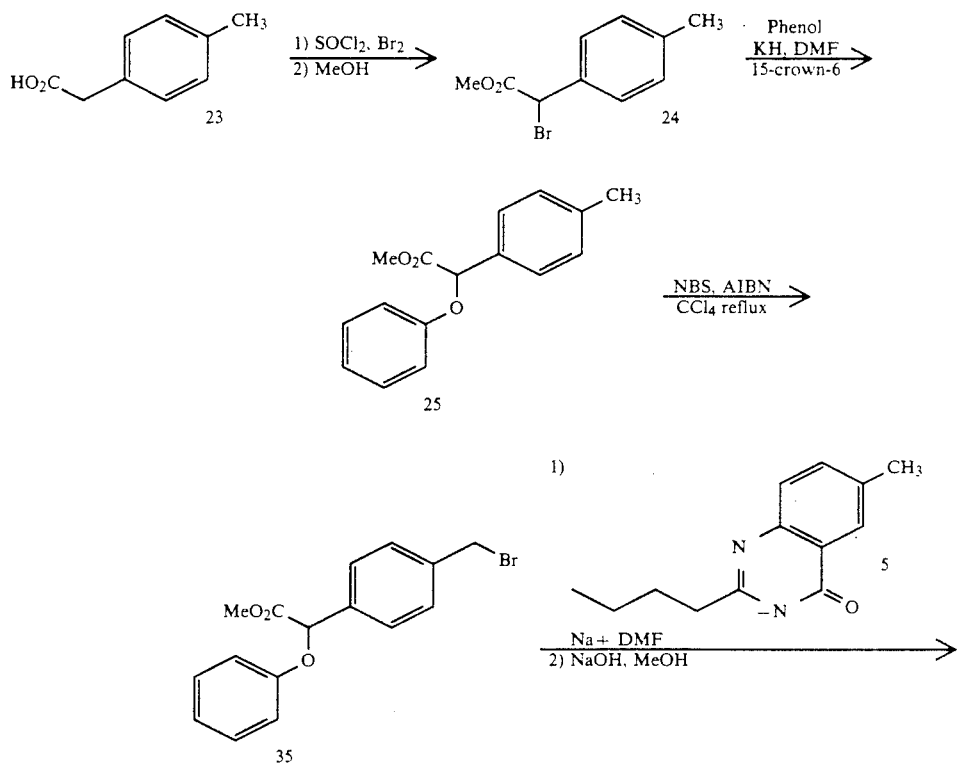

-continued
SCHEME II-7

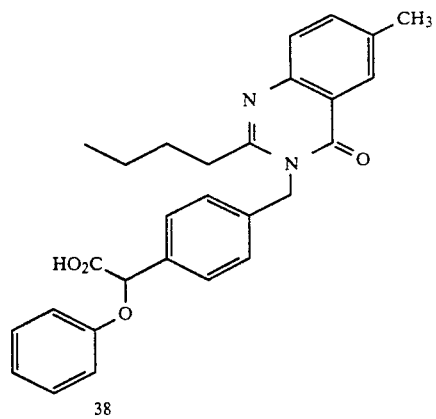

38

Scheme II-8 illustrates the preparation of analogs of Formula Ia wherein: $K^1=$—C(O)—, $J^1$ and L are connected together to form a 6-carbon aromatic ring substituted with a methyl group at position 6, E=a single bond, $R^1$=n-butyl, $R^9$ and $R^{10}$ are H, Y=a single bond, $R^{12}$ is phenyl, Z=CO$_2$H and X is either methyne or methylene. A Reformatsky reaction is first employed to prepare methyl 3-hydroxy-3-(4-methylphenyl)-2-phenylpropanoate (27) from the starting materials shown in Scheme II-8. When heated in the presence of p-toluenesulfonic acid in benzene 27 is dehydrated to the trans-stilbene derivative 28, and then benzylic bromination of 28 gives the alkylating agent 29. Deprotonation of a heterocycle such as 5 with sodium hydride in DMF and treatment with 29 gives adduct like 30. Alkaline hydrolysis of 30 affords a product 31, in which X is a methyne group ($R^{11}$ is absent) doubly bonded to the carbon atom bearing substituents $R^{12}$ and Z as shown in Scheme II-8. Catalytic hydrogenation of 31 gives the derivative 32 where X is a methylene group and $R^{11}$ is a hydrogen atom.

SCHEME II-8

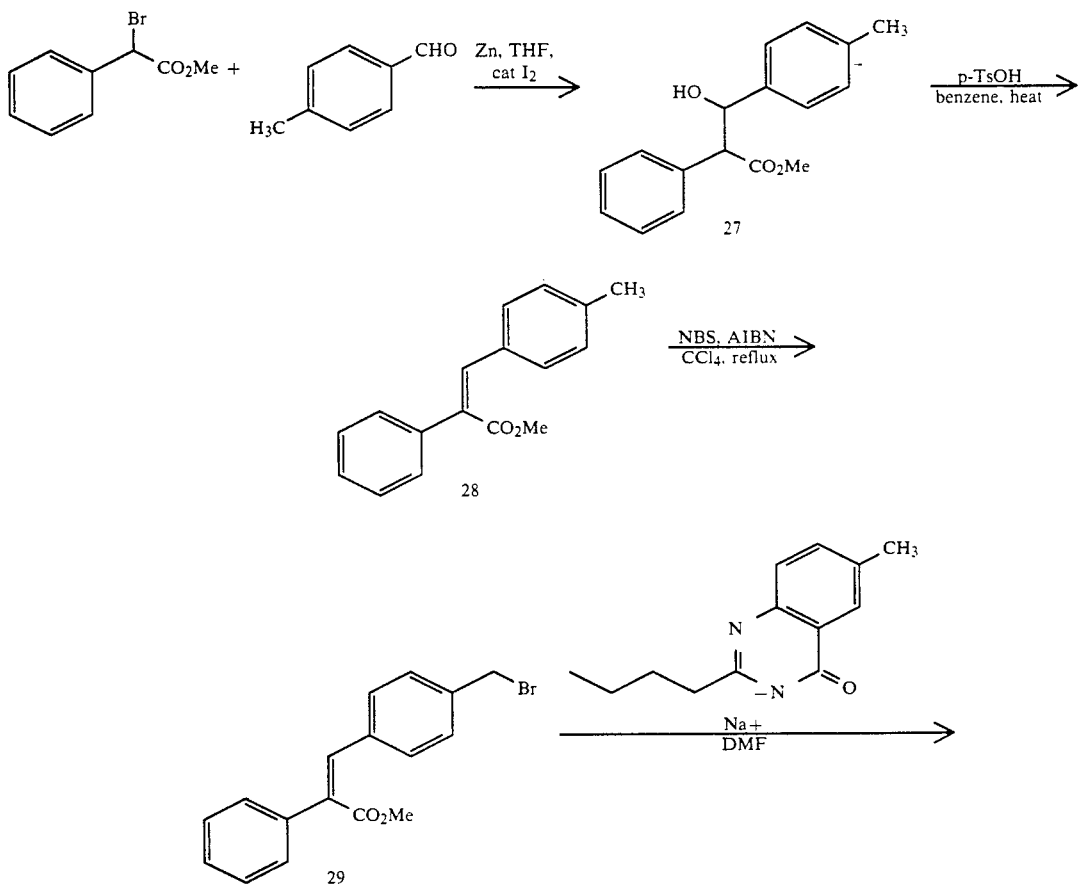

-continued
SCHEME II-8

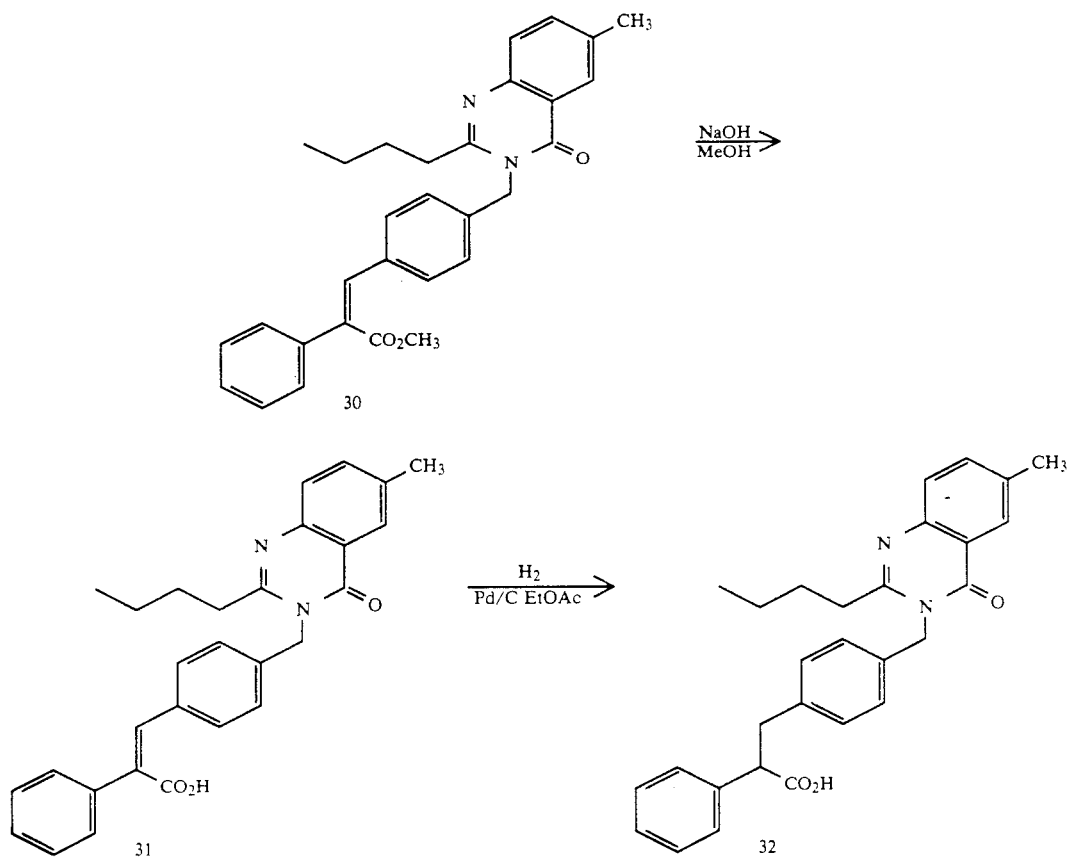

Scheme II-9 illustrates the preparation of an analog (38) wherein: $K^1$=—C(O)—, $J^1$ and L are connected together to form a 6-carbon aromatic ring substituted with a methyl group at position 6, E is a single bond, $R^1$ is n-butyl, $R^9$, $R^{10}$ and $R^{11}$ are hydrogen, $R^{12}$ is 2-chlorophenyl and Z is a tetrazole group. In this synthesis, the ester group of intermediate 33 is converted to a nitrile prior to alkylating a heterocycle (Part I) with this substituted benzyl element. Thus, reaction of ester 33 with ammonia in methanol, followed by dehydration of amide 34 produces nitrile 35. Benzylic bromination affords 36, which then may be reacted with the sodium salt of a heterocycle such as 5 in DMF to give an intermediate like 37. Finally, reaction of a nitrile like 37 with trimethylstannyl azide in refluxing toluene gives tetrazoles related to 38 as shown in Scheme II-9.

SCHEME II-9

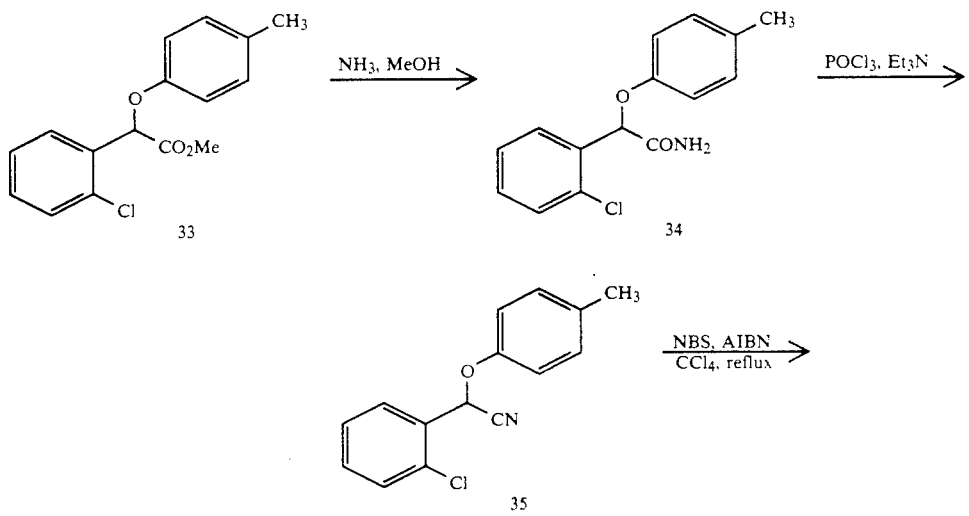

-continued
SCHEME II-9

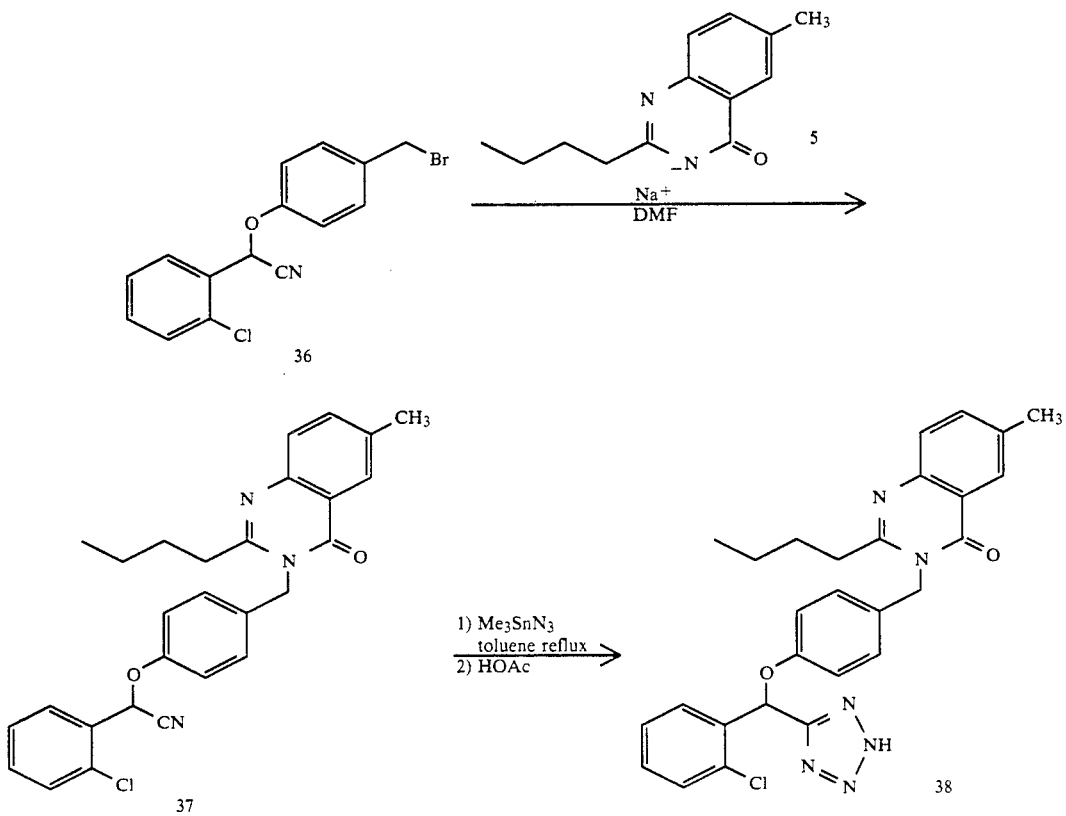

The preparation of a derivative of Formula I analogous to tetrazole 38 (Scheme II-9) in which X is a methylene group, Y is a single bond and $R^{12}$ is phenyl, is shown in Scheme II-11. In this synthesis, phenylacetonitrile is deprotonated with lithium bis(trimethylsilyl)amide and then alkylated with the tert-butyldimethylsilylether of p-hydroxymethylbenzyl bromide (preparation of bromide 39 is shown in Scheme II-10) to yield nitrile 40. The silylether group in compound 40 is directly converted to the bromide 41 with carbon tetrabromide, triphenylphosphine and acetone in dichloromethane (Mattes, H.; Benezra, C. Tetrahedron Lett., 1987, 1697). Alkylation of the sodium salt of heterocycle 5 with bromide 41, followed by reaction of 42 with trimethylstannyl azide in refluxing toluene yields the tetrazole 43.

SCHEME II-10

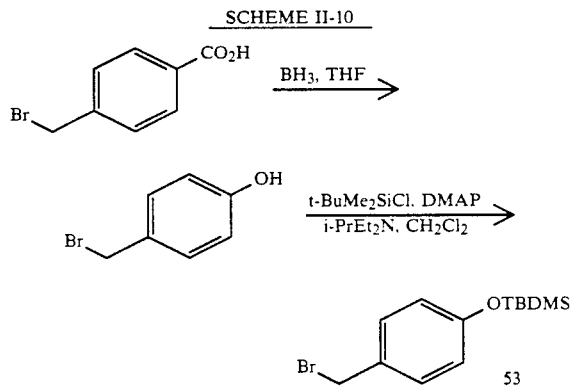

SCHEME II-11

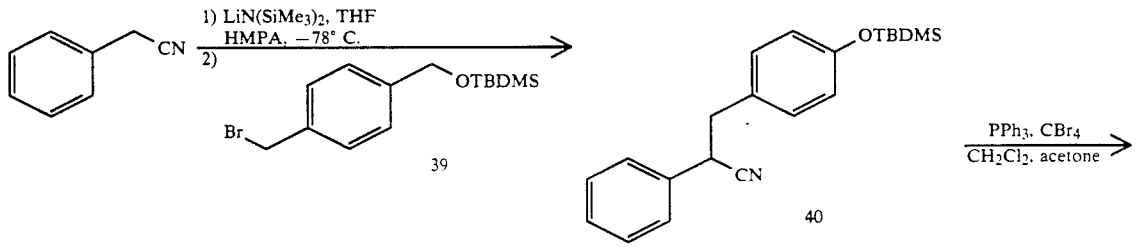

-continued
SCHEME II-11

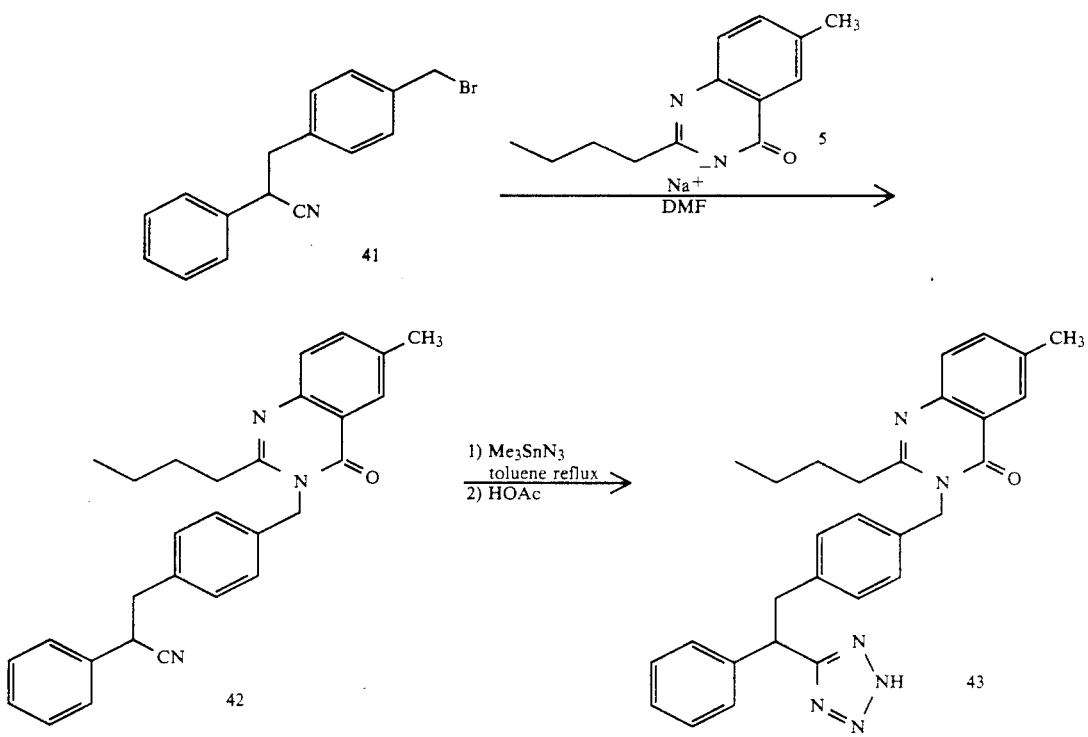

Scheme II-12 illustrates the preparation of a derivative of Formula Ia wherein: K$^1$=—C(O)—, J$^1$ and L are connected together to form a 6-carbon aromatic ring substituted with a methyl group at position 6, R$^1$ is n-butyl, E is a single bond, R$^9$, R$^{10}$ and R$^{11}$ are H, X=O, Y=a single bond, R$^{12}$ is 2-methylphenyl, and Z is a phosphonic acid group. Reaction of o-tolualdehyde with dimethylphosphite in the presence of triethylamine affords the phosphonate ester 44. Bromination of the hydroxyl group of 44 with carbon tetrabromide and triphenylphosphine in dichloromethane gives bromide 45. Deprotonation of p-hydroxybenzyl alcohol with sodium hydride in DMF followed by addition of bromide 45 affords intermediate 46. A second bromination reaction (CBr$_4$, PPh$_3$, CH$_2$Cl$_2$) converts alcohol 46 to the bromide 47 which is then used to alkylate a heterocyclic compound described in Part I. Scheme II-12 illustrates the case where the anion of heterocycle 5 is reacted with bromide 47 to give upon workup, the phosphonate mono-ester 48. Phosphonic acid 49 may be obtained by treatment of the mono-methyl ester 48 with trimethylsilyl bromide.

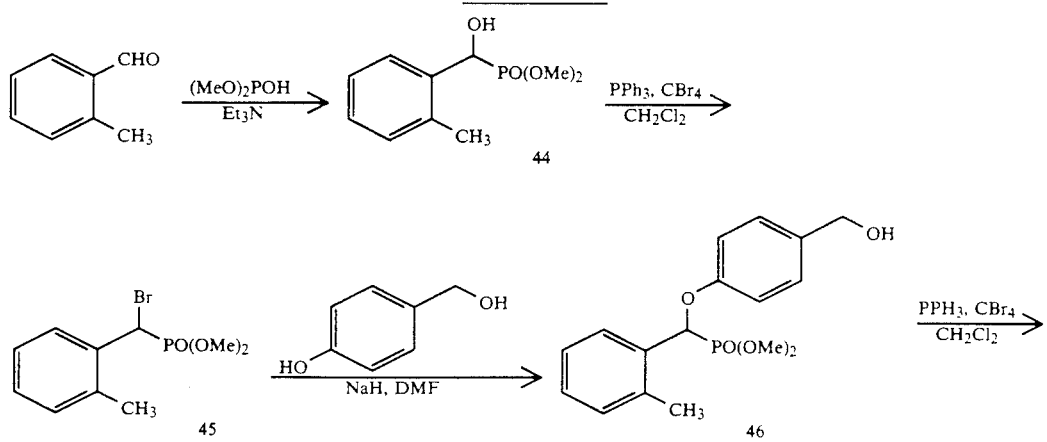

-continued
SCHEME 11-12

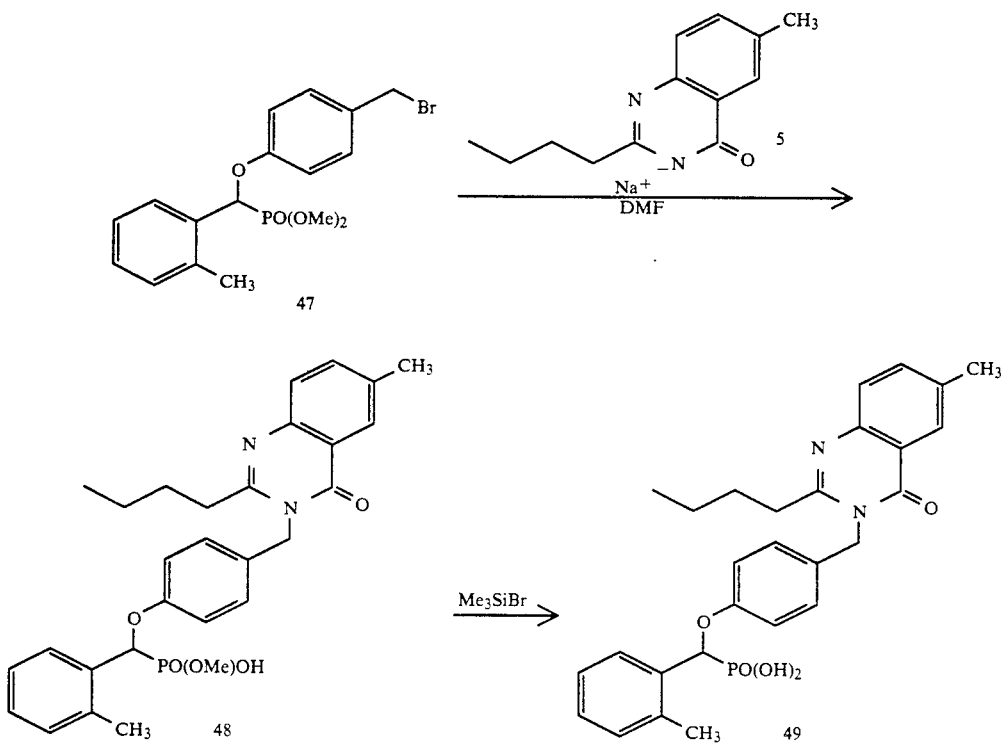

The synthesis of a derivative of Formula Ia where Z is an acyl-sulfonamide group is illustrated in Scheme II-13. Reaction of a carboxylic acid of general Formula Ia such as 7 (Scheme II-1) with 1,1'-carbonyldiimidazole in THF at elevated temperatures gives an acylimidazolide which may be reacted with a sulfonamide (benzenesulfonamide in this example) and DBU in THF to provide the target compound (50) where Z is the acyl-sulfonamide group.

SCHEME 11-13

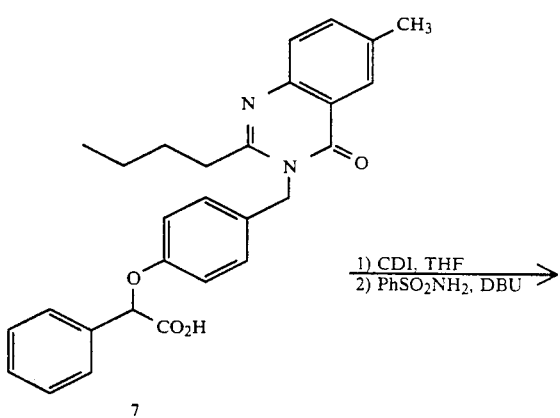

-continued
SCHEME 11-13

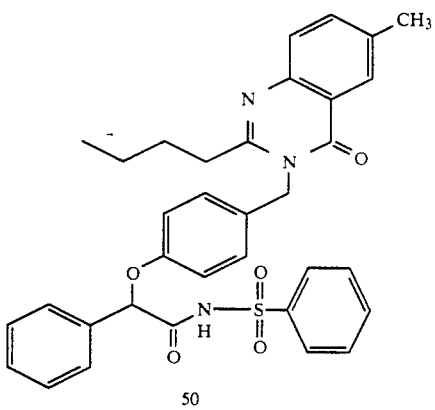

Precursors for the synthesis of AII Antagonists incorporating a substituted benzyl element wherein either substituents $R^9$ or $R^{10}$ are non-hydrogen may include substituted p-cresols, 4-hydroxybenzyl alcohols, 4-hydroxybenzaldehydes, 4-hydroxybenzoic acids and their esters as shown in Schemes II-14–16.

Commercially available benzyl alcohols such as 3-chloro-4-hydroxy-5-methoxybenzyl alcohol (51) may be selectively alkylated by alpha-bromophenylacetic esters when they are refluxed together in the presence of bases such as anhydrous potassium carbonate, giving 2-phenoxyesters like 52 shown in Scheme II-14. Conversion of the benzyl alcohol group in 52 to a bromide ($CBr_4$, $PPh_3$, $CH_2Cl_2$) affords alkylating agent 53. A heterocyclic compound from Part I is then alkylated with bromide 53, and the product is hydrolyzed to giving a derivative of general Formulas Ia–Ic as described previously.

SCHEME II-14

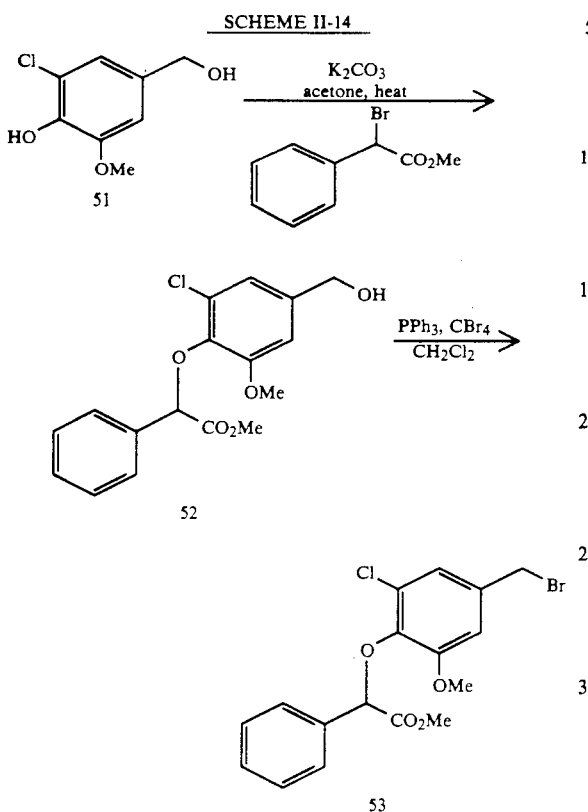

Scheme II-15 illustrates the use of commercially available 3-ethoxy-4-hydroxybenzaldehyde (54) to prepare an AII Antagonist of Formula Ia bearing a 3-ethoxy group ($R^9$) on the substituted benzyl element. Alkylation of the phenolic group of 54 with methyl 2-bromophenylacetate gives the aldehyde 55 which is then reduced to a benzyl alcohol with sodium borohydride in methanol or ethanol. The alcohol is converted to the bromide 56, which may be used to alkylate a heterocyclic compound defined in Part I to afford an AII Antagonist of general Formula Ia–Ic.

SCHEME II-15

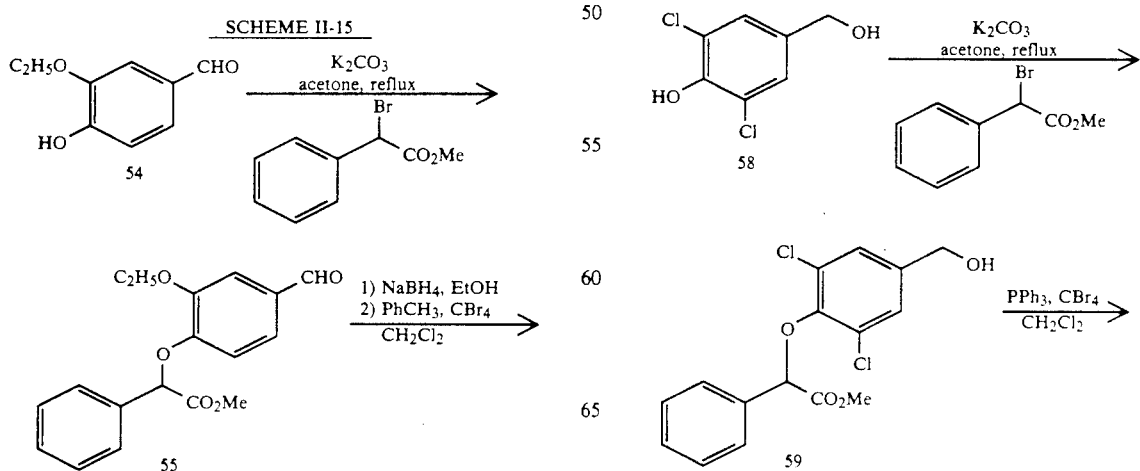

-continued
SCHEME II-15

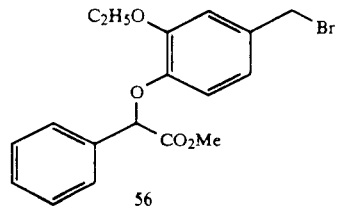

Substituted 4-hydroxybenzoic esters are also convenient precursors for the synthesis of the substituted benzyl element defined in AII Antagonists of Formulas Ia–Ic. In this approach, the phenolic hydroxyl group is usually first protected with a suitable protecting group, the ester is then reduced to a hydroxymethyl group, and deprotection affords a 4-hydroxybenzyl alcohol derivative. Scheme II-16 illustrates the preparation of an alkylating agent (60) where $R^9$ and $R^{10}$ are 3,5-dichloro substituents using this sequence starting from methyl 3,5-dichloro-4-hydroxybenzoate (57). Silylation of phenol 57 followed in turn by lithium aluminum hydride reduction of the ester and silylether deprotection affords 3,5-dichloro-4-hydroxybenzyl alcohol (58). Phenol 58 may then be selectively alkylated with methyl 2-bromophenylacetate. Reaction of the alcohol 59 with carbon tetrabromide and triphenylphosphine then produces the bromide 60 which may be used to alkylate a heterocyclic compound described in Part I.

SCHEME II-16

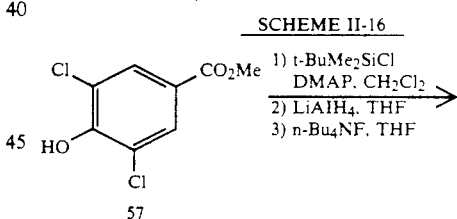

-continued
SCHEME II-16

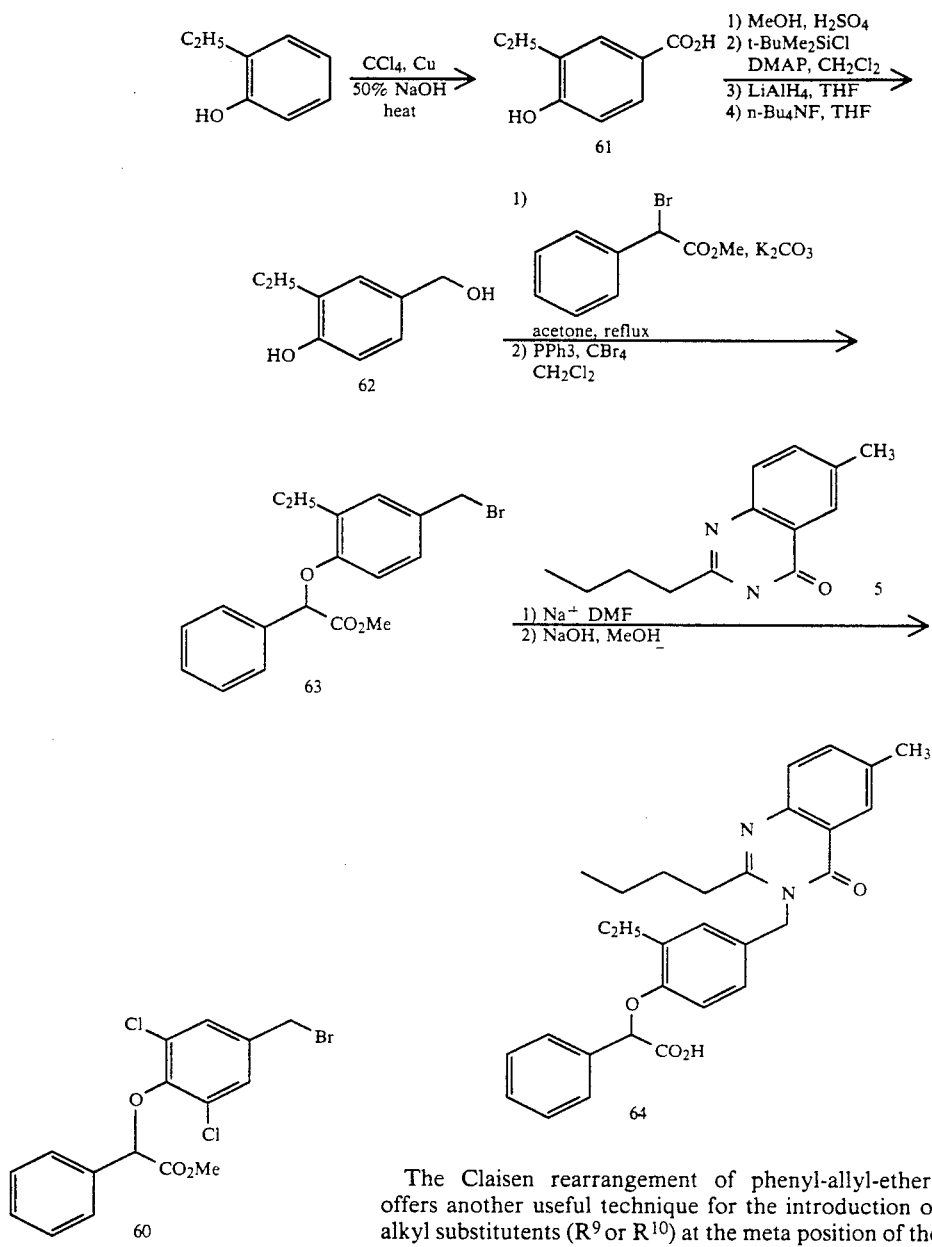

A variety of 2-substituted phenols are selectively carboxylated when refluxed with carbon tetrachloride, 50% aqueous sodium hydroxide and powdered copper (European Patent Application #193,853, 10-Sept-86) to afford the corresponding substituted 4-hydroxybenzoic acids. This reaction may be added to the synthetic sequence when it is convenient to derive the desired substituent on the benzyl portion of the target AII Antagonist from a readily available 2-substituted phenol. This strategy is illustrated for the preparation of derivative 64 shown in Scheme II-17. Carboxylation of 2-ethylphenol provides 3-ethyl-4-hydroxybenzoic acid (61). Acid 61 is then esterified, silylated, reduced and desilylated to give the 3-ethyl-4-hydroxybenzyl alcohol 62. Alcohol 62 may then be used to complete the synthesis of AII Antagonist 64 shown in Scheme II-21 using the previously discussed methodology.

The Claisen rearrangement of phenyl-allyl-ethers offers another useful technique for the introduction of alkyl substitutents ($R^9$ or $R^{10}$) at the meta position of the substituted benzyl element. In Scheme II-18, 4-hydroxybenzyl alcohol is selectively allylated and then silylated to afford mixed ether 65. Claisen rearrangement at 185° C. of ether 65 provides the allylphenyl 66 which is then alkylated with methyl 2-bromophenylacetate. The silylether 67 is then converted to the bromide 68. Alkylation of the heterocycle 5 with bromide 68, followed by alkaline hydrolysis affords the AII Antagonist 69 shown in Scheme II-18 and described in Example 2 of the experimental section.

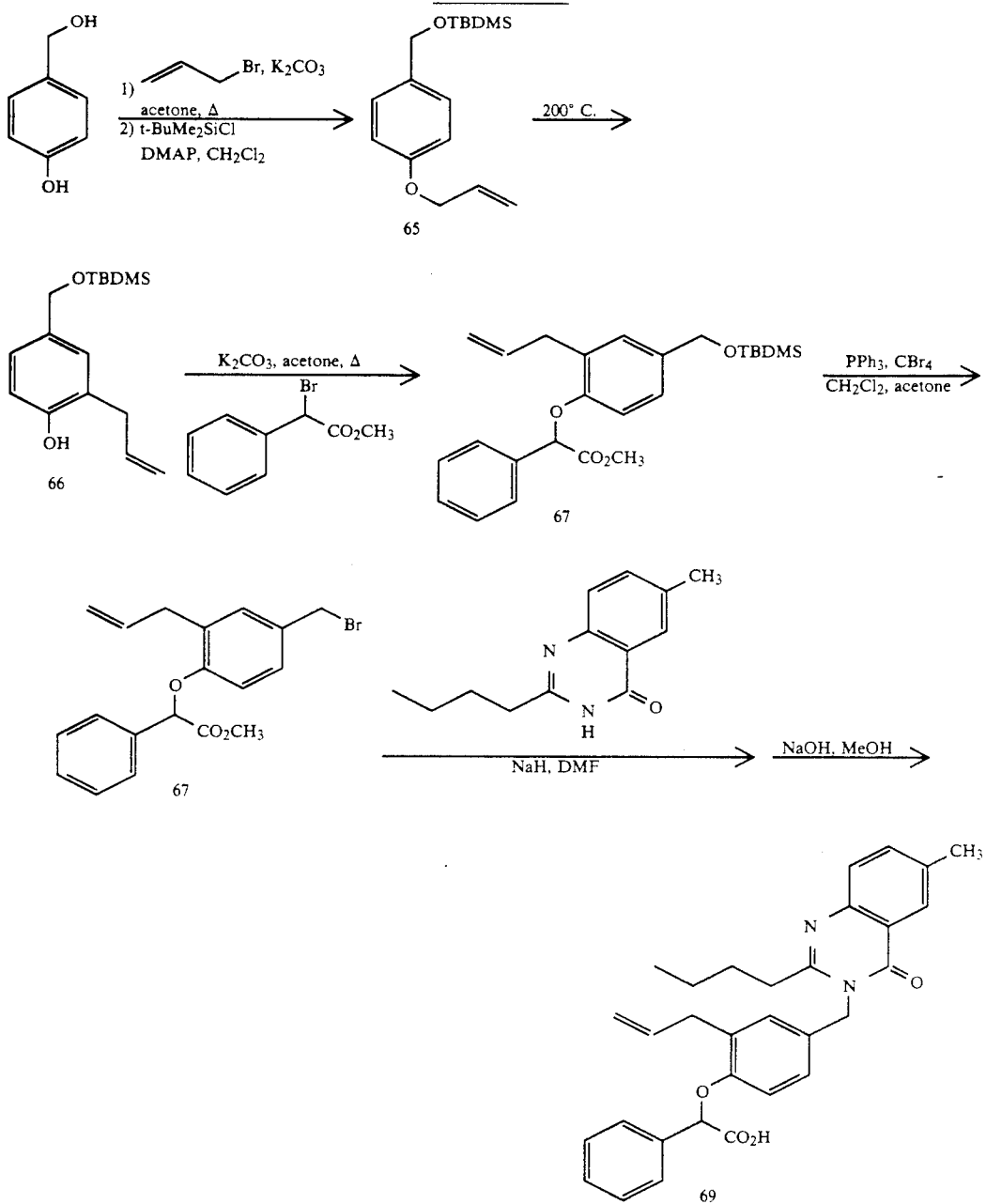

SCHEME II-18

A variation of the Claisen rearrangement strategy for the introduction of the $R^9$ or $R^{10}$ substituents was employed for the preparation of AII Antagonist 75 as shown in Scheme II-19. In this synthesis, the Claisen rearrangement of the allyl ether derived from methyl 4-hydroxybenzoate (70) afforded phenol 71. Phenol 71 was silylated, the intermediate ester was reduced with lithium aluminum hydride, and then desilylated to produce 3-allyl-4-hydroxybenzyl alcohol (72). Hydrogenation of 72, followed by alkylation of 73 with methyl 2-bromophenylacetate and then bromination gave the alkylating agent 74. Alkylation of the quinazolinone 75 with bromide 74, followed by alkaline hydrolysis of the resulting ester (76) afforded the AII Antagonist 77 shown in Scheme II-19 and described in Example 6 in the experimental section.

SCHEME II-19

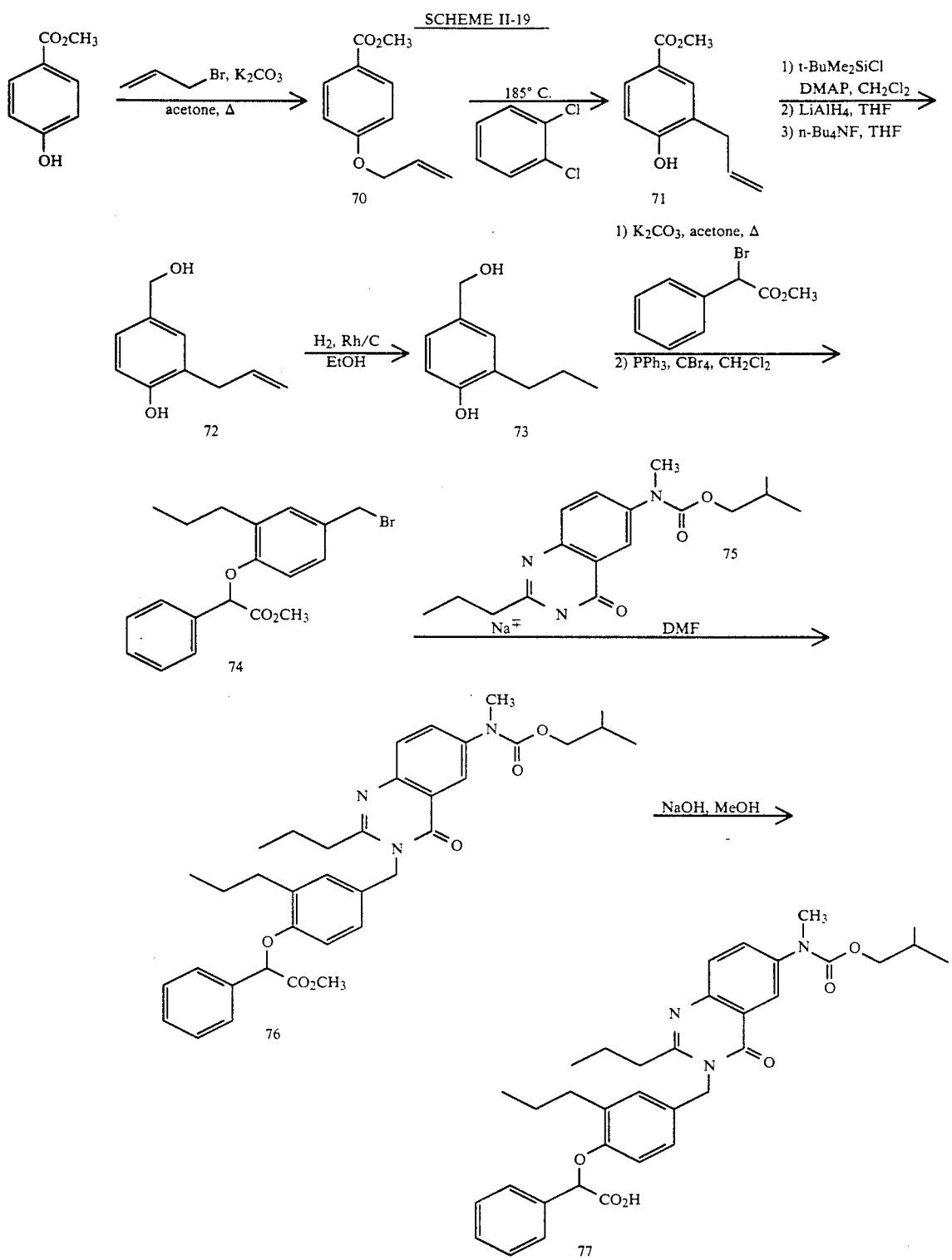

The Claisen rearrangement strategy for the introduction of a meta-alkyl substituent onto the substituted benzyl element of an AII Antagonist of Formulas Ia-Ic may be exercised twice when it is desired that both $R^9$ and $R^{10}$ be meta-alkyl substituents. Thus, allyl phenol 71 may be converted to its O-allylether and subjected to a second Claisen rearrangement to provide the phenol (78) shown in Scheme II-20. Silylation of phenol 78, followed by catalytic hydrogenation, reduction of the ester group with lithium aluminum hydride and bromination ($CBr_4$, $PPh_3$, $CH_2Cl_2$) gives the benzyl bromide 79. Alkylation of heterocycle 5 with the bromide 79, followed by silylether deprotection provides an intermediate phenol 80. The phenolic hydroxyl group of 80 may then be alkylated with an alpha-bromoester and the ester hydrolyzed to yield the acid 81 in which $R^9$ and $R^{10}$ are meta-propyl groups as shown in Scheme II-20.

SCHEME II-20

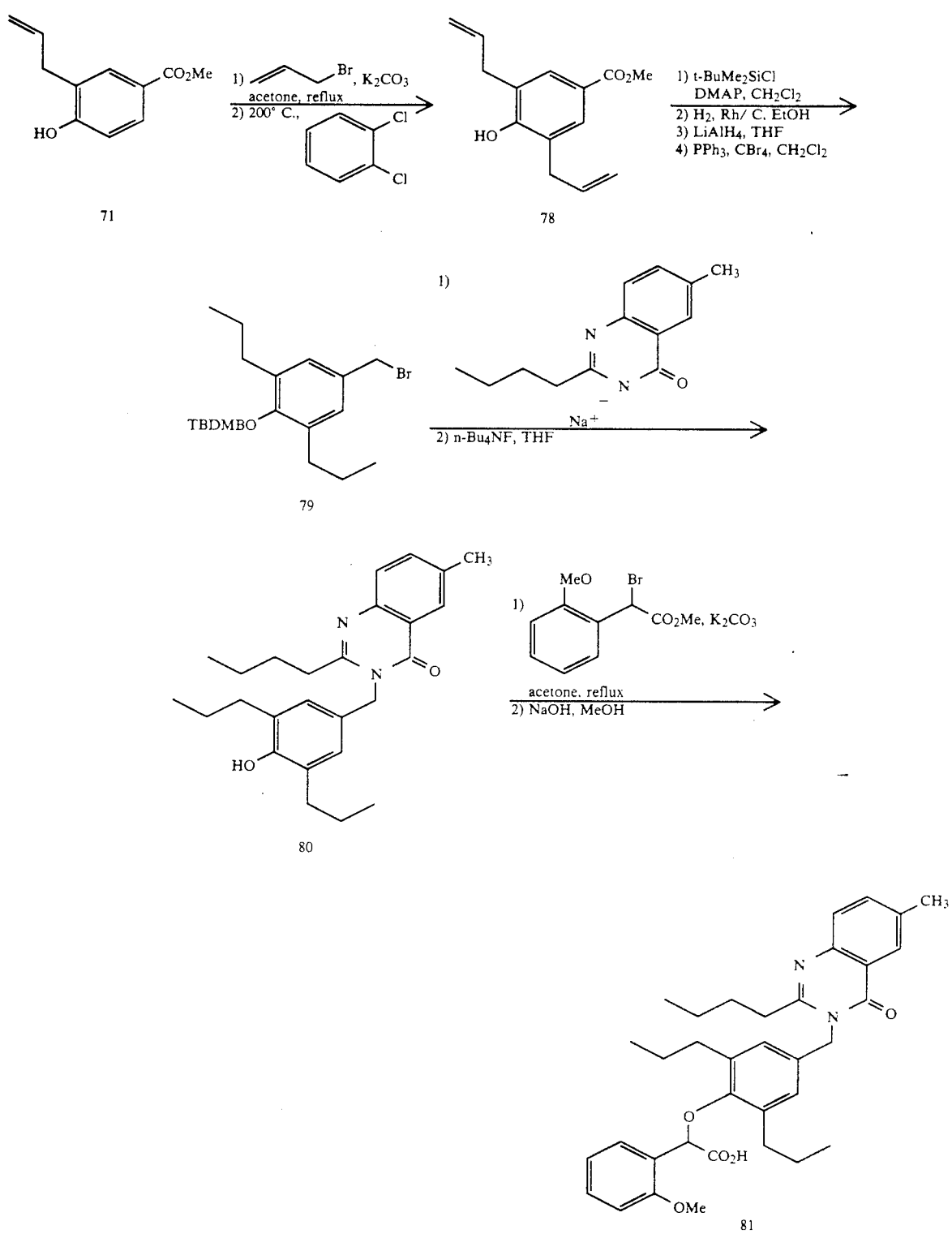

The synthesis of compounds of Formula Ia wherein: K$^1$=—C(O)—, J$^1$ and L are connected together to form a 6-carbon aromatic ring substituted with a methyl group at position 6, E=a single bond, R$^1$=n-butyl, R$^9$, R$^{10}$ and R$^{11}$ are H, Y=a single bond, Z=CO$_2$H R$^{12}$=phenyl, and X=NR, are presented in Schemes II-21 and II-22. To access these analogs, a heterocycle (i.e. 5) defined in Part I is alkylated with p-nitrobenzyl bromide to yield nitro compounds such as 82 in Scheme II-21. Catalytic hydrogenation of the nitro group provides an aniline derivative (83) which is then alkylated by an alpha-bromoester. The resulting ester is subsequently hydrolyzed to afford a derivative of Formulas Ia-Ic (84) where X=NH.

SCHEME II-21

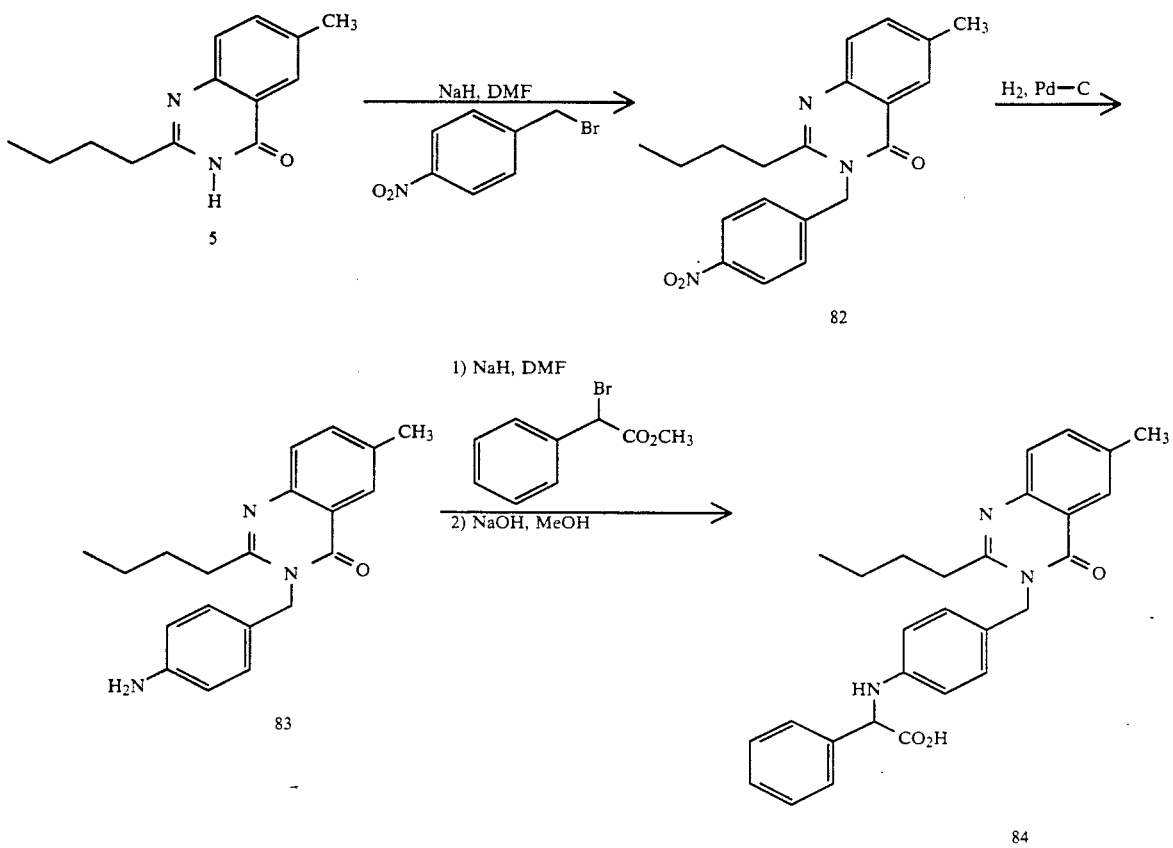

The preparation of AII Antagonists of Formulas Ia-Ic similar to 84 in Scheme II-21 but having X=NR may be accomplished by methodology shown in Scheme II-22. The substituted aniline (83) presented above, may be readily converted to the N-tert-butylcarbamate (BOC) 85. Carbamates such as 85 may be deprotonated at the amide nitrogen atom when reacted with bases such as sodium hydride in DMF, and then reacted with an alkyl halide (e.g. allyl bromide). Subsequent treatment of the intermediate with trifluoroacetic acid removes the BOC group providing the monoalkylated aniline derivative 86. The aniline nitrogen in 86 may be deprotonated again with sodium hydride in DMF and alkylated a second time with a substituted alpha-bromoester and then hydrolyzed to afford the targeted AII Antagonists (87) of Formulas Ia-Ic where X=NR.

SCHEME II-22

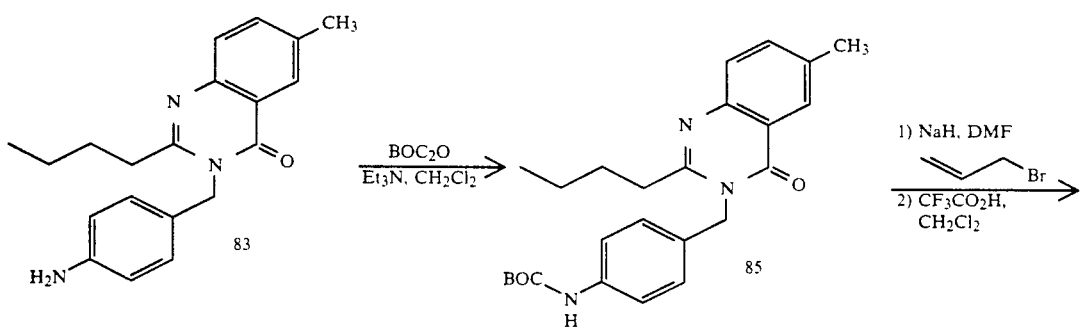

-continued
SCHEME II-22

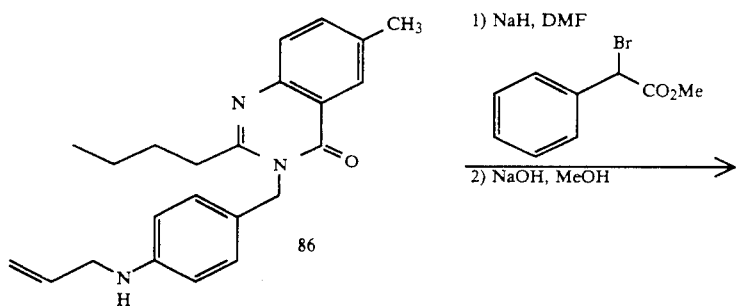

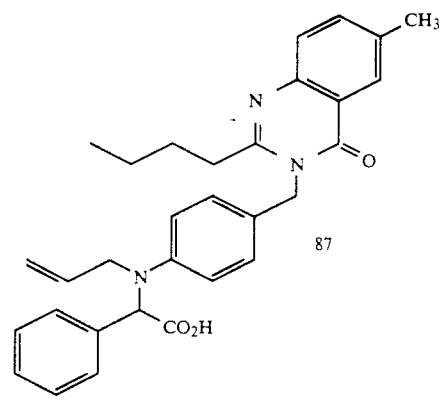

Schemes II-23 and II-24 illustrate routes for the synthesis of AII Antagonists of general Formulas Ia–Ic for cases in which it is desirable to introduce the benzyl element at the beginning of or during the preparation of the heterocyclic moiety. Scheme II-23 is basically an adaptation of Scheme I-38 (also see Scheme I-37), whereby the $N^4$-substituent is present at the time the triazolinone ring is formed, while the $N^2$-substituent is introduced subsequently by alkylation. The ester carbethoxyhydrazone intermediate (88) is prepared as in Scheme I-38. An alkylating agent such as 4 (Scheme II-1) is reacted with an alkali metal azide such as lithium azide in dimethylsulfoxide or dimethylformamide, generally at ambient temperature, to give the azide derivative 89. This is reduced to the amine 90, for example by treatment of 89 with triphenylphosphine in tetrahydrofuran at ambient temperature, followed by addition of water. Heating the ester carbethoxyhydrazone 88 with the amine at about 50°–80° C. yields the $N^4$-substituted triazolinone 91. Treatment of 91 with a base such as sodium hydride in a solvent such as anhydrous dimethylformamide and further treatment with an alkylating agent (e.g., an alkyl bromide, iodide, methanesulfonate, or p-toluenesulfonate, a benzyl bromide or chloride) yields the $N^2$-alkylated product 92. Saponification of the ester (e.g., by sodium hydroxide in aqueous methanol) provides the final product 93.

SCHEME II-23

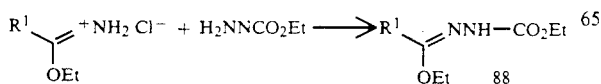

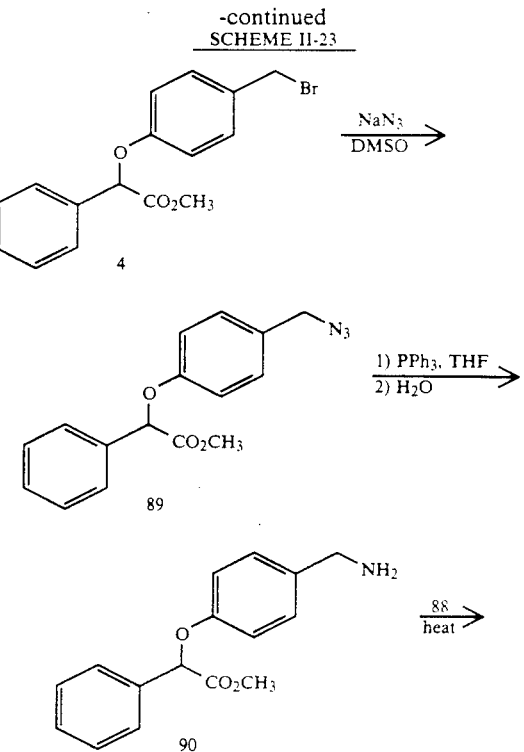

SCHEME II-23 -continued

SCHEME II-24 -continued

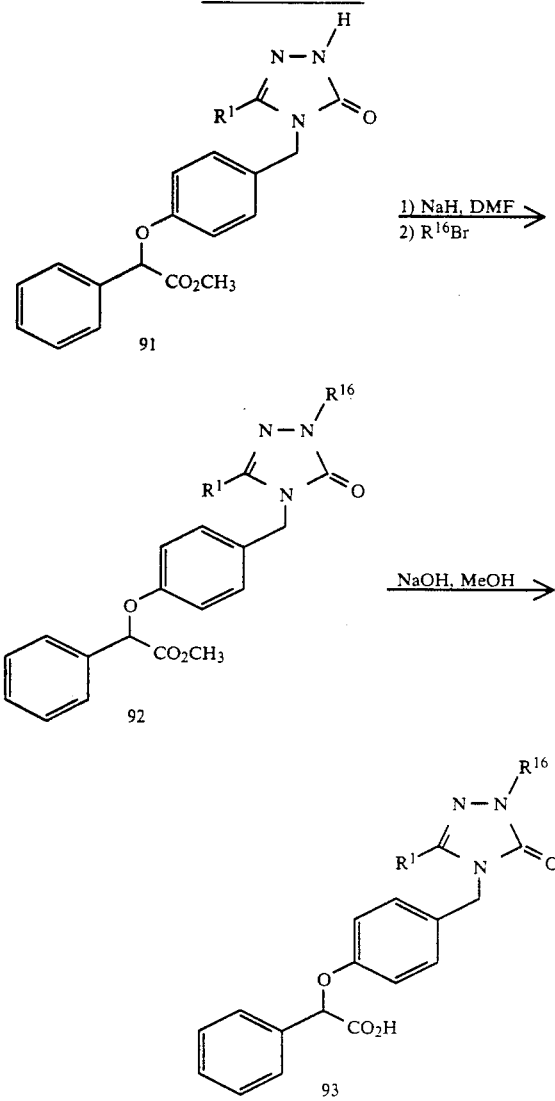

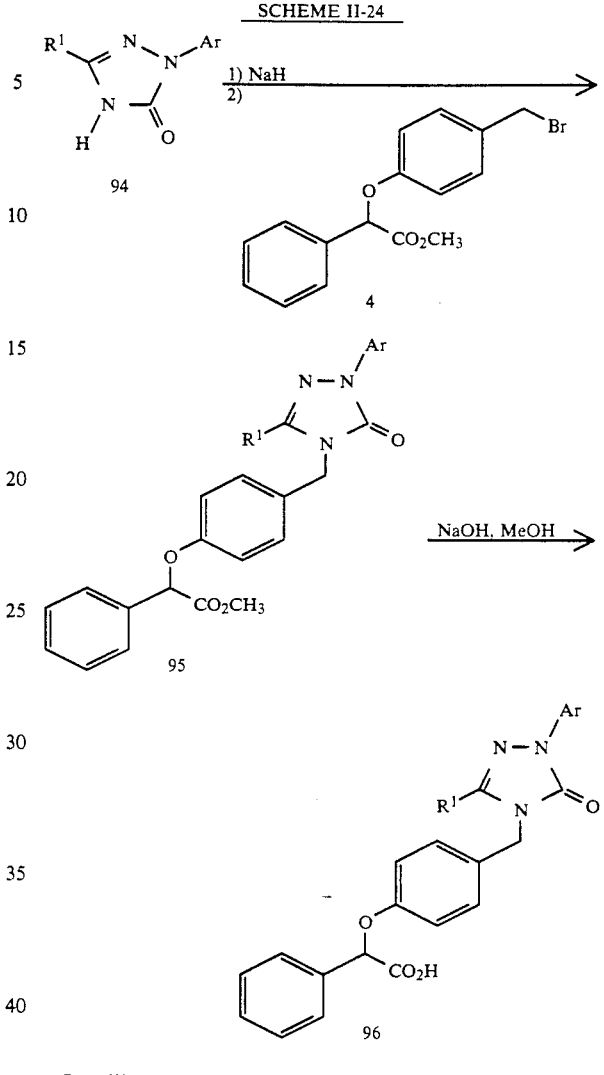

This scheme represents an adaptation of Scheme I-39, which is valuable for the preparation of triazolinones substituted with an aryl or heteroaryl substituent at $N^2$. Thus, the aryltriazolinone intermediate 94 (see Reaction Scheme I-39 and accompanying discussion) is treated with a base, such as sodium hydride in a solvent like N,N-dimethylformamide (DMF) to form the anion. Further treatment with a bromide such as 4 (Scheme II-1) yields the $N^4$-alkylated trizolinone 95. Saponification of the ester (e.g., by sodium hydroxide in aqueous methanol) followed by acidification affords the final product 96.

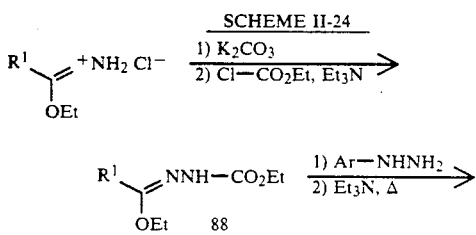

SCHEME II-24

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methanesulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

It will be further appreciated that the compounds of general Formula I in this invention may be derivatised at functional groups to provide prodrug derivatives which are capable of conversion back to the parent compounds in vivo. The concept of prodrug administration has been extensively reviewed (e.g. A. A. Sinkula in *Annual Reports in Medicinal Chemistry*, Vol 10, R. V. Heinzelman, Ed., Academic Press, New York London, 1975, Ch. 31, pp. 306–326), H. Ferres, *Drugs of Today*, Vol. 19, 499–538 (1983) and *J. Med. Chem.*, 18, 172 (1975). Examples of such prodrugs include the physiologically acceptable and metabolically labile ester derivatives, such as lower alkyl (e.g. methul or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminoethyl esters (e.g. 2-dimethylaminoethyl esters). Additionally, any physiologically acceptable equivalents of the compounds of general Formula I, similar to the metabolically labile esters, which are capable of producing the parent compounds of general Formula I in vivo, are within the scope of this invention.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor binding assay using rabbit aortae membrane preparation:

Three frozen rabbit aortae (obtained from Pel-Freeze Biologicals) were suspended in 5 mM Tris-0.25M sucrose, pH 7.4 buffer (50 ml) homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitration and the suspension was used for 100 assay tubes. Samples tested for screening were done in duplicate. To the membrane preparation (0.25 ml) there was added $^{125}$I-Sar$^1$Ile$^8$-angiotensin II [obtained from New England Nuclear] (10 ml; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^{125}$I-Sar$^1$Ile$^8$-angiotensin II was presented as a measure of the efficacy of such compounds as AII antagonists.

Receptor assay using Boyine adrenal cortex preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF) (0.1 mM)]. (For screening of compounds, generally duplicates of tubes are used). To the membrane preparation (0.5 ml) there was added 3H-angiotensin II (50 mM) (10 ml) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^3$H-angiotensin II was presented as a measure of the efficacy of such compounds as AII antagonists.

Using the methodology described above, representative compounds of the invention were evaluated and were found to exhibit an activity of at least $IC_{50}<50$ mM thereby demonstrating and confirming the utility of the compounds of the invention as effective AII antagonists.

The potential antihypertensive effects of the compounds described in the present invention may be evaluated using the methodology described below:

Male Charles River Sprague-Dawley rats (300–375 gm) were anesthetized with methohexital (Brevital; 50 mg/kg i.p.). The trachea was cannulated with PE 205 tubing. A stainless steel pitching rod (1.5 mm thick, 150 mm long) was inserted into the orbit of the right eye and down the spinal column. The rats were immediately placed on a Harvard Rodent Ventilator (rate—60 strokes per minute, volumn—1.1 cc per 100 grams body weight). The right carotid artery was ligated, both left and right vagal nerves were cut, the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered and 15 minutes later propranolol (1 mg/kg i.v.). Thirty minutes later antagonists of formula I were administered intravenously or orally. Angiotensin II was then typically given at 5, 10, 15, 30, 45 and 60 minute intervals and every half-hour thereafter for as long as the test compound showed activity. The change in the mean arterial blood pressure was recorded for each angiotensin II challenge and the percent inhibition of the angiotensin II response was calculated.

Thus, the compounds of the invention are useful in treating hypertension. They are also of value in the management of acute and chronic congestive heart failure. These compounds may slso be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, reanl vascular hypertension, left ventricular dysfunction, diabetic retinapathy and in the management of vascular disorders such as migraine, Raynaud's disease, luminal hyperclasia, and to minimize the atherosclerotic process. The application of the compounds of this invention for these and similar disorders will be apparent to those skilled in the art The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Perferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like. Pharmaceutical formulations prepared to treat intraocular pressure would typically contain about 0.1% to 15% by weight, and preferably 0.5% to 2.0% by weight of a compound of this invention.

Thus, the compounds of the invention are useful in treating hypertension. They are also of value in the management of acute and chronic congestive heart failure, in the treatment of secondary hyperaldosteronism, primary and secondary pulmonary hypertension, renal failure such as diabetic nephropathy, glomerulonephritis, scleroderma, and the like, renal vascular hypertension, left ventricular dysfunction, diabetic retinopathy, and in the management of vascular disorders such as migraine or Raynaud's disease. The application of the compounds of this invention for these and similar disorders will be apparent to those skilled in the art.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250-350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Preferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

The following examples illustrate the preparation of the compounds of Formula I and their incorporation into pharmaceutical compositions and as such are not to be considered as limiting the invention set forth in the claims appended hereto.

EXAMPLE 1

2-Butyl-3-[4-[(1-carboxy)(1-phenyl)methoxy]phenyl]-methyl-6-methylquinazolin-4(3H)-one Step A: Preparation of 2-n-butyl-6-methylquinazolin-4(1H)-one To a solution of 3.0 g (20 mmol) of 2-amino-5-methyl benzoic acid in 20 mL of dry DMF at 0° C. was added 200 mg of DMAP followed by 6.07 g (60 mmol) of triethylamine and 5.02 g (40 mmol) of valeryl chloride. The resulting mixture was stirred at 0° C. for 30 min. The mixture was heated to 110° C. and monitored by TLC for the formation of the intermediate quinoxazolone ($R_f=0.8$, 40% EtOAc/hexane). Following complete formation of the intermediate 10 g (100 mmol) of $(NH_4)_2CO_3$ was added cautiously. Heating was continued to ensure consumption of the quinoxazolone and formation of the polar ($R_f=0.4$, 40% EtOAc/hexane) quinazolin-4(1H)-one. The reaction mixture was concentrated in vacuo and the residue was taken up in 50 mL of ether and 50 mL of water. The mixture was filtered and the filtrate discarded after washing the residue with 20 mL of ether. The residue was recrystalized from MeOH to give 1.07 g (25%) of the title compound as a white crystalline solid.

$^1$H NMR (300 MHz, CDCl$_3$, ppm): $\delta$0.94 (t, 3H, J=6.7 Hz), 1.50 (m, 2H), 1.83 (m, 2H), 2.49 (s, 3H), 2.78 (t, 2H), 7.60 (m, 2H), 8.05 (m, 1H).

Anal ($C_{13}H_{16}N_2O$), C, H, N.

Step B: Preparation of methyl 2-(4-methylphenoxy)-phenylacetate

To a suspension of KH (212 mg, 1.0 eq) in DMF (3 mL) was added a solution of p-cresol (200 mg; 1.85 mmol) in DMF (2 mL) followed by 18-crown-6 (50 mg, 0.2 eq). After stirring the reaction 45 minutes until the foaming subsides, a solution of methyl 2-bromophenylacetate (424 mg, 1.0 eq) in DMF (1 mL) was added, resulting in a purple solution that slowly faded to yellow. The reaction mixture was stirred 2.5 hours and was then concentrated in vacuo. The residue was chromatographed on a flash silica column (130×30 mm) eluted with 5% ethyl actate/hexane to yield 281 mg (62%) of the title compound ($R_f=0.38$, 5% ethyl acetate/hexane).

$^1$H NMR (300 MHz, CDCl$_3$, ppm): $\delta$2.3 (s, 3H), 3.75 (s, 3H), 5.6 (s, 1H), 6.8–6.9 (d, 2H), 7.0–7.1 (d, 2H), 7.3–7.45 (m, 3H), 7.5–7.6 (d, 2H).

FAB-MS: m/e 257 (M+1).

Step C: Preparation of methyl 2-(4-bromomethylphenoxy)phenylacetate

A solution of the product of Step B (50 mg, 0.205 mmol) NBS (33 mg, 0.9 eq) and AIBN (5 mg, catalytic amount) in CCl$_4$ (2 mL) was heated to reflux for 2 hours, and then concentrated in vacuo. The residue was chromatographed on a flash silica column (20×140 mm) eluted with 5% ethyl acetate/hexane to yield 32 mg (48%) of product ($R_f=0.17$, 5% ethyl acetate/hexane).

$^1$H NMR (300 MHz, CDCl$_3$, ppm): $\delta$3.75 (s, 3H), 4.5 (s, 2H), 5.65 (s, 1H), 6.9–7.0 (d, 2H), 7.3–7.35 (d, 2H), 7.35–7.5 (m, 3H), 7.5–7.6 (d, 2H).

Step D: Preparation of 2-butyl-3-[4-[(1-carbomethoxy)(1-phenyl)methoxy]phenyl]methyl-6-methylquinazolin-4(3H)-one To a suspension of NaH (3 mg, 1.05 eq) in DMF (800 mL) at 0° C. was added 20 mg (0.0925 mmol) of the product of Step A and the reaction mixture was stirred for 15 minutes until the turbidity subsided. Next a solution of the product of Step C (31 mg, 1.0 eq) in DMF (0.2 mL) was added, the reaction was stirred for 18 hours, and then concentrated in vacuo. The residue was chromatographed on a flash silica gel column (120×20 mm) eluted with 15% ethyl acetate/hexane to yield 23 mg (53%) of the title compound ($R_f=0.15$, 15% ethyl acetate/hexane).

$^1$H NMR (300 MHz, CDCl$_3$, ppm): $\delta$0.9–1.0 (t, 3H), 1.3–1.5 (m, 2H), 1.65–1.8 (m, 2H), 2.5 (s, 3H), 2.7–2.8 (t, 2H), 3.75 (s, 3H), 5.3 (s, 2H), 5.6 (s, 1H), 6.85–6.95 (d, 2H), 7.05–7.15 (d, 2H), 7.35–7.45 (m, 3H), 7.5–7.6 (m, 4H), 8.1 (s, 1H).

FAB-MS: m/e 471 (M+1).

Step E: Preparation of 2-butyl-3-[4-[(1-carboxy)(1-phenyl)methoxy]phenyl]methyl-6-methylquinazolin-4(3H)-one To a solution of the product of Step D (22 mg, 0.047 mmol) in MeOH (5 mL) was added 1N NaOH (2 mL). The reaction mixture was stirred 0.5 hours, and was then concentrated in vacuo. The residue was taken up in water and acidified to pH=2 with 1N HCl. Next, the aqueous layer was partitioned with chloroform and extracted 3 times. The combined organic layers were dried (MgSO$_4$), filtered and the filtrate concentrated in vacuo to yield 15 mg (65%) of the title compound ($R_f=0.40$, hexane/ethyl acetate/acetic acid (75:23.5:1.5)).

$^1$H NMR (300 MHz, CDCl$_3$, ppm): $\delta$0.8–0.9 (t, 3H), 1.2–1.4 (m, 2H), 1.55–1.7 (m, 2H), 2.45 (s, 3H), 2.65–2.75 (t, 2H), 5.2–5.4 (br s, 2H), 5.6 (s, 1H), 6.9–7.0 (d, 2H), 7.05–7.15 (d, 2H), 7.35–7.45 (m, 3H), 7.5–7.65 (m, 4H), 8.1 (s, 1H).

FAB-MS: m/e 457 (M+1).

EXAMPLE 2

2-Butyl-3-[4-[(1-carboxy)(1-phenyl)methoxy]3-allyl]-phenyl]methyl-6-methylquinazolin-4(3H)-one Step A: Preparation of 4-(2-propen-1-yloxy)benzyl alcohol To a suspension of NaH (130 mg; 4.33 mmol) in DMF (5 mL) at 0° C. under nitrogen was added a solution of 4-hydroxmethylphenol (512 mg; 4.12 mmol) in DMF (5 mL). After stirring 5 minutes at room temperature, a solution of allyl bromide (375 mL, 4.33 mmol) in DMF (5 mL) was added dropwise. The reaction was stirred for 20 minutes at 0° C., then quenched with water and concentrated in vacuo. The residue was partitioned between water and ethyl acetate. The combined organic layers were washed with 4% HCl, saturated NaHCO$_3$, and then brine, and dried (MgSO$_4$), filtered and concentrated in vacuo to yield 650 mg (97%) of the title compound.

$^1$H NMR (300 MHz, CDCl$_3$, ppm): δ7.27 (dd, 2H), 6.90 (apparent d, 2H), 6.12–5.98 (m, 1H), 5.41 (apparent dd, 1H), 5.29 (dd, 1H), 4.58 (s, 2H), 4.52 (dd, 2H), 1.93 (br s, 1H).

Step B: Preparation of 4-tert-butyldimethylsilyloxymethyl-2-allylphenol

To a solution of the product of Step A (650 mg, 3.96 mmol) in CH$_2$Cl$_2$ (20 mL), cooled to 0° C. under nitrogen, was added triethylamine (612 mL, 4.39 mmol) and a solution of tert-butyldimethylsilyl chloride (631 mg; 4.19 mmol) in CH$_2$Cl$_2$ (2 mL). After stirring at room temperature for 18 hours, the reaction mixture was diluted with ethyl acetate (60 mL), washed with water, and saturated sodium bicarbonate, and then dried (MgSO$_4$). The filtrate was concentrated in vacuo to afford 1.1 g of the title compound which was used crude in the next reaction (R$_f$=0.45, 5% ethyl acetate/hexanes).

$^1$H NMR (300 MHz, CDCl$_3$, ppm): d 7.24 (d, 2H), 6.89 (d, 2H), 6.15–6.00 (m, 1H), 5.42 (apparent d, 1H), 5.30 (apparent d, 1H), 4.68 (s, 2H), 4.53 (apparent dd, 2H), 0.95 (s, 9H), 0.12 (s, 6H).

Step C: Preparation of 4-tert-butyldimethylsilyloxymethyl-2-allylphenol

The product of Step B (0.51 g, 1.83 mmol) was heated to 200° C. under a nitrogen atmosphere for 5 hours. The crude reaction mixture was dissolved in eluant and chromatographed on silica (MPLC, 5/95 ethyl acetate/hexane) to afford 178 mg (35%) of the title compound (R$_f$=0.11, 5% ethyl acetate/hexanes).

$^1$H NMR (300 MHz, CDCl$_3$, ppm): δ7.10 (unsymmetrical d, 2H), 6.78 (d, 2H), 6.09–5.94 (m, 2H), 5.21–5.11 (m, 2H), 5.00 (s, 1H), 4.67 (s, 2H), 3.40 (d, 2H), 0.95 (s, 9H), 0.11 (s, 6H).

FAB-MS: m/e=277 (M+1).

Step D: Preparation of methyl 2-[(4-tert-butyl-dimethylsilyloxymethyl)(2-allyl)phenoxy]-2-phenylacetate To a suspension of KH (1.3 eq) in DMF (1 mL) was added a solution of the product of Step C (157 mg, 0.566 mmol) in DMF (1 mL), followed by 18-crown-6 (30 mg; 0.2 eq). The reaction mixture was stirred for 5 minutes at room temperature. A solution of methyl 2-bromophenylacetate (168 mg, 0.735 mmol) in DMF (1 mL) was added, followed by a catalytic amount of potassium iodide. The reaction was heated to 80° C. for 0.5 hours then stirred at room temperature for 16 hours. After concentration in vacuo, the residue was partitioned between water and ethyl acetate. The combined organic layers were washed with water, brine, then dried (MgSO$_4$). After filtration and concentration in vacuo, the residue was chromatographed on silica (MPLC, ethyl acetate/hexanes (5/95)) to afford 158 mg (66%) of the title compound (R$_f$=0.22, 5% ethyl acetate/hexanes).

$^1$H NMR (300 MHz, CDCl$_3$, ppm): δ7.64–7.57 (dd, 2H), 7.46–7.35 (m, 3H), 7.17–7.06 (m, 2H), 6.72 (d, 1H), 6.12–5.98 (m, 1H), 5.65 (s, 1H), 5.11–5.04 (m, 2H), 4.66 (s, 2H), 3.72 (s, 3H), 3.53 (d, 2H), 0.95 (s, 9H), 0.10 (s, 6H).

FAB MS: consistent with structure.

Step E: Preparation of methyl 2-[(4-bromomethyl)(2-allyl)phenoxy]-2-phenylacetate To a cooled (0° C.) solution of the product of Step D (156 mg, 0.366 mmol) in CH$_3$CN (2 mL), were added carbon tetrabromide (182 mg, 0.55 mmol) and triphenylphosphine (144 mg, 0.55 mmol). After 30 minutes at 0° C., the reaction mixture was allowed to warm to room temperature, at which point acetone (40 mL, 0.55 mmol) was added. After 16 hours at room temperature, the reaction mixture was filtered, the filtrate was concentrated in vacuo, and the residue was purified on a silica gel flash chromatography column eluted with 5% ethyl acetate/hexanes to afford 86 mg (63%) of the title compound (R$_f$=0.13, 5% ethyl acetate/hexanes).

$^1$H NMR (300 MHz, CDCl$_3$, ppm): δ7.67–7.57 (dd, 2H), 7.47–7.37 (m, 3H), 7.27–7.13 (m, 2H), 6.72 (d, 1H), 6.16–5.98 (m, 1H), 5.68 (s, 1H), 5.20–5.08 (m, 2H), 4.49 (s, 2H), 3.73 (s, 3H), 3.54 (d, 2H).

FAB MS: consistent with structure.

Step F: Preparation of 2-Butyl-3-[[4-(1-carbomethoxy) (1-phenyl)methoxy]-3-allylphenyl]methyl-6-methylquinazolin-4(3H)-one To a suspension of NaH (0.514 mmol) in DMF (2 mL) was added 92 mg (0.428 mmol) of 2-butyl-6-methylquinazolin-4(3H)-one (Step A of Example 1) and the reaction mixture was stirred for 30 minutes at room temperature. A solution of the product of Step E (177 mg, 0.471 mmol) in DMF (1.5 mL) was added, and the reaction was stirred at room temperature for 18 hours. The reaction mixture was then concentrated in vacuo and partitioned between water and ethyl acetate. The combined organic layers were washed with water then brine, dried (MgSO$_4$), filtered, and concentrated in vacuo. The residue was chromatographed on silica (MPLC, hexanes/ethyl acetate (4/1)) to afford 96 mg (44%) of the title compound.

$^1$H NMR (300 MHz, CDCl$_3$, ppm): δ8.08 (s, 1H), 7.6–7.49 (br s, 4H), 7.42–7.28 (m, 3H), 7.09–7.01 (br s, 1H), 6.93–6.83 (br dd, 1H), 6.66 (d, 1H), 6.08–5.92 (m, 1H), 5.60 (s, 1H), 5.36–5.22 (br s, 2H), 5.12–4.98 (m, 2H), 3.68 (s, 3H), 3.48 (d, 2H), 3.48 (d, 2H), 2.72 (t, 2H), 2.48 (s, 3H), 1.80–1.65 (m, 2H), 1.40 (q, 2H), 0.90 (t, 3H).

FAB MS: m/e=511 (M+1).

Step G: Preparation of 2-Butyl-3-[4-[(1-carboxy) (1-phenyl)methoxy]-3-allylphenyl]methyl-6-methylquinazolin-4(3H)-one To a solution of the product of Step F (20 mg, 0.039 mmol) in MeOH (2 mL), were added 4 drops of water and 2.0N NaOH (22 mL, 0.043 mmol). After stirring for 18 hours at room temperature, the reaction mixture was concentrated in vacuo, dissolved in water/THF,and treated with HCl (0.15 mL, 1.0N) at room temperature for 30 minutes. The reaction mixture was then concentrated in vacuo and chromatographed on a Sephadex LH-20 column eluted with MeOH to afford 19 mg of crude product, which was recrystallized from MeOH to yield 2 mg (10%) of the title compound.

$^1$H NMR (300 MHz, CD$_3$OD, ppm): δ8.05 (s, 1H), 7.70 (d, 1H), 7.63–7.48 (m, 3H), 7.44–7.28 (m, 3H), 7.08 (s, 1H), 6.99–6.92 (m, 1H), 6.83 (d, 1H), 6.07–5.92 (m, 3H), 5.73 (m, 1H), 5.40 (s, 2H), 5.08–5.88 (m, 2H), 3.46 (br s, 2H), 2.80 (t, 2H), 2.51 (s, 3H), 1.68–1.57 (m, 2H), 1.43–1.28 (m, 2H), 0.88 (t, 3H).

FAB MS: m/e=497 (M+1).

EXAMPLE 3

2-Butyl-3-[4-[(1-carboxy)(1-phenyl)methoxy]-3-propylphenyl]methyl-6-methylquinazolin-4(3H)-one Step A: Preparation of 2-Butyl-3-[4-[(1-carbomethoxy) (1-phenyl)methoxy]-3-propylphenyl]methyl-6-methylquinazolin-4(3H)-one To a solution of the product of Example 2, Step F (20 mg, 0.039 mmol) in $CH_2Cl_2$ (2 mL), was added Wilkinson's catalyst (7.6 mg). The reaction mixture was hydrogenated at 40 psi, room temperature for 4.5 hours. After concentration in vacuo, the residue was chromatagraphed on silica (MPLC, hexanes/ethyl acetate (4/1) to afford 15 mg (78%) of the title compound.

$^1$H NMR (300 MHz, $CDCl_3$, ppm): $\delta$8.10 (s, 1H), 7.63–7.54 (m, 4H), 7.46–7.36 (m, 3H), 7.02 (apparent s, 1H), 6.89 (dd, 1H), 6.63 (d, 1H), 5.62 (s, 1H), 5.32 (br s, 2H), 3.71 (s, 3H), 2.79–2.63 (m, 4H), 2.50 (s, 3H), 1.80–1.60 (m, 2H), 1.48–1.34 (m, 2H), 1.02–0.87 (m, 6H).

FAB-MS: m/e=513 (M+1).

Step B: Preparation of 2-Butyl-3-[4-[(1-carboxy)(1-phenyl)methoxy]-3-propylphenyl]methyl-6-methylquinazolin-4(3H)-one To a solution the product of Example 3, Step A (11 mg; 0.22 mmol) in MeOH (2 mL) was added NaOH (1.5 eq, 2.0N) and a few drops of water. After stirring for 20 hours at room temperature, the reaction mixture was concentrated in vacuo, dissolved in water/THF, treated with HCl (5 eq) for 30 minutes at room temperature, concentrated in vacuo, and chromatographed on a Sephadex LH-20 column eluting with MeOH to afford 11 mg (99%) of the title compound.

$^1$H NMR (300 MHz, $CD_3OD$, ppm): $\delta$8.19 (s, 1H), 7.88 (d, 1H), 7.68 (d, 1H), 7.58 (dd, 2H), 7.48–7.33 (m, 3H), 7.18 (s, 1H), 7.08 (d, 1H), 6.84 (d, 1H), 5.70 (s, 1H), 5.48 (s, 2H), 3.15–3.03 (m, 2H), 2.69 (t, 2H), 2.53 (s, 3H), 1.72–1.5 (m, 4H), 1.49–1.34 (m, 2H), 0.98–0.84 (m, 6H).

FAB-MS: m/e=499 (M+1).

EXAMPLE 4

2-Butyl-3-[4-[(1-carboxy)(1-phenyl)methoxy]-3-chlorophenyl]methyl-6-methylquinazolin-4(3H)-one Step A: Preparation of methyl 2-(2-chloro-4-methylphenoxy)-2-phenylacetate To a suspension of 0.282 g (7.04 mmol) of a 60% oil dispersion of sodium hydride in DMF was added 1.00 g (7.04 mmol) of 2-chloro-4-methylphenol and the mixture was stirred under an $N_2$ atmosphere at room temperature. After 10 minutes, a solution of 1.94 g (8.45 mmol) of methyl 2-bromophenylacetate dissolved in 10 mL of DMF was added and the reaction was stirred an additional 1.5 hours. The reaction was then diluted into ethyl acetate, washed with water, dried ($MgSO_4$), filtered and evaporated. The residue was purified on a silica gel flash chromatography column eluted with 4% ethyl acetate/hexane to afford 1.70 g (83%) of the title compound.

$^1$H NMR (300 MHz, $CDCl_3$, ppm): $\delta$2.20 (s, 3H), 3.70 (s, 3H), 5.60 (s, 1H), 6.70–6.80 (d, 1H), 6.85–6.95 (d, 1H), 7.20 (br s, 1H), 7.20–7.30 (m, 3H), 7.55–7.65 (m, 2H).

EI-MS: m/e 290 (M+).

Step B: Preparation of methyl 2-(2-chloro-4-bromomethylphenoxy)-2-phenylacetate

To a solution of 1.70 g (5.86 mmol) of the product from Step A dissolved in 20 mL of $CCl_4$ was added 1.04 g (5.86 mmol) of N-bromosuccinimide and 50 mg (catalytic amount) of AIBN. The reaction mixture was stirred and heated at reflux for 7 hours, then an additional 0.20 g of NBS was added. The reaction was refluxed for 48 hours, then cooled and concentrated in vacuo. The residue was purified on a silica gel flash chromatography column eluted with 10% ethyl acetate/hexane to afford 0.730 g (34%) of the title compound.

$^1$H NMR (300 MHz, $CDCl_3$, ppm): $\delta$3.70 (s, 3H), 4.40 (s, 2H), 5.65 (s, 1H), 6.75–6.85 (d, 1H), 7.10–7.20 (d, 1H), 7.30–7.45 (m, 4H), 7.55–7.65 (m, 2H).

FAB-MS: m/e 369 (M+1).

Step C: Preparation of 2-butyl-3-[4-[(1-carbomethoxy) (1-phenyl)methoxy]-3-chlorophenyl]methyl-6-methylquinazolin-4(3H)-one To a half suspension of 62 mg (0.287 mmol) of the product of Step A of Example 1 in 1.0 mL of anhydrous DMF was added 12 mg (1.05 eq) of a 60% oil dispersion of sodium hydride and the reaction mixture was stirred under an $N_2$ atmosphere. After stirring 10 minutes at room temperature, a solution of 0.127 g (1.2 eq) of the product of Step B dissolved in 1.0 mL DMF was added to the solution of the anion. The reaction mixture was then stirred overnight, then partitioned between water and ethyl acetate. The organic layer was separated, dried ($MgSO_4$), filtered and evaporated in vacuo. The residual oil was purified on a silica gel flash chromatography column eluted with 30% ethyl acetate/hexane to afford 76 mg (52%) of the title compound.

$^1$H NMR (300 MHz, $CDCl_3$, ppm): $\delta$0.87–0.94 (t, 3H), 1.32–1.45 (m, 2H), 1.67–1.78 (m, 2H), 2.42 (s, 3H), 2.66–2.72 (t, 2H), 3.70 (s, 3H), 5.30 (br s, 2H), 5.60 (s, 1H), 6.77 (d, 1H), 6.94 (dd, 1H), 7.18 (s, 1H), 7.33–7.42 (m, 3H), 7.53–7.61 (m, 4H), 8.06 (s, 1H).

FAB-MS: m/e 505, 507 (M+1, 3:1 ratio).

Step D: Preparation of 2-butyl-3-[4-[(1-carboxy)(1-phenyl)methoxy]-3-chlorophenyl]methyl-6-methylquinazolin-4(3H)-one To a solution of 72 mg of the product of Step C dissolved in 2 mL of methanol, was added 0.25 mL of a 1N solution of NaOH and the reaction mixture was stirred at room temperature for 3 days. The reaction mixture was then adjusted to pH 7 with 1N HCl, caoncentrated in vacuo, and the residue was applied to a silica gel flash chromatography column and eluted with $CHCl_3/MeOH/NH_4OH$ (80:15:1). Evaporation of the purified fractions and drying in vacuo afforded 50 mg (71%) of the title compound.

$^1$H NMR (300 MHz, $CD_3OD$, ppm): $\delta$0.92–0.98 (t, 3H), 1.37–1.48 (m, 2H), 1.66–1.77 (m, 2H), 2.54 (s, 3H), 2.78–2.84 (t, 2H), 5.40 (s, 2H), 5.68 (s, 1H), 7.01–7.10 (m, 2H), 7.31–7.44 (m, 4H), 7.58–7.72 (m, 4H), 8.07 (s, 1H).

FAB-MS: m/e 491, 493 (M+1, 3:1 ratio).

EXAMPLE 5

3-[4-[(1-Carboxy)(1-phenyl)methoxy]-3-chloro-5-methoxyphenyl]methyl-6-[(N-methyl)(N-iso-butyloxycarbonyl)amino]-2-propylquinazolin-4(3H)-one Step A: Preparation of 2-propyl-6-nitro-quinazolin-4(1H)-one To a suspension of 48.94 g (0.3 mol) of 3-nitro-5-amino-benzonitrile in 500 mL of $CH_2Cl_2$ was added 63 mL of $Et_3N$, 3 g DMAP and lastly, dropwise, 45.5 g (0.45 mol) of butyryl chloride. A mild exothermic reaction ensued. The mixture was allowed to stir for 2 days (monitored by TLC with 50% EtOAc/hexanes). The solution was washed with 1N HCl (2×100 mL), water (1×100 mL), saturated $NaHCO_3$ (2×100 mL), brine (1×100 mL) and dried over MgSO₄. The suspension was filtered and concentrated in vacuo. The residue was suspended in a mixture of 600 mL of MeOH and 200 mL of water in a three neck round bottom flask. To this was added gradually 140 mL of 5N NaOH (0.7 mol) solution followed by the dropwise addition of 80 mL of 30% $H_2O_2$ (0.7 mmol) solution (exothermic). The mixture was refluxed overnight, cooled to room temperature and filtered. The filtrate was acidified with 1N HCl cooled to 5° C. and filtered. The quinazolinone was recrystallized from hot MeOH to give 38 g (54%) of the title compound as pale brown fine crystals.

¹H NMR (300 MHz, CDCl₃, ppm): δ1.10 (t, 3H, J=7.8 Hz), 1.93 (m, 2H), 2.79 (t, 2H, J=7.3 Hz), 7.81 (d, 1H, J=8.9 Hz), 8.55 (dd, 1H, J=2.4, 8.8 Hz), 9.14 (d, 1H, J=2.4 Hz), 10.72 (br s, 1H).

Step B: Preparation of 3-(4,4'-dimethoxybenzhydryl)-2-propyl-6-nitro-quinazolin-4(3H)-one To a suspension of 1.01 g (33.7 mmol) of 80% sodium hydride in 20 mL of dry DMF was added at 0° C. 7.5 g (32 mmol) of the product of Step A as a solid. The reaction mixture was diluted with a further 50 mL of DMF to assist stirring. After hydrogen evolution was complete, a solution of 8.8 g (33.7 mmol) of 4,4'-dimethoxybenzhydryl chloride in 20 mL of dry DMF was added dropwise. The reaction mixture was stirred overnight and then poured into 300 mL of 0.1N NaOH. The precipitate was collected by filtration and dried under vacuum to give 12.1 g (94%) of a yellow solid.

¹H-NMR (300 MHz, CDCl₃, ppm): δ0.87 (t, 3H, J=7.3 Hz), 1.58 (br m, 2H), 2.72 (t, 2H, J=7.8 Hz), 3.80 (s, 6H), 6.88 (d, 4H, J=9 Hz), 7.19 (d, 4H, J=9.0 Hz), 7.73 (d, 1H, J=8.9 Hz), 8.48 (dd, 1H, J=2.8, 9.0 Hz), 9.08 (d, 1H, J=2.8 Hz).

Step C: Preparation 6-amino-3-(4,4'-dimethoxybenzhydryl)-2-propyl-quinazolin-4(3H)-one A solution of 12.1 g (26.0 mmol) of the product of Step B dissolved in 250 mL of EtOAc was hydrogenated under atmospheric pressure over three days in the presence of three portions of 1.2 g of 10% Pd/C added daily. The mixture was filtered through celite and concentrated in vacuo to give an oil. The product was purified by flash chromatography over silica gel eluted with 50% EtOAc/hexanes to give 7.8 g (72%) of the amine.

¹H-NMR (300 MHz, CDCl₃, ppm): δ0.82 (t, 3H, J=7.2 Hz), 1.49 (br m, 2H), 2.61 (t, 2H, J=7.81 Hz), 3.79 (s, 6H), 3.90 (br s, 2H), 6.85 (d, 4H, J=8.8 Hz), 7.08 (dd, 1H, J=2.8, 8.7 Hz), 7.20 (d, 4H, J=8.4 Hz), 7.42 (d, 1H, J=2.7 Hz), 7.47 (d, 1H, J=8.7 Hz).

Step D: Preparation of 3-(4,4'-dimethoxybenzhydryl)-6-[(N-methyl)(N-isobutyloxycarbonyl)amino]-2-propyl-quinazolin-4(3H)-one To a suspension of 81.5 mg (2.7 mmol) of 80% NaH in 3 mL of dry DMF at 0° C. under nitrogen was added dropwise a solution of 1.03 g (2.5 mmol) of 6-amino-3-(4,4'-dimethoxybenzhydryl)-2-propylquinazolin-4(3H)-one dissolved in 3 mL of DMF. The resulting mixture was stirred for 30 minutes and then treated with 0.35 mL (2.7 mmol) of neat isobutylchloroformate. The solution was stirred for 30 minutes and then treated with 2.97 mL (2.97 mmol) of a 1M solution of lithium bis(trimethylsilyl)amide in THF. The dark solution was stirred for a further 30 minutes at 0° C. and then was treated with 0.2 mL (3.26 mmol) of neat iodomethane. The mixture was stirred overnight at room temperature, poured into 50 mL of EtOAc and washed consecutively with water (2×10 mL), brine (1×10 mL) and dried over MgSO₄. The product was purified by flash chromatography over silica gel eluted with 30% EtOAc/hexanes to give 0.9 g (71%) of the title compound as an oil.

¹H-NMR (300 MHz, CDCl₃, ppm): δ0.82-0.91 (m, 6H), 0.96 (d, 3H, J=6.8 Hz), 1.52 (m, 2H), 1.88 (m, 1H), 2.67 (br t, 2H), 3.35 (s, 3H), 3.80 (s, 6H), 3.90 (d, 2H, J=6.6 Hz), 6.87 (d, 4H, J=8.8 Hz), 7.20 (d, 4H, J=8.8 Hz), 7.61 (m, 1H), 7.78 (m, 1H), 8.01 (d, 1H, 2H).

Step E: Preparation of 6-[(N-methyl)(N-isobutyloxycarbonyl)amino]-2-propylquinazolin-4(3H)-one The product of Step D (0.9 g, 1.7 mmol) was added to 3.0 mL of a 10:1 mixture of trifluoroacetic acid and anisole. The solution was stirred for 4 hours, concentrated in vacuo and the residue was purified by flash chromatography over silica gel eluted with 50% EtOAc/hexanes to give 0.47 g (88%) of the title compound as a white solid.

¹H-NMR (300 MHz, CDCl₃, ppm): δ0.89 (d, 6H, J=6.7 Hz), 1.07 (t, 3H, J=7.4 Hz), 1.92 (m, 2H), 2.76 (t, 2H, J=7.8 Hz), 3.40 (s, 3H), 3.93 (d, 2H, J=6.6 Hz), 7.70 (m, 2H), 8.10 (d, 1H, J=2.6 Hz).

Step F: Preparation of methyl 2-(2-chloro-4-hydroxymethyl-6-methoxyphenoxy)-2-phenylacetate To a solution of 0.500 g (2.65 mmol) of 3-chloro-4-hydroxy-5-methoxybenzyl alcohol (Bader) and 0.668 g (1.1 eq) of methyl 2-bromophenylacetate dissolved in 5 mL acetone was added 0.733 g (2 eq) of anhydrous potassium carbonate and the reaction mixture was stirred and refluxed overnight. The reaction mixture was cooled to room temperature, filtered and evaporated in vacuo. The residual oil was purified on a silica gel flash chromatography column eluted with 35% ethyl acetate/hexane to afford 0.570 g (64%) of the title compound.

¹H NMR (300 MHz, CDCl₃, ppm): δ1.65-1.75 (t, 1H), 3.70 (s, 3H), 3.80 (s, 3H), 4.55 (d, 2H), 5.75 (s, 1H), 6.80 (s, 1H), 6.90 (s, 1H), 7.30-7.40 (m, 3H), 7.50-7.60 (m, 2H).

FAB-MS: m/e 337, 339 (M+1, 3:1 ratio).

Step G: Preparation of 2-(4-bromomethyl-2-chloro-6-methoxyphenoxy)-2-phenylacetate To a stirred and cooled (0° C.) solution of 0.570 g (1.69 mmol) of the product of Step A dissolved in 6 mL of $CH_2Cl_2$ was added 0.702 g (2.11 mmol) of carbon tetrabromide and 0.555 g (2.11 mmol) of triphenylphosphine. After the addition the reaction mixture was allowed to warm to room temperature and was stirred 4 hours. The mixture was then evaporated in vacuo and purified on a silica gel flash chromatography column eluted with 20% ethyl acetate/hexane to afford 0.580 g (86%) of the title compound.

¹H NMR (300 MHz, CDCl₃, ppm): δ3.75 (s, 3H), 3.80 (s, 3H), 4.35 (s, 2H), 5.65 (s, 1H), 6.80 (s, 1H), 6.95 (s, 1H), 7.30-7.40 (m, 3H), 7.50-7.60 (m, 2H).

FAB-MS: m/e 398, 400, 402 (M+1).

Step H: Preparation of 3-[4-[(1-carbomethoxy)(1-phenyl)methoxy]-3-chloro-5-methoxyphenyl]methyl-6-[N-methyl)(N-iso-butyloxycarbonyl)amino]-2-propyl-quinazolin-4(3H)-one To a half suspension of 80 mg (0.252 mmol) of the product of Step E in 0.5 mL of anhydrous DMF was added 10.6 mg (1.05 eq) of a 60% oil dispersion of sodium hydride and the reaction mixture was stirred under an $N_2$ atmosphere. After stirring 40 minutes at room temperature, a solution of 0.111 g (1.1 eq) of the product of Step G dissolved in 0.5 mL DMF was added to the solution of the anion. The reaction mixture was then stirred overnight, then partitioned between water and ethyl acetate. The organic layer was separated, dried (MgSO$_4$), filtered and evaporated in vacuo. The residual oil was purified on a silica gel flash chromatography column eluted with 40% ethyl acetate/hexane to afford 100 mg (63%) of the title compound.

$^1$H NMR (300 MHz, CDCl$_3$, ppm): δ0.84–1.01 (m, 9H), 1.58–2.02 (m, 3H), 2.63–2.68 (t, 2H), 3.38 (s, 3H), 3.71 (s, 3H), 3.73 (s, 3H), 3.91 (d, 2H), 5.20–5.30 (br s, 2H), 5.72 (s, 1H), 6.58–6.64 (m, 1H), 6.68 (d, 1H), 7.28–7.34 (m, 3H), 7.48–7.55 (m, 2H), 7.61 (d, 1H), 7.72 (d, 1H), 8.07 (d, 1H).

FAB-MS: m/e 636, 638 (M+1, 3:1 ratio).

Step I: Preparation of 3-[4-[(1-carboxy)(1-phenyl)methoxy)]-3-chloro-5-methoxyphenyl]methyl-6-[(N-methyl)(N-iso-butyloxycarbonyl)amino]-2-propylquinazolin-4(3H)-one To a solution of 97 mg (0.15 mmol) of the product of Step H dissolved in 2 mL of methanol, was added 0.25 mL of a 1N solution of NaOH and the reaction mixture was stirred at room temperature for 2.5 hours. The reaction mixture was then adjusted to pH 6 with 1N HCl, caoncentrated in vacuo, and the residue was applied to a silica gel flash chromatography column and eluted with CHCl$_3$/MeOH/NH$_4$OH (80:15:1). Evaporation of the purified fractions and drying in vacuo afforded 60 mg (63%) of the title compound.

$^1$H NMR (300 MHz, CDCl$_3$, ppm): δ0.88–1.06 (m, 9H), 1.68–1.82 (m, 2H), 1.85–2.04 (m, 1H), 2.76 (t, 2H), 3.43 (s, 3H), 3.68 (s, 3H), 3.95 (d, 2H), 5.38 (s, 2H), 5.67 (s, 1H), 6.68 (d, 1H), 6.74 (d, 1H), 7.26–7.33 (m, 3H), 7.48–7.54 (m, 2H), 7.72 (d, 1H), 7.82 (dd, 1H), 8.14 (d, 1H).

EXAMPLE 6

3-[4-[(1-Carboxy)(1-phenyl)methoxy]-3-propylphenyl]methyl-6-[(N-methyl)(N-iso-butyloxycarbonyl)amino]-2-propylquinazolin-4(3H)-one Step A: Preparation of methyl 4-(2-propen-1-yl)oxybenzoate A 2 L flask was equipped with a mechanical stirrer, a reflux condenser and a stopper, then charged with 50.05 g (0.329 mol) of methyl 4-hydroxybenzoate, 960 mL of acetone, 22.50 g (1.625 mol) of anhydrous potassium carbonate, 80.5 mL (112.6 g, 0.932 mol) of allyl bromide and the mixture was stirred and refluxed for 14 hours. The mixture was cooled to room temperature, filtered and concentrated to an oil. The residual oil was purified by distillation (97° C. @ 0.03 mm Hg) to afford 53.52 g (86%) of the title compound.

$^1$H NMR (300 MHz, CDCl$_3$, ppm): δ3.84 (s, 3H), 4.56 (d, J=7 Hz, 2H), 5.28 (dd, J=3,12 Hz, 1H), 5.40 (dd, J=3,19 Hz, 1H), 5.96–6.10 (m, 1H), 6.90 (d, J=10 Hz, 2H), 7.96 (d, J=10 Hz, 2H).

FAB-MS: m/e 193 (M+1).

Step B: Preparation of methyl 4-hydroxy-3-(2-propen-1-yl)benzoate

A solution of 15.05 g (78.3 mmol) of the product of Step A in 25 mL of 1,2-dichlorobenzene was magnetically stirred and refluxed (183° C.) under an argon atmosphere for 18 hours. At this point, the reaction mixture was cooled to room temperature and applied to a 6 cm diameter by 18 cm silica gel flash chromatography column and eluted with 25% ethyl acetate-hexane to separate the 1,2-dichlorobenzene, then with 40% ethyl acetate-hexane to elute the product. The product fractions were concentrated in vacuo and the residual oil was crystallized from hexane to afford 13.70 g (91%) of the title compound.

$^1$H NMR (300 MHz, CDCl$_3$, ppm): δ3.42 (d, J=8 Hz, 2H), 3.88 (s, 3H), 5.14–5.20 (m, 2H), 5.48 (s, 1H), 5.94–6.06 (m, 1H), 6.82 (d, J=12 Hz, 1H), 7.80–7.85 (m, 2H).

FAB-MS: m/e 193 (M+1).

Step C: Preparation of methyl 4-(tert-butyldimethylsilyloxy)-3-(2-propen-1-yl)benzoate To a solution of 5.168 g (26.9 mml) of the product of Step B in 50 mL of dichloromethane was added 4.40 mL (2.95 mmol) of triethylamine, 4.46 g (2.95 mmol) of tert-butyldimethylchlorosilane, 0.100 g of 4-dimethylaminopyridine, and the reaction mixture was stirred at room temperature for 2 hours. The mixture was then diluted with 50 mL dichloromethane, washed with 100 mL 1 N hydrochloric acid, dried (MgSO$_4$), filtered and evaporated. The residual oil (7.993 g, 97%) was used in the next step without further purification.

$^1$H NMR (300 MHz, CDCl$_3$, ppm): δ0.24 (s, 6H), 1.02 (s, 9H), 3.36 (d, J=8 Hz, 2H), 3.84 (s, 3H), 4.98–5.08 (m, 2H), 5.88–6.03 (m, 1H), 6.78 (d, J=11 Hz, 1H), 7.76–8.40 (m, 2H).

FAB-MS: m/e 307 (M+1).

Step D: Preparation of 4-(tert-butyldimethylsilyloxy)-3-(2-propen-1-yl)benzyl alcohol To a magnetically stirred solution of 8.523 g (28.0 mmol) of the product from step C in 35 mL of anhydrous THF was added 15.0 mL of a 1.0M solution of lithium aluminum hydride in THF, and the reaction mixture was stirred under a nitrogen atmosphere for 2 hours. At this point, the reaction was quenched by cautious addition of 10 mL water, the resulting precipitate was dissolved by addition of 1.0N hydrochloric acid and the product was extracted into ethyl acetate. The organic layer was separated, dried (MgSO$_4$), filtered and evaporated in vacuo to afford 7.258 g (93%) of the title compound.

$^1$H NMR (300 MHz, CDCl$_3$, ppm): δ0.20 (s, 6H), 1.00 (s, 9H), 3.34 (d, J=8 Hz, 2H), 3.84 (s, 1H), 4.57 (s, 2H), 4.97–5.07 (m, 2H), 5.88–6.03 (m, 1H), 6.86 (d, J=10 Hz, 1H), 7.05–7.14 (m, 2H).

FAB-MS: m/e 279, 261 (M+1).

Step E: Preparation of 4-hydroxy-3-(2-propen-1-yl)benzyl alcohol

To a solution of approximately 7.26 g (2.6 mmol) of the crude product of Step D, dissolved in 50 mL of anhydrous THF was added 26 mL (2.6 mmol) of tetra-n-butylammonium fluoride and the reaction mixture was stirred at room temperature for 16 hours. The mixture was then evaporated in vacuo and the residual oil was purified on a silica gel flash chromatography column eluted with 5% methanol/chloroform to afford 3.386 g (79%) of the title compound as a colorless oil.

$^1$H NMR (300 MHz, CDCl$_3$, ppm): δ2.12 (br s, 1H), 3.35 (d, J=8 Hz, 2H), 4.54 (s, 3H), 5.05–5.15 (m, 2H), 5.90 (br s, 1H), 5.90–6.05 (m, 1H), 6.70 (d, J=10 Hz, 1H), 7.02–7.10 (m, 2H).

FAB-MS: m/e 165 (M+1).

Step F: Preparation of 4-hydroxy-3-propylbenzyl alcohol

To a solution of 0.370 g (2.25 mmol) of the product of Step E dissolved in 25 mL of absolute ethanol was added 53 mg of a 5% rhodium on carbon catalyst and the mixture was shaken under a 40 psig pressure of hydrogen on a Parr apparatus. After 30 minutes, the reaction mixture was removed, filtered and evaporated in vacuo. The residue was purified on a silica gel flash chromatography column eluted with 35% ethyl acetate/hexane to afford the title compound.

¹H NMR (300 MHz, CDCl₃, ppm): δ0.95 (t, J=8 Hz, 3H), 1.55–1.68 (m, 2H), 2.22 (br s, 1H), 2.57 (t, J=8 Hz, 2H), 4.56 (s, 2H), 5.93 (br s, 1H), 6.66 (d, J=10 Hz, 1H), 7.00 (dd, J=2, 10 Hz, 1H), 7.08 (d, J=2 Hz, 1H).

FAB-MS: m/e 167 (M+1).

Step G: Preparation of methyl (4-hydroxymethyl-2-propylphenoxy)-2-phenylacetate

To a solution of 0.484 g (2.91 mmol) of the product of Step F dissolved in 12 mL of acetone were added 0.667 g (2.91 mmol) of methyl 2-bromophenylacetate, 0.804 g (5.82 mmol) of anhydrous K₂CO₃ and the mixture was stirred and heated at reflux for 5 hours. The mixture was then cooled, filtered and evaporated in vacuo. The residual oil was purified on a silica gel flash chromatography column eluted with 30% ethyl acetate/hexane to afford 0.756 g (83%) of the title compound.

¹H NMR (300 MHz, CDCl₃, ppm): δ0.95 (t, J=8 Hz, 3H), 1.58 (br s, 1H), 1.60–1.75 (m, 2H), 2.70 (t, J=8 Hz, 2H), 3.68 (s, 3H), 4.57 (m, 2H), 5.62 (s, 1H), 6.68 (d, J=10 Hz, 1H), 7.07 (dd, J=2, 10 Hz, 1H), 7.16 (d, J=2 Hz, 1H), 7.32–7.44 (m, 3H), 7.55–7.60 (m, 2H).

FAB-MS: m/e 315 (M+1).

Step H: Preparation of methyl (4-bromomethyl-2-propylphenoxy)-2-phenylacetate

To a stirred (0° C.) solution of 0.750 g (2.31 mmol) of the product of Step G, and 0.949 g (2.86 mmol) of carbon tetrabromide dissolved in 7 mL of methylene chloride was added 0.751 g of triphenylphosphine (2.86 mmol) in portions. After the addition was complete, the reaction mixture was stirred and allowed to warm to room temperature over 1 hour. The reaction mixture was then evaporated in vacuo, and the residue was purified on a silica gel flash chromatography column eluted with 10% ethyl acetate/hexane to afford 0.703 g (78%) of the title compound.

¹H NMR (300 MHz, CDCl₃, ppm): δ0.95 (t, J=8 Hz, 3H), 1.60–1.75 (m, 2H), 2.70 (t, J=8 Hz, 2H), 3.69 (s, 3H), 4.44 (s, 2H), 5.62 (s, 1H), 6.64 (d, J=10 Hz, 1H), 7.12 (dd, J=2, 10 Hz, 1H), 7.18 (d, J=2 Hz, 1H), 7.34–7.44 (m, 3H), 7.53–7.58 (m, 2H).

Step I: Preparation of 3-[4-[(1-carboxmethoxy)(1-phenyl)methoxy]-3-propylphenyl]methyl-6-[(N-methyl)(N-iso-butyloxycarbonyl)amino]-2-propyl-quinazolin-4(3H)-one To a solution of 115 mg (0.36 mmol) of the product of Step E from Example 5 in 1.5 mL of anhydrous DMF was added 15.0 mg (0.36 mmol) of a 60% oil dispersion of sodium hydride and the reaction mixture was stirred under an N₂ atmosphere. After stirring 45 minutes at room temperature, a solution of 0.137 g (0.36 mmol) of the product of Step H dissolved in 0.5 mL DMF was added to the solution of the anion. The reaction mixture was then stirred an additional hour at room temperature, then partitioned between water and ethyl acetate. The organic layer was separated, dried (MgSO₄), filtered and evaporated in vacuo. The residual oil was purified on a silica gel flash chromatography column eluted with 35% ethyl acetate/hexane to afford 0.060 g (49%) of the title compound.

¹H NMR (300 MHz, CDCl₃, ppm): δ0.85 (d, 6H), 0.92 (t, 3H), 0.96 (t, 3H), 1.55–2.00 (m, 5H), 2.60–2.75 (m, 4H), 3.36 (s, 3H), 3.77 (s, 3H), 3.90 (d, 2H), 5.28 (br s, 2H), 5.57 (s, 1H), 6.63 (d, 1H), 6.85 (dd, 1H), 6.99 (d, 1H), 7.30–7.42 (m, 3H), 7.50–7.60 (m, 3H), 7.55 (dd, 1H), 7.60 (d, 1H), 8.08 (d, 1H).

FAB-MS: m/e 614 (M+H).

Step J: Preparation of 3-[4-[(1-carboxy)(1-phenyl)methoxy]-3-propylphenyl]methyl-6-[(N-methyl)(N-iso-butyloxycarbonyl)amino]-2-propylquinazolin-4(3H)-one To a solution of 60 mg (0.098 mmol) of the product of Step I dissolved in 2 mL of methanol, was added 0.25 mL of a 1N solution of NaOH and the reaction mixture was stirred at room temperature for 4 hours. The reaction mixture was then adjusted to pH 7 with 1N HCl, concentrated in vacuo, and the residue was applied to a silica gel flash chromatography column and eluted with 10% MeOH/CHCl₃. Evaporation of the purified fractions and drying in vacuo afforded 33 mg (57%) of the title compound.

¹H NMR (300 MHz, CD₃OD, ppm): δ0.88–1.05 (complex, 12H), 1.56–1.67 (m, 2H), 1.72–1.84 (m, 2H), 1.87–2.00 (m, 1H), 2.55–2.65 (m, 1H), 2.75–2.86 (m, 3H), 3.42 (s, 3H), 3.95 (d, 2H), 5.38 (br s, 2H), 5.43 (s, 1H), 6.85 (d, 1H), 6.94 (dd, 1H), 7.05 (d, 1H), 7.28–7.38 (m, 3H), 7.62–7.70 (m, 2H), 7.71 (d, 1H), 7.83 (dd, 1H), 8.15 (d, 1H).

FAB-MS: m/e 600 (M+H).

EXAMPLE 7

5-Butyl-4-[4-[(1-carboxy)(1-phenyl)methoxy]phenyl]-methyl-2-(2-chlorophenyl)-2,4-dihydro-3H-1,2,4-triazol-3-one Step A: Preparation of ethyl valerimidate (Free Base)

A 12.7 g (76.7 mmol) sample of ethyl valerimidate hydrochloride (prepared from valeronitrile, ethanol, and hydrogen chloride gas as described by A. J. Hill and I. Rabinowitz, J. Am. Chem. Soc., 1926, 48, 734) was dissolved in 33% (w/w) potassium carbonate solution (made by dissolving 15 g of K₂CO₃ in 30 mL of H₂O) and immediately extracted with either (3×40 mL). The combined ether layers were dried over Na₂SO₄, filtered, and concentrated in vacuo to give 7.09 g (72%) of the product as a clear oil, which was used directly in the next step.

¹H NMR (300 MHz, CDCl₃, ppm): δ0.88 (t, J=7 Hz, 3H), 1.24 (t, J=7 Hz, 3H), 1.31 (m, 2H), 1.50 (m, 2H), 2.19 (t, J=7.5 Hz, 2H), 4.06 (q, J=7 Hz, 2H), 6.84 (br s, 1H).

Step B: Preparation of ethyl N-carbethoxyvalerimidate

A solution of 6.5 g (50.3 mmol) of ethyl valerimidate (free base) in 90 mL of dry CH₂Cl₂ was treated with 7.71 mL (5.60 g, 55.3 mmol) of triethylamine. The resulting solution was stirred under N₂ at −10° C. in an ice-salt bath as a solution of 4.81 mL (5.46 g, 50.3 mmol) of ethyl chloroformate in 10 mL of CH₂Cl₂ was added dropwise over 25 minutes. Upon completion of the addition, the cooling bath was removed, and the mixture was stirred at room temperature for 2 hours. Next, the solvent was removed by evaporation in vacuo. The residue was taken up in hexane and filtered to remove triethylamine hydrochloride. Concentration of the filtrate yielded 7.08 g (70%) of the product as a yellow oil, suitable for use in the next step without further purification. NMR indicated a mixture of syn and anti isomers. TLC (98:2 CH₂Cl₂-MeOH) showed a close pair of spots, R_f 0.48, 0.52.

¹H NMR (200 MHz, CDCl₃, ppm): δ0.86 (distorted t, J=7.5 Hz, 3H), 2.15–2.35 (, 8H), 2.4–2.65 (m, 2H), 2.19, 2.35 (t, J=7.5 Hz, 2H total), 4.0–4.2 (m, 2H).

EI-MS: m/e 201 (M⁺).

Step C: Preparation of 5-butyl-2-(2-chlorophenyl)-2,4-dihydro-3H-1,2,4-triazol-3-one To a solution of 285 mg (2 mmol) of (2-chlorophenyl)hydrazine (generated from the hydrochloride by partitioning between ether and 1N Na$_2$CO$_3$) in 3 mL of toluene was added 442 mg (2.2 mmol) of ethyl N-carboethoxyvalerimidate (Example 4 Step B). The mixture was heated at 45°-50° C. for 45 minutes. At this time the mixture was treated with 307 mL (223 mg, 2.2 mmol) of triethylamine and then heated overnight at 95° C. The mixture was cooled and concentrated in vacuo. Flash chromatography of the residue on silica gel (gradient elution with 0.6-2% methanol in CH$_2$Cl$_2$) gave 257 mg (51%) of the product as an off-white solid, mp 103°-104° C., homogeneous by TLC in 19:1 CH$_2$Cl$_2$-MeOH.

$^1$H NMR (200 MHz, CDCl$_3$, ppm): δ0.92 (t, J=7 Hz, 3H), 1.38 (m, 2H), 1.68 (m, 2H), 2.57 (t, J=7.5 Hz, 2H), 7.3-7.55 (m, 4H), 12.04 (br s, 1H).

FAB-MS: m/e 252 (M+1).

Analysis for C$_{12}$H$_{14}$ClN$_3$O: Calcd: C, 57.26; H, 5.61; N, 16.69; Found: C, 57.31; H, 5.69; N, 16.58.

Step D: Preparation of 5-butyl-4-[4-[(1-carbomethoxy)(1-phenyl)methoxy]phenyl]methyl-2-(2-chlorophenyl)-2,4-dihydro-3H-1,2,4-triazol-3-one A mixture of 64 mg (0.254 mmol) of the product of Step C, 6.1 mg (0.254 mmol) of sodium hydride, and 0.5 mL of DMF was stirred under N$_2$ at room temperature for 2.5 hours. To this was then added 100 mg (0.299 mmol) of methyl 2-(4-bromomethylphenoxy)-2-phenylacetate (from Example 1, Step C), dissolved in a minimal amount of DMF. Stirring was continued for 48 hours. The mixture was then partitioned between 5 mL H$_2$O and 8 mL EtOAc, and the aqueous layer was further extracted with 2×8 mL EtOAc. The combined organic layers were washed with 2×10 mL H$_2$O and 1×10 mL brine, and dried over anhydrous Na$_2$SO$_4$. The filtrate was evaporated in vacuo, and the residue flash chromatographed over 40 mL silica gel (gradient elution with 0.5% to 2.0% methanol in CH$_2$Cl$_2$) to give 62 mg of the title compound as a colorless oil (48%), homogeneous by TLC in 50:1 CH$_2$Cl$_2$—MeOH.

$^1$H NMR (400 MHz, CDCl$_3$, ppm): δ0.85 (t, J=7.3 Hz, 3H), 1.33 (m, 2H), 1.56 (m, 2H), 2.42 (t, J=7.6 Hz, 2H), 3.72 (s, 3H), 4.81 (s, 2H), 5.61 (s, 1H), 6.86-6.95 (m, 2H), 7.10-7.60 (m, 11H).

FAB-MS: m/e 506 (M+1).

Step E: Preparation of 5-Butyl-4-[4-[(1-carboxy)(1-phenyl)methoxy]phenyl]methyl-2-(2-chlorophenyl)-2,4-dihydro-3H-1,2,4-triazol-3-one A solution of 49 mg (0.097 mmol) of the above ester (Step D) in THF was treated with 0.5 mL (5 equivalents) of 1N NaOH in MeOH at room temperature for 2 days. Volatiles were evaporated and the residue taken up in 1.2 mL MeOH, acidified to pH 2 by addition of sufficient 1N HCl/MeOH. After evaporating the volatiles, the residue was triturated with chloroform and the salt was filtered off over a pad of celite. After removal of volatiles in vacuo, the residue was flash chromatographed over 14 mL silica gel (gradient elution with 2% to 20% methanol in CH$_2$Cl$_2$) to afford 37 mg of the title compound as a glassy solid.

$^1$H NMR (400 MHz, CD$_3$OD, ppm): δ0.89 (t, J=7.4 Hz, 3H), 1.37 (m, 2H), 1.56 (m, 2H), 2.57 (t, J=7.5 Hz, 2H), 5.61 (s, 1H), 7.00-7.10 (m, 2H), 7.25-7.70 (m, 11H).

FAB-MS: m/e 492 (M+1), 530 (M+K).

EXAMPLE 8

5-Butyl-4-[4-[(1-carboxy)(1-phenyl)methoxy]-3-propylphenyl]methyl-2-(2-chlorophenyl)-2,4-dihydro-3H-1,2,4-triazol-3-one Step A: Preparation of 5-Butyl-4-[4-[(1-carbomethoxy)(1-phenyl)methoxy]-3-propylphenyl]methyl-2-(2-chlorophenyl)-2,4-dihydro-3H-1,2,4-triazol-3-one This compound was prepared by the same procedure as for Example 7, Step D, except that methyl 2-(4-bromomethyl-2-propylphenoxy)-2-phenylacetate (the product of Example 6, Step H) was used as the alkylating agent. After chromatographic purification, a 96% yield of the desired material was obtained.

$^1$H NMR (400 MHz, CDCl$_3$, ppm): δ0.85 (t, J=7.4 Hz, 3H), 0.93 (m, 3H), 1.32 (m, 2H), 1.60 (m, 2H), 1.68 (m, 2H), 2.43 (t, J=7.7 Hz, 2H), 2.67 (t, J=7.7 Hz, 2H), 3.69 (s, 3H), 4.80 (s, 2H), 5.62 (s, 1H), 6.67 (d, J=8.4 Hz, 1H), 7.00-7.60 (m, 11H).

FAB-MS: m/e 548 (M+1).

Step B: Preparation of 5-butyl-4-[4-[(1-carboxy)(1-phenyl)methoxy]-3-propylphenyl]methyl-2-(2-chlorophenyl)-2,4-dihydro-3H-1,2,4-triazol-3-one This compound was prepared from the product of Step A by the same procedure as for Example 7, Step E. After chromatographic purification, a 50% yield of the title compound was obtained, homogeneous on TLC (9:1 CH$_2$Cl$_2$/MeOH).

$^1$H NMR (400 MHz, CDCl$_3$, ppm): δ0.82 (t, J=7.4 Hz, 3H), 0.91 (t, J=7.4 Hz, 3H), 1.40 (m, 2H), 1.55 (m, 2H), 1.63 (m, 2H), 2.41 (t, J=7.4 Hz, 2H), 2.66 (t, J=7.3 Hz, 2H), 4.80 (s, 2H), 5.60 (s, 1H), 6.68 (d, J=6.0 Hz, 1H), 6.95-7.60 (m, 11H).

FAB-MS: m/e 534 (M+1).

EXAMPLE 9

2-Benzyl-5-butyl-4-[4-[(1-carboxy)(1-(2-chlorophenyl))methoxy]phenyl]methyl-2,4-dihydro-3H-1,2,4-triazol-3-one Step A: Preparation of ethyl valerate carbethoxyhydrazone To a solution of 7.0 g (25.3 mmol) of ethyl valerimidate hydrochloride (prepared by method of A. J. Hill and I. Rabinowitz, J. Am. Chem. Soc., 1926, 48, 734) in 35 mL of dry ethanol stirred under N$_2$ at −78° C. was added dropwise a solution of 24 g (23 mmol) of ethyl carbazate in 35 mL of dry ethanol. Precipitation occurred during the addition, which took 20 minutes and was accompanied by a rise in the internal temperature of −50° C. The mixture was allowed to stand at 5° C. for 60 hours and then filtered. The filtrate was concentrated, then flash chromatographed on a silica gel column (elution with 98.5-1.5 CH$_2$Cl$_2$—MeOH), yielding 3.06 g (61%) of a clear oil, homogeneous by TLC in 97:3 CH$_2$Cl$_2$—MeOH; NMR suggested a mixture of syn and anti isomers.

$^1$H NMR (200 MHz, CDCl$_3$, ppm): δ0.91 (t, J=7 Hz, 3H), 1.2-1.4 (m, 8H), 1.4-1.6 (m, 2H), 2.2-2.4 (m, 2H), 3.95-4.3 (m, 4H), 6.91, 8.11 (br s, 1H total). FAB-MS: m/e 217 (M+1).

Step B: Preparation of methyl 2-bromo-2-(2-chlorophenyl)acetate

A mixture of 5.00 g (29.3 mmol) of 2-chlorophenylacetic acid and 2.67 mL (36.6 mmol) of thionyl chloride was stirred and refluxed as 1.51 mL of bromine was slowly added through an addition funnel. After the addition was complete, the reaction mixture was refluxed overnight, then cooled to room temperature. Methanol (25 mL) was cautiously added, the reaction mixture was stirred an additional 1 hour and was then evaporated to an oil. The residue was purified on a silica gel flash chromatography column eluted with 5% ethyl acetate/hexane to afford 2.13 g (28%) of the title compound.

$^1$H NMR (300 MHz, CDCl$_3$, ppm): δ3.8 (s, 3H), 5.95 (s, 1H), 7.25–7.45 (m, 3H), 7.7–7.8 (m, 1H).

Step C: Preparation of methyl 2-(2-chlorophenyl)-2-(4-methylphenoxy)acetate

To a stirred (0° C.) suspension of 0.530 g (4.63 mmol) of a 35% oil dispersion of potassium hydride in 5 mL of anhydrous DMF was added 0.50 g (4.63 mmol) of p-cresol and 0.050 g of 18-crown-6. After stirring at room temperature for 15 minutes, a solution of 1.22 g (4.63 mmol) of the product of Step B in 5 mL of DMF was slowly added. The reaction mixture was stirred and allowed to warm to room temperature during 45 minutes. The reaction mixture was then partitioned between ethyl acetate and water, separated, dried (MgSO$_4$), filtered and evaporated in vacuo. The residue was purified on a silica gel flash chromatography column eluted with 5% ethyl acetate/hexane to afford 1.03 g (77%) of the title compound.

$^1$H NMR: (300 MHz, CDCl$_3$, ppm): δ2.25 (s, 3H), 3.8 (s, 3H), 6.12 (s, 1H), 6.85 (d, 2H), 7.05 (d, 2H), 7.28–7.35 (m, 2H), 7.40–7.45 (m, 1H), 7.63–7.70 (m, 1H).

EI-MS: m/e 290, 292 (M+).

Step D: Preparation of methyl 2-(4-bromomethylphenoxy)-2-(2-chlorophenyl)acetate To a solution of 0.200 g (0.69 mmol) of the product of Step C dissolved in 2 mL of carbon tetrachloride was added 0.117 g (0.95 eq) of N-bromosuccinimide and ca. 10 mg (catalytic amount) of AIBN. The reaction mixture was stirred and refluxed under a nitrogen atmosphere for 30 minutes, then cooled and concentrated in vacuo. The residual oil was purified on a silica gel flash chromatography column eluted with 5% ethyl acetate/hexane to afford 0.186 g (73%) of the title compound.

$^1$H NMR (300 MHz, CDCl$_3$, ppm): δ3.8 (s, 3H), 4.5 (s, 2H), 6.15 (s, 1H), 6.85–6.95 (d, 2H), 7.25–7.35 (m, 4H); 7.4–7.5 (m, 1H), 7.6–7.7 (m, 1H).

EI-MS: m/e 368, 370, 372 (M+1, 10:13:3 ratio).

Step E: Preparation of methyl 2-[4-(azidomethyl)-phenoxy]-2-(2-chlorophenyl)acetate A concentrated stirred solution of the product of Step D in anhydrous dimethylsulfoxide (DMSO) is treated at ambient temperature with lithium azide (25% excess) portionwise. The mixture is then stirred at ambient temperature under protection from moisture for about 1 hour, or until TLC indicates complete reaction. The mixture is then partitioned between ether (or ethyl acetate) and water. The organic phase is washed repeatedly with H$_2$O, then dried over MgSO$_4$, filtered, and concentrated. The residue may be purified by chromatography on silica gel.

Step F: Preparation of methyl 2-[4-(aminomethyl)-phenoxy]-2-(2-chlorophenyl)acetate A solution of the product of Step E in dry tetrahydrofuran is treated protionwise with triphenylphosphine (1 equivalent). The solution is stirred under N$_2$ at ambient temperature. After about 2 hours, when gas evolution has ceased, H$_2$O (1 equivalent) is added, and the solution is concentrated in vacuo, and the residue is chromatographed on silica gel to give the title compound.

Step G: Preparation of 5-butyl-4-[4-[((1-carbomethoxy)(1-(2-chlorophenyl))methoxy]phenyl]methyl-2,4-dihydro-3H-1,2,4-triazol-3-one A mixture of approximately equimolar quantities of ethyl valerimidate carbethoxyhydrazone (from Step A) and methyl 2-[4-(aminomethyl)phenoxy]-2-(2-chlorophenyl)acetate (Step F) in ethanol is stirred at 80° C. under N$_2$. After about 2 hours, or when TLC indicates complete reaction, the mixture is cooled and concentrated to dryness. The residue is re-concentrated from CH$_2$Cl$_2$ and then chromatographed on silica gel to yield the title compound.

Step H: Preparation of 2-benzyl-5-butyl-4-[4-(1-carbomethoxy)(1-(2-chlorophenyl))methoxy]phenyl]methyl-2,4-dihydro-3H-1,2,4-triazol-3-one A mixture of the above ester (Step G), sodium hydride (3 equivalents), and dry DMF is stirred under N$_2$ at room temperature for 2 hours. Next, benzyl bromide (5 equivalents) is added, and stirring at room temperature is continued for an additional 1.5 hours or until TLC indicates complete reaction. The mixture is quenched by cautious addition of sufficient acetic acid to destroy the excess sodium hydride and then partitioned between ethyl acetate and H$_2$O. The ethyl acetate phase is washed repeatedly with H$_2$O, then dried (Na$_2$SO$_4$), filtered, and concentrated in vacuo. Chromatography of the residue on silica gel affords the title compound.

Step I: Preparation of 2-benzyl-5-butyl-4-[4-[(1-carboxy)(1-(2-chlorophenyl))methoxy]phenyl]methyl-2,4-dihydro-3H-1,2,4-triazol-3-one.

A solution of the above ester (Step H) in methanol is treated with 2.5N NaOH (10 equivalents). The solution is stirred at room temperature for about 2 hours or until TLC indicates complete reaction. Then the solution is diluted with H$_2$O and acidified to pH=2 with dilute HCl. The product is collected on a filter or extracted with ethyl acetate and washed with dilute HCl (pH=2). If necessary, the title compound is further purified by chromatography on silica gel.

What is claimed is:

1. A compound of Formula I

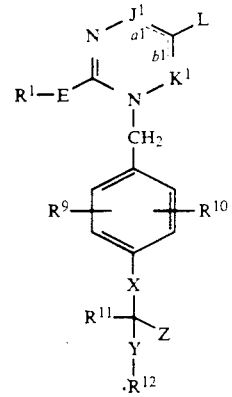

or a pharmaceutically acceptable salt thereof wherein:
R$^1$ is:
(a) (C$_1$–C$_6$)-alkyl, (C$_2$–C$_6$)-alkenyl or (C$_2$–C$_6$)-alkynyl each of which is unsubstituted or substituted with a substituent selected from the group consisting of:
  i) aryl as defined below,
  ii) (C$_3$–C$_7$)-cycloalkyl, iii) Cl, Br, I, F,
iv) OH,
v) NH$_2$,
vi) NH(C$_1$-C$_4$)-alkyl,
vii) N[(C$_1$-C$_4$)-alkyl)]$_2$,
viii) NHSO$_2$R$^2$,
ix) CF$_3$,
x) COOR$^2$, or
xi) SO$_2$NHR$^{2a}$; and
(b) aryl, wherein aryl is defined as phenyl or naphthyl unsubstituted or substituted with 1 or 2 substituents selected from the group consisting of:
i) Br, I, Cl, F,
ii) (C$_1$-C$_4$)-alkyl,
iii) (C$_1$-C$_4$)-alkoxy,
iv) NO$_2$
v) CF$_3$
vi) SO$_2$NR$^{2a}$R$^{2a}$,
vii) (C$_1$-C$_4$)-alkylthio,
viii) hydroxy,
ix) amino,
x) (C$_3$-C$_7$)-cycloalkyl,
xi) (C$_3$-C$_{10}$)-alkenyl; and
(c) (C$_1$-C$_4$)-perfluoroalkyl; and
E is a single bond; and
n is 0 to 2; and
J$^1$ is (a) —C(=O)—, (b) J$^1$ and L are connected together to form a 6-carbon aromatic ring substituted with R$^{7a}$, R$^{7b}$, R$^{8a}$ and R$^{8b}$; and
K$^1$ is (a) —C(=O)—, (b) K$^1$ and L are connected together to form a 6-carbon aromatic ring substituted with R$^{7a}$, R$^{7b}$, R$^{8a}$ and R$^{8b}$; and
one of a$^1$ or b$^1$ is a double bond provided that when J$^1$ is —C(=O)— then b$^1$ is a double bond and when K$^1$ is —C(=O)— then a$^1$ is a double bond,
L is the point of attachment of the 6-membered fused aromatic ring optionally having one nitrogen atom; and
R$^2$ is:
(a) H, or
(b) (C$_1$-C$_6$)-alkyl; and
R$^{2a}$ is:
(a) R$^2$,
(b) benzyl, or
(c) phenyl; and
R$^{7a}$ and R$^{7b}$ are independently
(a) H,
(b) (C$_1$-C$_6$)-alkyl, (C$_2$-C$_6$)-alkenyl or (C$_2$-C$_6$)-alkynyl,
(c) Cl, Br, I, F, or
(d) CF$_3$;
R$^{8a}$ and R$^{8b}$ are independently
(a) H,
(b) aryl-(C$_1$-C$_4$)-alkyl,
(c) (C$_1$-C$_6$)-alkyl, which is unsubstituted or substituted with a substituent selected from the group consisting of: —CON(R$^{2a}$)$_2$, —S(O)$_n$—R$^{21}$, —CONHSO$_2$R$^{21}$, —SO$_2$NHCOR$^{21}$, —SO$_2$NH—CN, —NR$^2$COOR$^{21}$, —OH, —NH$_2$, (C$_1$-C$_4$)-alkoxy, (C$_1$-C$_4$)-alkylthio, (C$_1$-C$_4$)-alkylamino, (C$_1$-C$_4$)-dialkylamino, —COOR$^{2a}$, —CONHR$^{2a}$, —O—COR$^{2a}$, or aryl,
(d) —CO-aryl,
(e) (C$_3$-C$_7$)-cycloalkyl,
(f) Cl, Br, I, F,
(g) —OH,
(h) —OR$^{21}$,
(i) —SH,
(j) —S(O)$_n$—(C$_1$-C$_4$)-alkyl,
(k) —COR$^{2a}$,
(l) —CO$_2$H,
(m) —CO$_2$—(C$_1$-C$_4$)-alkyl,
(n) —SO$_3$H,
(o) —NR$^2$R$^{21}$,
(p) —NR$^2$COR$^{21}$,
(q) —NR$^2$COOR$^{21}$,
(r) —SO$_2$NHR$^{2a}$,
(s) —SO$_2$NR$^2$R$^{2a}$,
(t) —NO$_2$,
(u) —NHSO$_2$CF$_3$,
(v) —CONR$^{2a}$R$^{2a}$,
(w) —(C$_1$-C$_4$)-perfluoroalkyl,
(x) —COOR$^2$,
(y) —SO$_3$H,
(z) —N(R$^2$)SO$_2$R$^{21}$,
(aa) —NR$^2$CONR$^{2a}$R$^{21}$,
(bb) —OC(=O)NR$^{21}$R$^{2a}$,
(cc) -aryl,
(dd) —NHSO$_2$CF$_3$,
(ee) —SO$_2$NHCOR$^{21}$,
(ff) —CONHSO$_2$R$^{21}$,
(gg) —PO(OR$^2$)$_2$,
(hh) —SO$_2$NHCN; and
R$^9$ and R$^{10}$ are independently:
(a) H,
(b) (C$_1$-C$_6$)-alkyl, unsubstituted or substituted with (C$_3$-C$_7$)-cycloalkyl,
(c) (C$_2$-C$_6$)-alkenyl,
(d) (C$_2$-C$_6$)-alkynyl,
(e) Cl, Br, F, I,
(f) (C$_1$-C$_6$)-alkoxy,
(g) when R$^9$ and R$^{10}$ are on adjacent carbons, they can be joined to form an phenyl ring,
(h) perfluoro-(C$_1$-C$_6$)-alkyl,
(i) (C$_3$-C$_7$)-cycloalkyl, unsubstituted or substituted with (C$_1$-C$_6$)-alkyl,
(j) aryl,
(k) (C$_1$-C$_6$)-alkyl-S(O)$_n$—(CH$_2$)$_n$—,
(l) hydroxy-(C$_1$-C$_6$)-alkyl,
(m) —CF$_3$,
(n) —CO$_2$R$^{2a}$,
(o) —OH,
(p) —NR$^2$R$^{21}$,
(q) —[(C$_1$-C$_6$)-alkyl]NR$^2$R$^{21}$,
(r) —NO$_2$,
(s) —(CH$_2$)$_n$—SO$_2$—N(R$^2$)$_2$,
(t) —NR$^2$CO—(C$_1$-C$_4$)-alkyl, or
(u) —CON(R$^2$)$_2$;
X is:
(a) —O—,
(b) —S(O)$_n$—,
(c) —NR$^{13}$—
(d) —CH$_2$O—,
(e) —CH$_2$S(O)$_n$,
(f) —CH$_2$NR$^{13}$—,
(g) —OCH$_2$—,
(h) —NR$^{13}$CH$_2$—,
(i) —S(O)$_n$CH$_2$—,
(j) —CH$_2$—,
(k) —(CH$_2$)$_2$—,
(l) single bond, or
(m) —CH=, wherein Y and R$^{12}$ are absent forming a —C=C— bride to the carbon bearing Z and R$^{11}$; and
Y is:

(a) single bond,
(b) —O—,
(c) —S(O)$_n$—,
(d) —NR$^{13}$—, or
(e) —CH$_2$—; and
except that X and Y are not defined in such a way that the carbon atom to which Z is attached also simultaneously is bonded to two heteroatoms (O, N, S, SO, SO$_2$);

R$^{11}$ and R$^{12}$ are independently:
(a) H,
(b) (C$_1$-C$_6$)-alkyl, unsubstituted or substituted with a substituent selected from the group consisting of:
  (i) aryl,
  (ii) (C$_3$-C$_7$)-cycloalkyl,
  (iii) NR$^2$R$^{21}$,
  (iv) OH,
  (v) CO$_2$R$^{2a}$, or
  (vi) CON(R$^2$)$_2$,
(c) aryl or aryl-(C$_1$-C$_2$)-alkyl, unsubstituted or substituted with 1 to 3 substituents selected from the group consisting of:
  (i) Cl, Br, I, F,
  (ii) (C$_1$-C$_6$)-alkyl,
  (iii) [(C$_1$-C$_5$)-alkenyl]CH$_2$—,
  (iv) [(C$_1$-C$_5$)-alkynyl]CH$_2$—,
  (v) (C$_1$-C$_6$)-alkyl-S(O)$_n$—(CH$_2$)$_n$—,
  (vi) —CF$_3$,
  (vii) —CO$_2$R$^{2a}$,
  (viii) —OH,
  (ix) —NR$^2$R$^{21}$,
  (x) —NO$_2$,
  (xi) —NR$^2$COR$^2$,
  (xii) —CON(R$^2$)2, or
  (xiii) —G—[(C$_1$-C$_6$)-alkyl]-R$^{23}$;
  and can additionally be substituted with 1 or 2 substituents selected from the group consisting of: Br, Cl or F, G is: a single bond, O, S(O)$_x$ or NR$^{23}$; and Z is:
(a) —CO$_2$H, or
(b) —CO$_2$R$^{24}$;

R$^{14}$ is:
(a) H,
(b) (C$_1$-C$_8$)-alkyl,
(c) (C$_1$-C$_8$)-perfluoroalkyl,
(d) (C$_3$-C$_6$)-cycloalkyl,
(e) phenyl, or
(f) benzyl; and R$^{21}$ is:
(a) H, or
(b) (C$_1$-C$_4$)-alkyl, is unsubstituted or substituted with:
  i) NH$_2$,
  ii) NH[(C$_1$-C$_4$)-alkyl],
  iii) N[(C$_1$-C$_4$)-alkyl]$_2$,
  iv) CO$_2$H,
  v) CO$_2$(C$_1$-C$_4$)-alkyl,
  vi) OH,
  vii) SO$_3$H, or
  viii) SO$_2$NH$_2$; and R$^{23}$ is:
(a) OH,
(b) NR$^2$R$^{21}$,
(c) CO$_2$R$^{2a}$,
(d) CON(R$^2$)$_2$, or
(e) S(O)$_x$—(C$_1$-C$_4$)-alkyl;

R$^{24}$ is:
(a) (C$_1$-C$_4$)-alkyl,
(b) CHR$^{25}$—O—COR$^{26}$,
(c) CH$_2$CH$_2$—N[(C$_1$-C$_2$)-alkyl]$_2$,
(d) (CH$_2$CH$_2$O)$_y$—O—[(C$_1$-C$_4$)-alkyl], wherein y is 1 or 2,
(e) aryl or CH$_2$-aryl, where aryl is as defined above and is substituted or unsubstituted with CO$_2$—(C$_1$-C$_4$)-alkyl, (f) 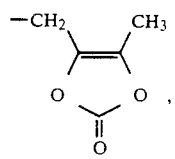

(g) 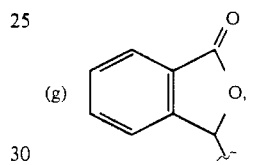

(h) 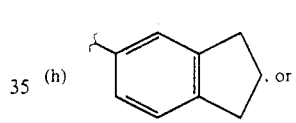, or (i) 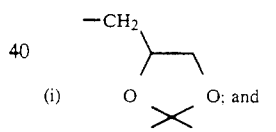; and

R$^{25}$ and R$^{26}$ independently are (C$_1$-C$_6$)-alkyl or phenyl.

2. The compound of claim 1 of structural formula

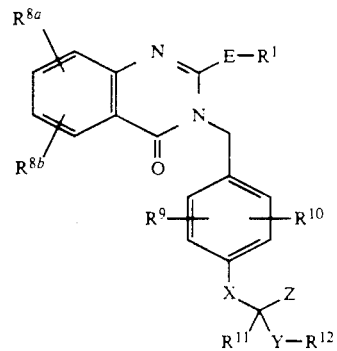

or a pharmaceutically acceptable salt thereof.

3. The compound of claim 1 of structural formula

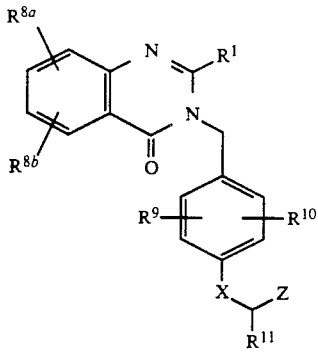

or a pharmaceutically acceptable salt thereof wherein:
R¹ is:
(a) $(C_1-C_6)$-alkyl, $(C_2-C_6)$-alkenyl or $(C_2-C_6)$-alkynyl each of which is unsubstituted or substituted with a substituent selected from the group consisting of:
  i) aryl as defined below,
  ii) $(C_3-C_7)$-cycloalkyl,
  iii) Cl, Br, I, F,
  iv) OH,
  v) $NH_2$,
  vi) $NH(C_1-C_4)$-alkyl,
  vii) $N[((C_1-C_4)$-alkyl$)]_2$,
  viii) $NHSO_2R^2$,
  ix) $CF_3$,
  x) $COOR^2$, or
  xi) $SO_2NHR^{2a}$; and
(b) aryl, wherein aryl is defined as phenyl or naphthyl unsubstituted or substituted with 1 or 2 substituents selected from the group consisting of:
  i) Br, I, Cl, F,
  ii) $(C_1-C_4)$-alkyl,
  iii) $(C_1-C_4)$-alkoxy,
  iv) $NO_2$
  v) $CF_3$,
  vi) $SO_2NR^{2a}R^{2a}$,
  vii) $(C_1-C_4)$-alkylthio,
  viii) hydroxy,
  ix) amino,
  x) $(C_3-C_7)$-cycloalkyl,
  xi) $(C_3-C_{10})$-alkenyl; and
(c) $(C_1-C_4)$-perfluoroalkyl; and
R² is:
(a) H, or
(b) $(C_1-C_6)$-alkyl; and
$R^{2a}$ is:
(a) R²,
(b) $CH_2$-aryl, or
(c) aryl; and
$R^{8a}$ and $R^{8b}$ are independently
(a) H,
(b) aryl-$(C_1-C_4)$-alkyl,
(c) $(C_1-C_6)$-alkyl, which is unsubstituted or substituted with a substituent selected from the group consisting of: —$CON(R^{2a})_2$, —$S(O)_n$—$R^{21}$, —$CONHSO_2R^{21}$, —$SO_2NHCOR^{21}$, —$SO_2NH$—$CN$, —$NR^2COOR^{21}$, —OH, —$NH_2$, $(C_1-C_4)$-alkoxy, $(C_1-C_4)$-alkylthio, $(C_1-C_4)$-alkylamino, $(C_1-C_4)$-dialkylamino, —$COOR^{2a}$, —$CONHR^{2a}$, —O—$COR^{2a}$, or aryl,
(d) —CO-aryl,
(e) $(C_3-C_7)$-cycloalkyl,
(f) Cl, Br, I, F,
(g) —OH,
(h) —$OR^{21}$,
(i) —SH,
(j) —$S(O)_n$—$(C_1-C_4)$-alkyl,
(k) —$COR^{2a}$,
(l) —$CO_2H$,
(m) —$CO_2$—$(C_1-C_4)$-alkyl,
(n) —$NR^2R^{21}$,
(o) —$NR^2COR^{21}$,
(p) —$NR^2COOR^{21}$,
(q) —$SO_2NR^2R^{2a}$,
(r) —$NO_2$,
(s) —$NHSO_2CF_3$,
(t) —$CONR^{2a}R^{2a}$,
(u) —$(C_1-C_4)$-perfluoroalkyl,
(v) —$COOR^2$,
(w) —$SO_3H$,
(x) —$N(R^2)SO_2R^{21}$,
(y) —$NR^2CONR^{2a}R^{21}$,
(z) —$OC(=O)NR^{21}R^{2a}$,
(aa) —aryl,
(bb) —$NHSO_2CF_3$,
(cc) —$SO_2NHCOR^{21}$,
(dd) —$CONHSO_2R^{21}$, or
(ee) —$SO_2NHCN$; and
$R^9$ and $R^{10}$ are independently:
(a) H,
(b) $(C_1-C_6)$-alkyl, unsubstituted or substituted with $(C_3-C_7)$-cycloalkyl,
(c) $(C_2-C_6)$-alkenyl,
(d) $(D_2-C_6)$-alkynyl,
(e) Cl, Br, F, I,
(f) $(C_1-C_6)$-alkoxy,
(g) when $R^9$ and $R^{10}$ are on adjacent carbons, they can be joined to form a phenyl ring,
(h) $(C_1-C_6)$-perfluoroalkyl,
(i) $(C_3-C_7)$-cycloalkyl, unsubstituted or substituted with $(C_1-C_6)$-alkyl,
(j) $(C_1-C_6)$-alkyl-$S(O)_n$—$(CH_2)_n$—,
(k) hydroxy-$(C_1-C_6)$-alkyl,
(l) —$CF_3$,
(m) —$CO_2R^{2a}$,
(n) —OH,
(o) —$[(C_1-C_6)$-alkyl$]NR^2R^{21}$,
(p) —$NR^2CO$—$(C_1-C_4)$-alkyl, or
(q) —$CON(R^2)_2$; and
X is:
(a) —O—,
(b) —$S(O)_n$—,
(c) —$CH_2O$—,
(d) —$CH_2S(O)_n$—,
(e) —$OCH_2$—,
(f) —$S(O)_nCH_2$—,
(g) —$CH_2$—,
(h) —$(CH_2)_2$—, or
(i) single bond, or
$R^{11}$ is:
(a) $(C_1-C_6)$-alkyl, unsubstituted or substituted with a substituent selected from the group consisting of:
  (i) aryl,
  (ii) $(C_3-C_7)$-cycloalkyl,
  (iii) $NR^2R^{21}$,
  (iv) OH,
  (v) $CO_2R^{2a}$, or
  (vi) $CON(R^2)_2$.

(b) aryl or aryl-($C_1$-$C_2$)-alkyl, unsubstituted or substituted with 1 to 3 substitutents selected from the group consisting of:
  (i) Cl, Br, I, F,
  (ii) ($C_1$-$C_6$)-alkyl,
  (iii) [($C_1$-$C_5$)-alkenyl]$CH_2$—,
  (iv) [($C_1$-$C_5$)-alkynyl]$CH_2$—,
  (v) ($C_1$-$C_6$)-alkyl-$S(O)_n$—$(CH_2)_n$—,
  (vi) —$CF_3$,
  (vii) —$CO_2R^{2a}$,
  (viii) —OH,
  (ix) —$NR^2R^{21}$,
  (x) —$NO_2$,
  (xi) —$NR^2COR^2$,
  (xii) —$CON(R^2)_2$,
  (xiii) —G—[($C_1$-$C_6$)-alkyl]-$R^{23}$,
  and can additionally be substituted with 1 or 2 substituents selected from the group consisting of: Br, Cl or F;
G is: a single bond, O, $S(O)_x$ or $NR^{23}$; and
Z is:
  (a) —$CO_2H$, or
  (b) —$CO_2R^{24}$, and
$R^{21}$ is:
  (a) H, or
  (b) ($C_1$-$C_4$)-alkyl, is unsubstituted or substituted with:
    i) $NH_2$,
    ii) NH[($C_1$-$C_4$)-alkyl],
    iii) N[($C_1$-$C_4$)-alkyl]$_2$,
    iv) $CO_2H$,
    v) $CO_2$($C_1$-$C_4$)-alkyl,
    vi) OH,
    vii) $SO_3H$, or
    viii) $SO_2NH_2$; and
$R^{22}$ is:
  (a) H,
  (b) ($C_1$-$C_4$)-alkyl,
  (c) ($C_1$-$C_4$)-alkoxyl,
  (d) aryl,
  (e) aryl-($C_1$-$C_4$)-alkyl,
  (f) $CO_2R^{2a}$,
  (g) $CON(R^2)_2$,
  (h) $SO_2R^{2a}$,
  (i) $SO_2N(R^2)_2$,
$R^{24}$ is:
  (a) ($C_1$-$C_4$)-alkyl,
  (b) $CHR^{25}$—O—$COR^{26}$,
  (c) $CH_2CH_2$—N[($C_1$-$C_2$)-alkyl]$_2$,
  (e) $(CH_2CH_2O)_y$—O—[($C_1$-$C_4$)-alkyl], wherein y is 1 or 2,
  (f) aryl or $CH_2$-aryl, where aryl is as defined above or optionally substituted with $CO_2$—($C_1$-$C_4$)-alkyl; and
$R^{25}$ and $R^{26}$ independently are ($C_1$-$C_6$)-alkyl or phenyl.

4. A compound of structural formula

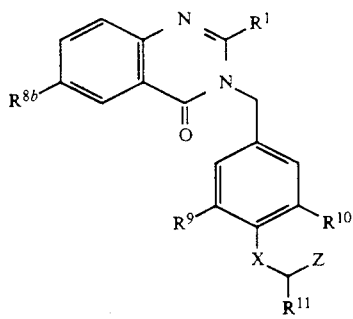

or a pharmaceutically acceptable salt thereof wherein:
$R^1$ is:
  (a) ($C_1$-$C_6$)-alkyl, ($C_2$-$C_6$)-alkenyl or ($C_2$-$C_6$)-alkynyl each of which is unsubstituted or substituted with a substituent selected from the group consisting of:
    i) aryl as defined below,
    ii) ($C_3$-$C_7$)-cycloalkyl,
    iii) Cl, Br, I, F,
    iv) OH,
    v) $NH_2$,
    vi) NH($C_1$-$C_4$)-alkyl,
    vii) N[(($C_1$-$C_4$)-alkyl)]$_2$,
    viii) $NHSO_2R^2$,
    ix) $CF_3$,
    x) $COOR^2$, or
    xi) $SO_2NHR^{2a}$; and
  (b) aryl, wherein aryl is defined as phenyl or naphthyl unsubstituted or substituted with 1 or 2 substituents selected from the group consisting of:
    i) Br, I, Cl, F,
    ii) ($C_1$-$C_4$)-alkyl,
    iii) ($C_1$-$C_4$)-alkoxy,
    iv) $NO_2$
    v) $CF_3$
    vi) $SO_2NR^{2a}R^{2a}$,
    vii) ($C_1$-$C_4$)-alkylthio,
    viii) hydroxy,
    ix) amino,
    x) ($C_3$-$C_7$)-cycloalkyl,
    xi) ($C_3$-$C_{10}$)-alkenyl, or
  (c) ($C_1$-$C_4$)-perfluoroalkyl; and
n is 0 to 2; and
$R^2$ is:
  (a) H, or
  (b) ($C_1$-$C_6$)-alkyl; and
$R^{2a}$ is:
  (a) $R^2$,
  (b) $CH_2$-aryl, or
  (c) aryl; and
$R^{8b}$ is:
  (a) H,
  (d) ($C_1$-$C_6$)-alkyl, which is unsubstituted or substituted with a substituent selected from the group consisting of: —$CON(R^{2a})_2$, —$S(O)_n$—$R^{21}$, —$CONHSO_2R^{21}$, —$SO_2NHCOR^{21}$, —$SO_2NH$—CN, —$NR^2COOR^{21}$, —OH, —$NH_2$, ($C_1$-$C_4$)-alkoxy, ($C_1$-$C_4$)-alkylthio, ($C_1$-$C_4$)-alkylamino, ($C_1$-$C_4$)-dialkylamino, —$COOR^{2a}$, —$CONHR^{2a}$, —O—$COR^{2a}$, or aryl,
  (g) Cl, Br, I, F,
  (h) —$OR^{21}$,
  (i) —$S(O)_n$—($C_1$-$C_4$)-alkyl, (j) —COR$^{2a}$,
(k) —NR$^2$R$^{21}$,
(l) —NR$^2$COR$^{21}$,
(m) —NR$^2$COOR$^{21}$,
(n) —NO$_2$,
(o) —COOR$^2$, or
(p) —NR$^2$CONR$^{2a}$R$^{21}$; and R$^9$ and R$^{10}$ are independently:
(a) H,
(b) (C$_1$-C$_6$)-alkyl, unsubstituted or substituted with (C$_3$-C$_7$)-cycloalkyl,
(c) (C$_2$-C$_6$)-alkenyl,
(d) (C$_2$-C$_6$)-alkynyl,
(e) Cl, Br, F, I,
(f) (C$_1$-C$_6$)-alkoxy,
(g) (C$_1$-C$_6$)-perfluoroalkyl,
(h) (C$_3$-C$_7$)-cycloalkyl, unsubstituted or substituted with (C$_1$-C$_6$)-alkyl;

X is:
(a) —O—,
(b) —S(O)$_n$—,
(c) —CH$_2$—, or
(d) —CH=, which is double bonded to the carbon bearing Z and R$^{11}$; and R$^{11}$ is:
(a) (C$_1$-C$_6$)-alkyl, unsubstituted or substituted with a substituent selected from the group consisting of:
  (i) aryl,
  (ii) (C$_3$-C$_7$)-cycloalkyl,
  (iii) NR$^2$R$^{21}$,
  (iv) OH,
  (v) CO$_2$R$^{2a}$, or
  (vi) CON(R$^2$)$_2$,
(c) phenyl or phenyl-(C$_1$-C$_2$)-alkyl, unsubstituted or substituted with 1 to 3 substituents selected from the group consisting of:
  (i) Cl, Br, I, F,
  (ii) (C$_1$-C$_6$)-alkyl,
  (iii) [(C$_1$-C$_5$)-alkenyl]CH$_2$—,
  (iv) [(C$_1$-C$_5$)-alkynyl]CH$_2$—,
  (v) (C$_1$-C$_4$)alkoxy,
  (vi) (C$_1$-C$_6$)-alkyl-S(O)$_n$—(CH$_2$)$_n$—,
  (vi) —CF$_3$,
  (vii) —CO$_2$R$^{2a}$,
  (viii) —OH,
  (ix) —NR$^2$R$^{21}$,
  (x) —NR$^2$COR$^2$,
  (xi) —CON(R$^2$)$_2$,
  and can additionally be substituted with 1 or 2 substituents selected from the group consisting of: Br, Cl or F, Z is:
(a) —CO$_2$H, or
(b) —CO$_2$R$^{24}$, and R$^{21}$ is:
(a) H, or
(b) (C$_1$-C$_4$)-alkyl, is unsubstituted or substituted with:
  i) NH$_2$,
  ii) NH[(C$_1$-C$_4$)-alkyl],
  iii) N[(C$_1$-C$_4$)-alkyl]$_2$,
  iv) CO$_2$H,
  v) CO$_2$(C$_1$-C$_4$)-alkyl,
  vi) OH,
  vii) SO$_3$H, or
  viii) SO$_2$NH$_2$; and R$^{24}$ is:
(a) (C$_1$-C$_4$)-alkyl,
(b) CHR$^{25}$—O—COR$^{26}$,
(c) CH$_2$CH$_2$O)$_y$—O—[(C$_1$-C$_4$)-alkyl], wherein y is 1 or 2, R$^{25}$ and R$^{26}$ independently are (C$_1$-C$_6$)-alkyl or phenyl.

5. A compound of structural formula

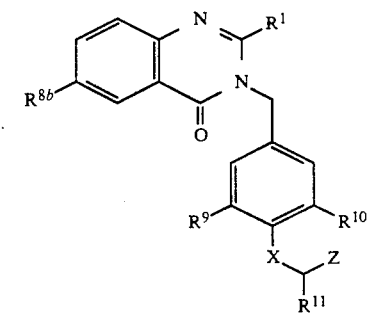

or a pharmaceutically acceptable salt thereof wherein:
R$^1$ is:
(a) (C$_1$-C$_6$)-alkyl, (C$_2$-C$_6$)-alkenyl or (C$_2$-C$_6$)-alkynyl each of which is unsubstituted or substituted with a substituent selected from the group consisting of:
  i) phenyl,
  ii) (C$_3$-C$_7$)-cycloalkyl,
  iii) Cl, Br, I, F,
  iv) CF$_3$,
(b) phenyl, unsubstituted or substituted with 1 or 2 substituents selected from the group consisting of:
  i) Br, I, Cl, F,
  ii) (C$_1$-C$_4$)-alkyl,
  iii) (C$_1$-C$_4$)-alkoxy,
  iv) NO$_2$
  v) CF$_3$
  vi) SO$_2$NR$^{2a}$R$^{2a}$,
  vii) (C$_1$-C$_4$)-alkylthio, or
  viii) (C$_3$-C$_{10}$)-alkenyl, or
(c) perfluoro-(C$_1$-C$_4$)-alkyl; and R$^2$ is:
(a) H, or
(b) (C$_1$-C$_6$)-alkyl; and R$^{2a}$ is:
(a) R$^2$,
(b) CH$_2$-phenyl, or
(c) phenyl; and R$^{8b}$ is:
(a) H,
(b) (C$_1$-C$_6$)-alkyl, which is unsubstituted or substituted with a substituent selected from the group consisting of: —CON(R$^{2a}$)$_2$, —CONHSO$_2$R$^{21}$, —NR$^2$COOR$^{21}$, (C$_1$-C$_4$)-alkoxy, (C$_1$-C$_4$)-alkylthio, —COOR$^{2a}$, —CONHR$^{2a}$
(c) —CO-aryl,
(d) Cl, Br, I, F,
(e) —OR$^{21}$,
(f) —S(O)$_n$—(C$_1$-C$_4$)-alkyl,
(g) —NR$^2$R$^{21}$,
(h) —NR$^2$COR$^{21}$,
(i) —NR$^2$COOR$^{21}$,
(j) —NO$_2$,
(k) —NHSO$_2$CF$_3$,
(l) —C$_1$-C$_4$-perfluoroalkyl, (m) —N(R$^2$)SO$_2$R$^{21}$,
(n) —NR$^2$CONR$^4$R$^{21}$, n is 0 to 2; and R$^9$ and R$^{10}$ are independently:
- (a) H,
- (b) (C$_1$-C$_6$)-alkyl, unsubstituted or substituted with (C$_3$-C$_7$)-cycloalkyl,
- (c) (C$_2$-C$_6$)-alkenyl,
- (d) (C$_2$-C$_6$)-alkynyl,
- (e) Cl, Br, F, I,
- (f) (C$_1$-C$_6$)-alkoxy,
- (g) (C$_1$-C$_6$)-perfluoroalkyl,
- (h) (C$_3$-C$_7$)-cycloalkyl, unsubstituted or substituted with (C$_1$-C$_6$)-alkyl, X is O; and R$^{11}$ is:
- (a) phenyl, unsubstituted or substituted with 1 to 5 substitutents selected from the group consisting of:
  - i) Cl, Br, I, F,
  - ii) (C$_1$-C$_6$)-alkyl,
  - iii) [(C$_1$-C$_5$)-alkenyl]CH$_2$—,
  - iv) [(C$_1$-C$_5$)-alkynyl]CH$_2$—,
  - v) (C$_1$-C$_6$)-alkoxy,
  - vi) (C$_1$-C$_6$)-alkyl-S(O)$_n$—(CH$_2$)$_n$—,
  - vii) hydroxy-(C$_1$-C$_6$)-alkyl,
  - viii) —CF$_3$,
  - ix) —CO$_2$R$^{2a}$,
  - x) —OH,
  - xi) —NR$^2$R$^{21}$,
  - xii) —[(C$_1$-C$_6$)-alkyl]NR$^2$R$^{21}$,
  - xiii) —NO$_2$,
  - xiv) —(CH$_2$)$_n$—SO$_2$—N(R$^2$)$_2$,
  - xv) —NR$^2$CO—(C$_1$-C$_4$)-alkyl, or
  - xvi) —CON(R$^2$)2;
- (b) phenyl-(C$_1$-C$_2$)-alkyl, unsubstituted or substituted with 1 to 5 substitutents selected from the group consisting of:
  - i) Cl, Br, I, F,
  - ii) (C$_1$-C$_6$)-alkyl,
  - iii) [(C$_1$-C$_5$)-alkenyl]CH$_2$—,
  - iv) [(C$_1$-C$_5$)-alkynyl]CH$_2$—,
  - v) (C$_1$-C$_4$)-alkoxy,
  - vi) (C$_1$-C$_4$)-alkylthio,
  - vii) hydroxy-(C$_1$-C$_6$)-alkyl,
  - viii) —CF$_3$,
  - ix) —CO$_2$R$^{2a}$,
  - x) —OH,
  - xi) —NR$^2$R$^{21}$,
  - xii) —[(C$_1$-C$_6$)-alkyl]NR$^2$R$^{21}$,
  - xiii) —NO$_2$,
  - xiv) —(CH$_2$)$_n$—SO$_2$—N(R$^2$)$_2$,
  - xv) —NR$^2$CO—(C$_1$-C$_4$)-alkyl, or
  - xvi) —CON(R$^2$)2, Z is:
- (a) —CO$_2$H, or
- (b) —CO$_2$—(C$_1$-C$_6$)-alkyl, and R$^{21}$ is:
- (a) H, or
- (b) (C$_1$-C$_4$)-alkyl.

6. A compound or its pharmaceutically acceptable salt which is selected from the group consisting of:
2-butyl-3-[4-(1-carboxy-1-phenyl)methoxy)phenyl]-methyl-6-methylquinazolin-4(3H)-one;

2-butyl-3-[4-((1-carboxy-1-phenyl)methoxy)-3-allyl]-phenyl]methyl-6-methylquinazolin-4(3H)-one;

2-butyl-3-[4-((1-carboxy-1-phenyl)methoxy)-3-propylphenyl]methyl-6-methylquinazolin-4(3H)-one;

2-butyl-3-[4-((1-carboxy-1-phenyl)methoxy)-3-chlorophenyl]methyl-6-methylquinazolin-4(3H)-one;

3-[4-((1-carboxy-1-phenyl)methoxy)-3-chloro-5-methoxyphenyl]methyl-6-(N-methyl-N-iso-butyloxycarbonyl)amino-2-propylquinazolin-4(3H)-one; or 3-[4-((1-carboxy-1-phenyl)methoxy)-3-propylphenyl]methyl-6-(N-methyl-N-iso-butyloxycarbonyl)amino-2-propylquinazolin-4(3H)-one.

7. A pharmaceutical composition useful in the treatment of hypertension which comprises a pharmaceutically acceptable carrier and a therapeutically effective amount of a compound of claim 1.

8. An ophthalmological formulation for the treatment of ocular hypertension comprising an ophthalmologically acceptable carrier and an effective ocular antihypertensive amount of a compound of claim 1.

* * * * *